US011685790B2

(12) United States Patent
Hofer et al.

(10) Patent No.: US 11,685,790 B2
(45) Date of Patent: *Jun. 27, 2023

(54) ANTIBODIES BINDING TO STEAP-1

(71) Applicant: Hoffmann-La Roche Inc., Little Falls, NJ (US)

(72) Inventors: Thomas Hofer, Zurich (CH); Maximiliane Koenig, Diesenhofen (DE); Ekkehard Moessner, Kreuzlingen (CH); Jens Niewoehner, Munich (DE); Tina Weinzierl, Eggenwil (CH); Laurent Lariviere, Westendorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 80 days.

This patent is subject to a terminal disclaimer.

(21) Appl. No.: 17/399,988

(22) Filed: Aug. 11, 2021

(65) Prior Publication Data
US 2022/0041747 A1 Feb. 10, 2022

Related U.S. Application Data

(63) Continuation of application No. 16/587,606, filed on Sep. 30, 2019, now Pat. No. 11,180,571, which is a continuation of application No. PCT/EP2018/058043, filed on Mar. 29, 2018.

(30) Foreign Application Priority Data

Apr. 3, 2017 (EP) .................................... 17164466

(51) Int. Cl.
*C07K 16/30* (2006.01)
*C07K 16/28* (2006.01)
*A61P 35/00* (2006.01)

(52) U.S. Cl.
CPC .......... *C07K 16/3069* (2013.01); *A61P 35/00* (2018.01); *C07K 16/2809* (2013.01); *C07K 2317/31* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,140,707 A | 2/1979 | Cleare et al. |
| 4,676,980 A | 6/1987 | Segal et al. |
| 4,737,456 A | 4/1988 | Weng et al. |
| 4,808,614 A | 2/1989 | Hertel et al. |
| 4,814,470 A | 3/1989 | Colin et al. |
| 5,208,020 A | 5/1993 | Chari et al. |
| 5,416,064 A | 5/1995 | Chari et al. |
| 5,500,362 A | 3/1996 | Robinson et al. |
| 5,565,332 A | 10/1996 | Hoogenboom et al. |
| 5,571,894 A | 11/1996 | Wels et al. |
| 5,587,458 A | 12/1996 | King et al. |
| 5,597,531 A | 1/1997 | Liberti et al. |
| 5,698,271 A | 12/1997 | Liberti et al. |
| 5,731,168 A | 3/1998 | Carter et al. |
| 5,750,373 A | 5/1998 | Garrard et al. |
| 5,770,429 A | 6/1998 | Lonberg et al. |
| 5,821,337 A | 10/1998 | Carter et al. |
| 5,859,045 A | 1/1999 | Treppendahl et al. |
| 5,859,205 A | 1/1999 | Adair et al. |
| 5,869,045 A | 2/1999 | Hellstrom et al. |
| 5,869,046 A | 2/1999 | Presta et al. |
| 5,959,177 A | 9/1999 | Hein et al. |
| 5,969,108 A | 10/1999 | McCafferty et al. |
| 6,040,498 A | 3/2000 | Stomp et al. |
| 6,048,970 A | 4/2000 | Lal et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,329,503 B1 | 12/2001 | Afar et al. |
| 6,342,219 B1 | 1/2002 | Thorpe et al. |
| 6,365,362 B1 | 4/2002 | Terstappen et al. |
| 6,417,429 B1 | 7/2002 | Hein et al. |
| 6,420,548 B1 | 7/2002 | Vezina et al. |
| 6,737,056 B1 | 5/2004 | Presta et al. |
| 6,800,746 B2 | 10/2004 | Xu et al. |
| 6,833,438 B1 | 12/2004 | Afar et al. |

(Continued)

FOREIGN PATENT DOCUMENTS

| | | |
|---|---|---|
| CN | 101918420 | 12/2010 |
| CN | 101943703 | 1/2011 |

(Continued)

OTHER PUBLICATIONS (Cate et al. Genbank (Accession No. W86309) National Library of Medicine, Bethesda, MD (Nov. 1998)).
(Database EMBL Nucleotide and Protein Sequences, Aug. 25, 1996, XP002128081, AA032221, Hinxton, GB).
(Database EMBL Nucleotide and Protein Sequences, Jun. 15, 1998, XP002128084, AC004969 (clone D11121E10) Hinxton, GB).
(Database EMBL Nucleotide and Protein Sequences, May 13, 1997, XP002128082, AC002064, Hinxton, GB.).

(Continued)

*Primary Examiner* — Julie Wu
*Assistant Examiner* — Cheom-Gil Cheong
(74) *Attorney, Agent, or Firm* — Linda Wu

(57) ABSTRACT

The present invention generally relates to antibodies that bind to STEAP-1, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

1 Claim, 9 Drawing Sheets

Specification includes a Sequence Listing.

(56) References Cited

U.S. PATENT DOCUMENTS

| | | |
|---|---|---|
| 6,887,975 B2 | 5/2005 | Afar et al. |
| 6,982,321 B2 | 1/2006 | Winter et al. |
| 7,041,870 B2 | 5/2006 | Tomizuka et al. |
| 7,053,186 B2 | 5/2006 | Afar et al. |
| 7,087,409 B2 | 8/2006 | Barbas et al. |
| 7,091,186 B2 | 8/2006 | Senter et al. |
| 7,125,978 B1 | 10/2006 | Vezina et al. |
| 7,166,714 B2 | 1/2007 | Afar et al. |
| 7,189,826 B2 | 3/2007 | Rodman |
| 7,319,006 B2 | 1/2008 | Afar et al. |
| 7,332,581 B2 | 2/2008 | Presta et al. |
| 7,455,991 B2 | 11/2008 | Afar et al. |
| 7,485,299 B2 | 2/2009 | Afar et al. |
| 7,494,646 B2 | 2/2009 | Jakobovits et al. |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,575,749 B2 | 8/2009 | Afar et al. |
| 7,611,904 B2 | 11/2009 | Afar et al. |
| 7,642,054 B2 | 1/2010 | Afar et al. |
| 7,695,936 B2 | 4/2010 | Carter et al. |
| 7,727,533 B2 | 6/2010 | Afar et al. |
| 7,745,394 B2 | 6/2010 | Doronina et al. |
| 7,785,903 B2 | 8/2010 | Bond et al. |
| 7,855,275 B2 | 12/2010 | Eigenbrot et al. |
| 7,884,179 B2 | 2/2011 | Faris et al. |
| 7,928,201 B2 | 4/2011 | Afar et al. |
| 7,939,503 B2 | 5/2011 | Jakobovits et al. |
| 7,947,276 B2 | 5/2011 | Jakobovits et al. |
| 7,947,459 B2 | 5/2011 | Hubert et al. |
| 7,964,566 B2 | 6/2011 | Doronina et al. |
| 7,968,307 B2 | 6/2011 | Afar et al. |
| 7,985,840 B2 | 7/2011 | Fuh et al. |
| 7,994,135 B2 | 8/2011 | Doronina et al. |
| 8,008,442 B2 | 8/2011 | Jakobovits et al. |
| 8,013,135 B2 | 9/2011 | Jakobovits et al. |
| 8,053,551 B2 | 11/2011 | Afar et al. |
| 8,241,626 B2 | 8/2012 | Hubert et al. |
| 8,309,300 B2 | 11/2012 | Junutula et al. |
| 8,436,147 B2 | 5/2013 | Dennis et al. |
| 8,679,490 B2 | 3/2014 | Dennis et al. |
| 8,771,966 B2 | 7/2014 | Dennis et al. |
| 8,889,847 B2 | 11/2014 | Dennis et al. |
| 9,000,130 B2 | 4/2015 | Bhakta et al. |
| 9,023,605 B2 | 5/2015 | Jakobovits et al. |
| 9,593,167 B2 | 3/2017 | Dennis et al. |
| 9,617,346 B2 | 4/2017 | Jakobovits et al. |
| 10,017,577 B2 * | 7/2018 | Polakis ............... C07K 16/28 |
| 10,597,463 B2 | 3/2020 | Jakobovits et al. |
| 2002/0022248 A1 | 2/2002 | Xu et al. |
| 2003/0045682 A1 | 3/2003 | Afar et al. |
| 2003/0060612 A1 | 3/2003 | Goddard et al. |
| 2003/0064397 A1 | 4/2003 | Spancake et al. |
| 2003/0149531 A1 | 8/2003 | Hubert et al. |
| 2003/0157108 A1 | 8/2003 | Presta et al. |
| 2004/0093621 A1 | 5/2004 | Shitara et al. |
| 2004/0110282 A1 | 6/2004 | Kanda et al. |
| 2004/0132140 A1 | 7/2004 | Satoh et al. |
| 2004/0253232 A1 | 12/2004 | Jakobovits et al. |
| 2004/0259150 A1 | 12/2004 | Nakamura et al. |
| 2005/0031613 A1 | 2/2005 | Nakamura et al. |
| 2005/0079574 A1 | 4/2005 | Bond |
| 2006/0073150 A1 | 4/2006 | Faris et al. |
| 2007/0061900 A1 | 3/2007 | Murphy et al. |
| 2007/0071675 A1 | 3/2007 | Wu et al. |
| 2007/0117126 A1 | 5/2007 | Sidhu et al. |
| 2007/0134253 A1 | 6/2007 | Afar et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0226657 A1 | 9/2008 | Doronina et al. |
| 2008/0248053 A1 | 10/2008 | Doronina et al. |
| 2009/0280056 A1 | 11/2009 | Dennis et al. |
| 2010/0272742 A1 | 10/2010 | Afar et al. |
| 2011/0318371 A1 | 12/2011 | Afar et al. |
| 2012/0003247 A1 | 1/2012 | Doronina et al. |
| 2012/0027772 A1 | 2/2012 | Kabakoff et al. |
| 2012/0142607 A1 | 6/2012 | Jakobovits et al. |
| 2012/0148608 A1 | 6/2012 | Doronina et al. |
| 2013/0143237 A1 | 6/2013 | Atwal et al. |
| 2013/0209988 A1 | 8/2013 | Barber et al. |
| 2013/0280163 A1 | 10/2013 | Jakobovits et al. |
| 2017/0043034 A1 | 2/2017 | Gilbert et al. |
| 2017/0234883 A1 | 8/2017 | Dennis et al. |
| 2017/0275377 A1 | 9/2017 | Jacobovits et al. |
| 2018/0106809 A1 | 4/2018 | Dennis et al. |
| 2020/0247905 A1 | 8/2020 | Jakobovits et al. |

FOREIGN PATENT DOCUMENTS

| | | |
|---|---|---|
| CN | 102015998 A | 4/2011 |
| CN | 102272595 | 12/2011 |
| CN | 102492772 | 6/2012 |
| CN | 103792364 A | 5/2014 |
| CN | 104067127 A | 9/2014 |
| CN | 105899677 A | 8/2016 |
| CN | 106413756 A | 2/2017 |
| EA | 005601 B1 | 4/2005 |
| EP | 0404097 B1 | 9/1996 |
| EP | 0 834 563 A2 | 4/1998 |
| EP | 0 834 563 A3 | 4/1998 |
| EP | 1 308 459 A2 | 5/2003 |
| EP | 1 308 459 A3 | 5/2003 |
| EP | 1 429 793 A4 | 7/2005 |
| EP | 1870459 A1 | 12/2007 |
| GB | 2 136 425 A | 9/1984 |
| JP | H1164691 A | 6/1999 |
| JP | 2003-517306 A | 5/2003 |
| JP | 2014-516250 | 7/2014 |
| UA | 94628 | 5/2011 |
| WO | 93/01161 A1 | 1/1993 |
| WO | 93/16185 A2 | 8/1993 |
| WO | 93/16185 A3 | 8/1993 |
| WO | 94/09150 A1 | 4/1994 |
| WO | 94/11026 A2 | 5/1994 |
| WO | 94/11026 A3 | 5/1994 |
| WO | 95/14772 A1 | 6/1995 |
| WO | 96/027011 A1 | 9/1996 |
| WO | 97/30087 A1 | 8/1997 |
| WO | 98/18489 A1 | 5/1998 |
| WO | 98/37093 A2 | 8/1998 |
| WO | 98/37093 A3 | 8/1998 |
| WO | 98/37418 A2 | 8/1998 |
| WO | 98/37418 A3 | 8/1998 |
| WO | 98/050431 A2 | 11/1998 |
| WO | 98/050431 A3 | 11/1998 |
| WO | 98/53071 A1 | 11/1998 |
| WO | 98/58964 A1 | 12/1998 |
| WO | 99/06548 A2 | 2/1999 |
| WO | 99/06548 A3 | 2/1999 |
| WO | 99/06550 A2 | 2/1999 |
| WO | 99/06550 A3 | 2/1999 |
| WO | 99/22764 A1 | 5/1999 |
| WO | 99/54342 A1 | 10/1999 |
| WO | 99/61469 A2 | 12/1999 |
| WO | 99/61469 A3 | 12/1999 |
| WO | 99/62941 A2 | 12/1999 |
| WO | 99/62941 A3 | 12/1999 |
| WO | 00/04149 A2 | 1/2000 |
| WO | 00/04149 A3 | 1/2000 |
| WO | 00/35937 A1 | 6/2000 |
| WO | 00/77021 A1 | 12/2000 |
| WO | 01/12662 A2 | 2/2001 |
| WO | 01/12662 A3 | 2/2001 |
| WO | 01/24811 A1 | 4/2001 |
| WO | 01/25272 A2 | 4/2001 |
| WO | 01/25272 A3 | 4/2001 |
| WO | 01/34802 A2 | 5/2001 |
| WO | 01/34802 A3 | 5/2001 |
| WO | 01/40276 A2 | 6/2001 |
| WO | 01/40276 A3 | 6/2001 |
| WO | 01/51633 A2 | 7/2001 |
| WO | 01/51633 A3 | 7/2001 |
| WO | 01/57190 A2 | 8/2001 |

(56) References Cited

FOREIGN PATENT DOCUMENTS

| | | |
|---|---|---|
| WO | 01/57190 A3 | 8/2001 |
| WO | 01/57276 A3 | 8/2001 |
| WO | 01/57277 A2 | 8/2001 |
| WO | 01/57277 A3 | 8/2001 |
| WO | 01/60860 A2 | 8/2001 |
| WO | 01/60860 A3 | 8/2001 |
| WO | 01/72962 A2 | 10/2001 |
| WO | 01/72962 A3 | 10/2001 |
| WO | 01/73032 A2 | 10/2001 |
| WO | 01/73032 A3 | 10/2001 |
| WO | 01/75067 A2 | 10/2001 |
| WO | 01/75067 A3 | 10/2001 |
| WO | 01/077342 A1 | 10/2001 |
| WO | 01/86003 A2 | 11/2001 |
| WO | 01/86003 A3 | 11/2001 |
| WO | 01/94629 A2 | 12/2001 |
| WO | 01/94629 A3 | 12/2001 |
| WO | 01/96388 A2 | 12/2001 |
| WO | 01/96388 A3 | 12/2001 |
| WO | 02/10449 A2 | 2/2002 |
| WO | 02/10449 A3 | 2/2002 |
| WO | 02/16429 A2 | 2/2002 |
| WO | 02/16429 A3 | 2/2002 |
| WO | 02/26822 A2 | 4/2002 |
| WO | 02/26822 A3 | 4/2002 |
| WO | 02/57303 A2 | 7/2002 |
| WO | 02/57303 A3 | 7/2002 |
| WO | 02/059260 A2 | 8/2002 |
| WO | 02/059260 A3 | 8/2002 |
| WO | 02/95010 A2 | 11/2002 |
| WO | 02/95010 A3 | 11/2002 |
| WO | 02/102993 A2 | 12/2002 |
| WO | 02/102993 A3 | 12/2002 |
| WO | 02/102994 A2 | 12/2002 |
| WO | 02/102994 A3 | 12/2002 |
| WO | 03/004622 A2 | 1/2003 |
| WO | 03/004622 A3 | 1/2003 |
| WO | 03/009814 A2 | 2/2003 |
| WO | 03/009814 A3 | 2/2003 |
| WO | 03/011878 A2 | 2/2003 |
| WO | 03/011878 A3 | 2/2003 |
| WO | 03/022955 A1 | 3/2003 |
| WO | 03/022995 A2 | 3/2003 |
| WO | 03/085107 A1 | 10/2003 |
| WO | 2004/010957 A2 | 2/2004 |
| WO | 2004/056312 A2 | 7/2004 |
| WO | 2004/056312 A3 | 7/2004 |
| WO | 2004/065540 A2 | 8/2004 |
| WO | 2004/106381 A1 | 12/2004 |
| WO | 02/30268 A2 | 4/2005 |
| WO | 02/30268 A3 | 4/2005 |
| WO | 2005/061547 A2 | 7/2005 |
| WO | 2005/081711 A2 | 9/2005 |
| WO | 2005/081711 A3 | 9/2005 |
| WO | 2005/100402 A1 | 10/2005 |
| WO | 2005/113601 A2 | 12/2005 |
| WO | 2005/113601 A8 | 12/2005 |
| WO | 2006/029879 A2 | 3/2006 |
| WO | 2006/029879 A3 | 3/2006 |
| WO | 2006/034488 A2 | 3/2006 |
| WO | 2006/034488 A3 | 3/2006 |
| WO | 2006/082515 A2 | 8/2006 |
| WO | 2007/042261 A2 | 4/2007 |
| WO | 2004/076643 | 9/2007 |
| WO | 2007/110205 A2 | 10/2007 |
| WO | 2007/147901 A1 | 12/2007 |
| WO | 2008/024715 A2 | 2/2008 |
| WO | 2008/052187 A2 | 5/2008 |
| WO | 2008/119567 A2 | 10/2008 |
| WO | 2009/080251 A1 | 7/2009 |
| WO | 2009/080252 A1 | 7/2009 |
| WO | 2009/089004 A1 | 7/2009 |
| WO | 2010/112193 A1 | 10/2010 |
| WO | 2010/115589 A1 | 10/2010 |
| WO | 2010/129304 A2 | 11/2010 |
| WO | 2010/129304 A3 | 11/2010 |
| WO | 2010/136172 A1 | 12/2010 |
| WO | 2010/145792 A1 | 12/2010 |
| WO | 2011/008990 | 1/2011 |
| WO | 2011/034605 A2 | 3/2011 |
| WO | 2011/090754 A1 | 7/2011 |
| WO | 2011/090762 A1 | 7/2011 |
| WO | 2011/115892 A1 | 9/2011 |
| WO | 2011/127219 | 10/2011 |
| WO | 2011/143545 A1 | 11/2011 |
| WO | 2012/058768 A1 | 5/2012 |
| WO | 2012/058768 A8 | 5/2012 |
| WO | 2012/130831 A1 | 10/2012 |
| WO | 2013/026831 A1 | 2/2013 |
| WO | 2013/026833 A1 | 2/2013 |
| WO | 2013/026839 A1 | 2/2013 |
| WO | 2013/082249 | 6/2013 |
| WO | 2013/086031 | 6/2013 |
| WO | 2013/096291 A2 | 6/2013 |
| WO | 2013/096291 A3 | 6/2013 |
| WO | 2013/111054 | 8/2013 |
| WO | 2013/120929 A1 | 8/2013 |
| WO | 2013/157953 A1 | 10/2013 |
| WO | 2013/157954 A1 | 10/2013 |
| WO | 2014/165818 A2 | 10/2014 |
| WO | 2015/095539 A1 | 6/2015 |
| WO | 2015/149077 A1 | 10/2015 |
| WO | 2015/150447 A1 | 10/2015 |
| WO | 2015/161231 A1 | 10/2015 |
| WO | 2016/016299 A1 | 2/2016 |
| WO | 2016/020309 A1 | 2/2016 |
| WO | 2016/040856 A2 | 3/2016 |
| WO | 2016/172485 A2 | 10/2016 |

OTHER PUBLICATIONS (Database EMBL, 'Human BAC Clone CTB-167B5 form 7q21, complete sequence,', Jun. 17, 1998, XP002173859, AC003991, R. Waterston et al).

(Dulcert et al. Genbank, (Accession No. Y11840), National Library of Medicine, Bethesda, MD (Feb. 11, 1999)).

Alberts et al. et al. Molecular Biology of the Cell, 3rd edition New York:Garland Publishing, Inc.,:465 ( 1994).

Almagro and Fransson, "Humanization of antibodies" Front Biosci 13:1619-1633 (Jan. 1, 2008).

Atwell et al., "Stable Heterodimers from Remodeling the Domain Interface of a Homodimer using a Phage Dispaly Library" Journal of Mol. Biol. 270:26-35 ( 1997).

Baca, M., et al., "Antibody humanization using monovalent phage display" J Biol Chem 272(16):10678-10684 (Apr. 18, 1997).

Bacac, M., et al., "CEA TCB: A novel head-to-tail 2:1 T cell bispecific antibody for treatment of CEA-positive solid tumors" Oncoimmunology 5(8 Suppl e1203498):1-3 (Jun. 24, 2016).

Bazan, J., et al., "Phage display—A powerful technique for immunotherapy" Hum Vaccines Immuno 8(12):1817-1828 (Dec. 13, 2012).

Beitsch and Clifford, "Detection of carcinoma cells in the blood of breast cancer patients" Am J Surg. 180(6):446-449 (Dec. 2000).

Bellone et al., "Cancer immunotherapy: synthetic andnatural peptides in the balance" Immunol Today 20(10):457-462 ( 1999).

Boder et al., "Directed evolution of antibody fragments with monovalent femtomolar antigen-binding affinity" P Natl Acad Sci USA 97:10701-10705 ( 2000).

Boerner, P., et al., "Production of antigen-specific human monoclonal antibodies from in vitro-primed human splenocytes" J Immunol 147(1):86-95 (Jul. 1, 1991).

Bowie, J. et al., "Deciphering the message in protein sequences: tolerance to amino acid substitutions" Science 247(4948):1306-1310 (Mar. 16, 1990).

Brennan, M., "Preparation of bispecific antibodies by chemical recombination of monoclonal immunoglobulin G\\\subscript:1\\\fragments" Science 229:81-83 (Jul. 5, 1985).

Brodeur, B. et al., "Mouse-human myeloma partners for the production of heterohybridomas" Monoclonal Antibody Production Techniques and Applications (New York: Marcel Dekker, Inc.),:51-63 ( 1987).

(56) References Cited

OTHER PUBLICATIONS

Brueggermann, M., et al., "Comparison of the effector functions of human immunoglobulins using a matched set of chimeric antibodies" J. Exp. Med. 166(5):1351-1361 (Nov. 1, 1987).
Burgess, W., et al., "Possible dissociation of the heparin-binding and mitogenic activities of heparin-binding (Acidic Fibroblast) growth factor-1 from its receptor-binding activities by site-directed mutagenesis of a single lysine residue" J Cell Biol 111(5):2129-2138 (Nov. 1, 1990).
Carter et al., "Bispecific human IgG by design" J Immunol Methods 248(1-2):7-15 (Feb. 1, 2001).
Carter, P., et al., "Humanization of an anti-p185HER2 antibody for human cancer therapy" PNAS USA 89(10):4285-4289 (May 15, 1992).
Casset et al., "A peptide mimetic of an anti-CD4 monoclonal antibody by rational design" Biochem Bioph Res Co 307(1):198-205 (Jul. 18, 2003).
Challita-Eid et al., "Monoclonal Antibodies to Six-Transmembrane Epithelial Antigen of the Prostate-1 Inhibit Intercellular Communication In vitro and Growth of Human Tumor Xenografts In vivo" Cancer Res 67(12):5798-5805 ( 2007).
Chari et al., "Immunoconjugates containing novel maytansinoids: Promising anticancer drugs" Cancer Res 52:127-131 ( 1992).
Chen et al., "In vitro scanning saturation mutagenesis of all the specificity determining residues in an antibody binding site" Protein Eng 12(4):349-356 ( 1999).
Chen, Y., et al., "Selection and analysis of an optimized anti-VEGF antibody: crystal structure of an affinity-matured Fab in complex with antigen" J Mol Biol 293(4):865-881 (Sep. 13, 1999).
Cherf, G., et al., "Applications of yeast surface display for protein engineering" Methods Mol Biol 1319:155-175 (Jan. 1, 2015).
Chothia et al., "Canonical structures for the hypervariable regions of immunoglobulins" J Mol Biol 196(4):901-917 (Apr. 23, 1987).
Chou et al., "Screening asymptomatic adults with resting or exercise electrocardiography: a review of the evidence for the U.S. Preventive Services Task Force" Ann Intern Med. 155(6):375-386 (Sep. 2011).
Chou et al., "Screening for prostate cancer: a review of the evidence for the U.S. Preventive Services Task Force" Ann Intern Med. 155( Suppl 11):762-783 ( 2011).
Clynes, R., et al., "Fc receptors are required in passive and active immunity to melanoma" PNAS USA 95(2):652-656 (Jan. 1, 1998).
Colman, P.M., "Effects of amino acid sequence changes on antibody-antigen interactions" Res Immunol 145(1):33-36 (Jan. 1, 1994).
Cragg et al., "Antibody specificity controls in vivo effector mechanisms of anti-CD20 reagents" Blood 103(7):2738-2743 ( 2004).
Cragg, M., et al., "Complement-mediated lysis by anti-CD20 mAb correlates with segregation into lipid rafts" Blood 101(3):1045-1052 (Feb. 1, 2003).
Cristofanilli et al., "Circulating tumor cells, disease progression, and survival in metastatic breast cancer" N Engl J Med. 351(8):781-791 (Aug. 19, 2004).
Cristofanilli et al., "Circulating tumor cells: a novel prognostic factor for newly diagnosed metastatic breast cancer" J Clin Oncol. 23(7):1420-1430 (Mar. 1, 2005).
Cruz et al., "Evaluation of multiparameter flow cytometry for the detection of breast cancer tumor cells in blood samples" Am J Clin Pathol. 123(1):66-74 ( 2005).
Dall'Acqua et al., "Antibody humanization by framework shuffling" Methods 36:43-60 ( 2005).
Diss et al., "Expression of skeletal muscle-type voltage-gated Na+ channel in rat and human prostate cancer cell lines" FEBS Lett 427:5-10 ( 1998).
Djulbegovic et al., "Screening for prostate cancer: systematic review and meta-analysis of randomised controlled trials" BMJ 341:c4543 ( 2010).
Doronina et al., "Development Of Potent Monoclonal Antibody Auristatin Conjugates For Cancer Therapy" Nature Biotechnology 21(7):778-784 ( 2003).

Elbashir et al., "Duplexes Of 21-Nucleotide RNAS Mediate RNA Interference In Cultured Mammalian Cells" Nature 411:494-498 ( 2001).
English translation of Russian Decision on grant, dated Nov. 26, 2012, received in corresponding RU Patent Application No. 2009119976, filed on Oct. 26, 2007, 12 pages.
Faris et al., Proceedings of the annual meeting of the American Association for Cancer Research 43(4688):947 ( 2002).
Feezor et al., "Significance of micrometastases in colorectal cancer" Ann Surg Oncol. 9(10):944-953 ( 2002).
Fehm et al., "Cytogenetic evidence that circulating epithelial cells in patients with carcinoma are malignant" Clin Cancer Res. 8(7):2073-2084 (Jul. 2002).
Ferrara, C., et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi a-mannosidase II" Biotechnol Bioeng 93(5):851-861 (Jan. 24, 2006).
Flatman, S., et al., "Process analytics for purification of monoclonal antibodies" J Chromatogr B 848(1):79-87 (Mar. 15, 2007).
Frenzel, A., et al., "Phage display-derived human antibodies in clinical development and therapy" MABS 8(7):1177-1194 (Jul. 8, 2016).
Fu et al., "Translational regulation of human p53 gene expression" EMBO J 15(16):4392-4401 ( 1996).
Gazzano-Santoro et al., "A non-radioactive complement-dependent cytotoxicity assay for anti-CD20 monoclonal antibody" J Immunol Methods 202:163-171 ( 1997).
Gerngros, "Advances in the production of human therapeutic proteins in yeasts and filamentous fungi" Nat Biotechnol 22(11):1409-1414 (Nov. 2004).
Ghossein et al., "Review: polymerase chain reaction detection of micrometastases and circulating tumor cells: application to melanoma, prostate, and thyroid carcinomas" Diagn Mol Pathol. 8(4):165-175 (Dec. 1999).
Glaves et al., "Correlation between circulating cancer cells and incidence of metastases" Br J Cancer 48(5):665-673 (Nov. 1983).
Goldenberg, M., "Trastuzumab, a Recombinant DNA-Derived Humanized Monoclonal Antibody, a Novel Agent for the Treatment of Metastatic Breast Cancer" Clin Ther 21(2):309-318 (Feb. 1, 1999).
Graham, F., et al., "Characteristics of a Human Cell Line Transformed by DNA form Human Adenovirus Type5" J Gen Virol 36(1):59 (Jul. 1, 1977).
Greenspan et al., "Defining epitopes: It's not as easy as it seems" Nat Biotechnol 7:936-937 (Oct. 1999).
Griffiths, A., et al., "Human anti-self antibodies with high specificity from phage display libraries" EMBO J 12(2):725-734 (Feb. 1, 1993).
Grimes et al., "Electrophysiological characterization of voltage-gated Na+ current expressed in the highly metastatic Mat-LyLu cell line of rat prostate cancer" J Cel Physiol 175:50-58 ( 1998).
Gruber, M. et al., "Efficient tumor cell lysis mediated by a bispecific single chain antibody expressed in *Escherichia coli*" J Immunol 152(11):5368-5374 (Jun. 1, 1994).
Grunewald et al., "The STEAP protein family: Versatile oxidoreductases and targets for cancer immunotherapy with overlapping and distinct cellular functions" Biol Cell 104(11):641-657 (Nov. 1, 2012).
Gura, T., "Systems for Identifying New Drugs Are Often Faulty" Science 278(5340):1041-1042 (Nov. 7, 1997).
Gussow et al., "Humanization of Monoclnal Antibodies" Methods in Enzymology 203:99-121 ( 1991).
Gutierrez et al., "Activation of a Ca2+-permeable cation channel by two different inducers of appoptosis in a human prostatic cancer cell line" J Physiol 517.1:95-107 ( 1999).
Hanes, J., et al., "In vitro selection and evolution of functional proteins by using ribosome display" PNAS 94(10):4937-4942 (May 1, 1997).
Harlow et al. Cold Spring Harbor, NY:Cold Spring Harbor Laboratory,:65 pages ( 1988).
Haverstick et al., "Inhibition of human prostate cancer proliferation in vitro and in a mouse model by a compound synthesized to block Ca2+ Entry 1" Cancer Res:1002-1008 ( 2000).

(56) References Cited

OTHER PUBLICATIONS

He, M., et al., "Antibody-ribosome-mRNA (ARM) complexes as efficient selection particles for in vitro display and evolution of antibody combining sites" Nucleic Acids Res 25(24):5132-5134 (Oct. 4, 1997).
Heeley, R. et al., "Mutations Flanking the Polyglutamine Repeat in the Modulatory Domain of Rat Gucocorticoid Receptor Lead to an Increase in Affinity for Hormone" Endocr Res 28(3):217-229 (Aug. 1, 2002).
Hellstrom, I., "Antitumor effects of L6, an IgG2a antibody that reacts with most human carcinomas" PNAS US 83(18):7059-7063 (Sep. 1, 1986).
Hellstrom, I., et al., "Strong antitumor activities of IgG3 antibodies to a human melanoma-associated ganglioside"PNAS USA 82(5):1499-1502 (Mar. 1, 1985).
Herbert et al. The Dictionary of Immunology 4th edition,Academic Press,:58 ( 1995).
Holliger, P., et al., "Specific killing of lymphoma cells by cytotoxic T-cells mediated by a bispecific diabody" Protein Eng 9(3):299-305 (Mar. 1, 1996).
Hollinger, P., et al., "Diabodies: Small Bivalent and Bispecific Antibody Fragments" PNAS 90(14):6444-6448 (Jul. 15, 1993).
Holm et al. et al., "Functional mapping and single chain construction of the anti-cytokeratin 8 monoclonal antibody TS1" Mol Immunol 44(6):1075-1084 (Feb. 2007).
Hoogenboom and Winter, "By-passing immunisation. Human antibodies synthetic repertoires of germline VH gene segments rearranged in vitro" J Mol Biol 227(2):381-388 (Sep. 20, 1992).
Hoogenboom, H., et al., "Overview of antibody phage-display technology and its applications" Methods Mol Biol 178:1-37 ( 2002).
Hubert et al., "STEAP: a prostate-specific cell-surface antigen highly expressed in human prostate tumors" PNAS 96(25):14523-145528 (Dec. 7, 1999).
Hudson, P., et al., "Engineered antibodies" Nat Med 9(1):129-134 (Jan. 1, 2003).
International Preliminary Report on Patentability (IPRP) for PCT/EP2018/058043 dated Oct. 8, 2019.
International Search Report for PCT/EP2018/058043 dated May 29, 2018.
International Search Report dated Apr. 28, 2003 for PCT Patent Application No. PCT/US02/28371 filed on Sep. 6, 2002 (1 pg.)
Johnson, S., et al., "Effector Cell Recruitment with Novel Fv-based Dual-affinity Re-targeting Protein Leads to Potent Tumor Cytolysis and in Vivo B-cell Depletion" J Mol Biol 399(3):436-449 (Jun. 11, 2010).
Kabat, E. et al., "Sequences of Proteins of Immunological Interest" 1(Fifth Edition):647-660 ( 1991).
Kabat, E. et al., "Sequences of Proteins of Immunological Interest" 1(Fifth Edition):661-723 ( 1991).
Kam, N., et al., "Carbon nanotubes as multifunctional biological transporters and near-infrared agents for selective cancer cell destruction" PNAS 102(33):11600-11605 (Aug. 16, 2005).
Kanda, Y. et al., "Comparison of Cell Lines for Stable Production of Fucose-Negative Antibodies with Enhanced ADCC" Biotechnol Bioeng 94(4):680-688 (Jul. 1, 2006).
Kashmiri, S., et al., "SDR grafting—a new approach to antibody humanization" Methods 36:25-34 (Jan. 1, 2005).
Kindt et al. Kuby Immunology "Antigens and Antibodies Chapter 4" 6th ed edition, N.Y.:W.H. Freeman and Co,:p. 91 ( 2007).
Kipriyanov, S., et al., "Bispecific Tandem Diabody for Tumor Therapy with Improved Antigen Binding and Pharmacokinetics" J Mol Biol 293(1):41-56 (Oct. 15, 1999).
Klein, C. et al., "The use of CrossMAb technology for the generation of bi- and multispecific antibodies" MABS 8(6):1010-1020 (Aug. 31, 2016).
Klimka, A. et al., "Human anti-CD30 recombinant antibodies by guided phage antibody selection using cell panning" Brit J Cancer 83(2):252-260 (Jun. 15, 2000).
Kostelny et al., "Formation of a bispecific antibody by the use of leucine zippers" J Immunol 148(5):1547-1553 (Mar. 1, 1992).
Kozbor, D., et al., "A Human Hybrid Myeloma for Production of Human Monoclonal Antibodies" J Immunol 133(6):3001-3005 (Dec. 1, 1984).
Lazar et al., "Transforming Growth Factor α: Mutation of Aspartic Acid 47 and Leucine 48 Results in Different Biological Activities" Molecular and Cellular Biology 8(3):1247-1252 (Mar. 1988).
Lepple-Wienhues et al., "K + channels and the intracellular calcium signal in melanoma cell proliferation" J Membrane Biol 151:149-157 ( 1996).
Lerner, R., "Combinatorial antibody libraries: new advances, new immunological insights" Nat Rev Immunol 16(8):498-508 (Jul. 6, 2016).
Li, H., et al., "Optimization of humanized IgGs in glycoengineered *Pichia pastoris*" Nat Biotechnol 24(2):210-215 (Feb. 1, 2006).
Li, J., et al., "Human antibodies for immunotherapy development generated via a human B cell hybridoma technology" PNAS USA 103(10):3557-3562 (Mar. 7, 2006).
Liberti et al. (18 pages including book details), E. Pelizzetti,:777-790 ( 1996).
Liljeblad, M., et al., "Analysis of agalacto-IgG in rheumatoid arthritis using surface plasmon resonance" Glycoconjugate J 17:323-329 (Jul. 14, 2000).
Lonberg, N., et al., "Fully human antibodies from transgenic mouse and phage display platforms" Curr Opin Immunol 20(4):450-459 (Aug. 1, 2008).
MacCallum, R., et al., "Antibody-antigen Interactions: Contact Analysis and Binding Site Topography" J Mol Biol 262:732-745 (Oct. 11, 1996).
Marino et al., "Association between cell membrane potential and breast cancer" Tumor Biol 15:82-89 ( 1994).
Mariuzza et al., "The Structural Basis of Antigen-Antibody Recognition" Annu. Rev. Biophys. Biophs. Chem. 16:139-159 ( 1987).
Marks, James, et al. Methods Mol Biol "Chapter 8: Selection of Human Antibodies from Phage Display Libraries" Lo B.K.C. (eds), Totowa, New Jersey-US:Humana Press Inc., vol. 248:161-176 (Jan. 2004).
Marrinucci et al., "Case study of the morphologic variation of circulating tumor cells" Human Pathology 38(3):514-519 ( 2007).
Mashushita et al., "Upregulation of interleukin-13 and its receptor in a murine model of bleomycin-induced scleroderma" Int Arch Allergy Immunol 135:348-356 ( 2004).
Mather, J., "Establishment and Characterization of Two Distinct Mouse Testicular Epithelial Cell Lines" Biol Reprod 23:243-252 ( 1980).
Mather, J., et al., "Culture of Testicular Cells in Hormone-Supplemented Serum-Free Medium" Ann NY Acad Sci 383:44-68 (Jan. 1, 1982).
Matsunami et al., "Detection of bone marrow micrometastasis in gastric cancer patients by immunomagnetic separation" Ann Sug Oncol. 10(2):171-175 (Mar. 2003).
McClean et al., "Evidence of post-translational regulation of P-glycoprotein associated with the expression of a distinctive multiple drug-resistant phenotype in Chinese hamster ovary cells" Eur J Cancer 29(16):2243-2248 ( 1993).
Meng et al., "Circulating tumor cells in patients with breast cancer dormancy" Clin Cancer Res. 10(24):8152-8162 (Dec. 15, 2004).
Milstein, C., et al., "Hybrid hybridomas and their use in immunohistochemistry" Nature 305(5934):537-539 (Oct. 6, 1983).
Moiseenko et al., "Monoclonal antibodies in the treatment of malignant tumors" Practical Oncology), (Prakticheskaya Onkologiya), 4(3):148-156 ( 2003).
Nagorsen, D., et al., "Immunomodulatory therapy of cancer with T cell-engaging BiTE antibody blinatumomab" Exp Cell Res 317(9):1255-1260 (May 15, 2011).
Ni et al., "Research progress and future perspectives in antibodomics and antibodomic drugs" Xiandai Mianyixue ((Abstract only)), 26(4):265-268 ( 2006).
Nie et al., "Inhibitionof proliferation of MCF-7 breast cancer cells by a blocker of Ca2+-permeable channel" Cell Calcium 22(2):75-82 ( 1997).

(56) References Cited

OTHER PUBLICATIONS

Osbourn, J. et al., "From rodent reagents to human therapeutics using antibody guided selection" Methods 36(1):61-68 (May 1, 2005).

Pachmann et al., "Quantification of the response of circulating epithelial cells to neodadjuvant treatment for breast cancer: a new tool for therapy monitoring" Breast Cancer Research 7(6):R975-R979 ( 2005).

Padlan, E. et al., "A possible procedure for reducing the immunogenicity of antibody variable domains while preserving their ligand-binding properties" Mol Immunol 28(4-5):489-498 (Apr. 30, 1991).

Pan, Q. et al. et al., "Blocking neuropilin-1 function has an additive effect with anti-VEGF to inhibit tumor growth" Cancer Cell 11(1):53-67 (Jan. 1, 2007).

Pancrazio et al., "Voltage-dependent ion channels in small-cell lung cancer cells" Cancer Res. 49:5901-5906 ( 1989).

Paul, W.E. Fundamental Immunology ((under the heading of) Fv Structure and Diversity in Three Dimensions), 3rd edition,:292-295 ( 1993).

PCT International Search Report for PCT/US2016/028372, 5 pages (dated Oct. 27, 2016).

PCT Written Opinion of the ISA for PCT/US2016/028372, 9 pages (dated Oct. 27, 2016).

Pearson, W.R., et al., "Comparison of DNA Sequences with Protein Sequences" Genomics 46:24-36 (Aug. 25, 1997).

Pearson, W.R., et al., "Improved tools for biological sequence comparison" PNAS 85(8):2444-2448 (Apr. 1, 1988).

Pearson, W.R.,, "Effective Protein Sequence Comparison" Method Enzymol 266:227-258 (Jan. 1, 1996).

Petkova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).

Pluckthun et al. The Pharmacology of Monoclonal Antibodies Rosenburg and Moore (eds.), New York:Springer-Verlag, vol. 113:269-315 ( 1994).

Polakis, P. et al., "Antibody Drug Conjugates for Cancer Therapy" Pharmacol Rev 68(1):3-19 (Jan. 1, 2016).

Presta et al., "Humanization of an antibody directed against IgE" J Immunol 151(5):2623-2632 (Sep. 1, 1993).

Qu et al., "Detection and clinical application of circulating tumor cells in peripheral blood of patients with prostate cancer" China Oncology (including English translation of abstract), 23(1):64-68 ( 2013).

Queen et al., "A humanized Antibody that Binds to the Interleukin 2 Receptor" P.N.A.S. USA 86:10029-10033 ( 1989).

Racila et al., "Detection and characterization of carcinoma cells in the blood" Proc Natl Acad Sci USA 95(8):4589-4594 (Apr. 14, 1998).

Reiger et al. Glossary of Genetics and Cytogenetics "Agmatoploidy" NY: Springer-Verlag,: 17-18 ( 1976).

Remington et al. Remington's Pharmaceutical Sciences "Part 6: Pharmaceutical and !Medicinal Agents" 18th edition, Easton, PA-US:Mack Publishing,:1289-1329 (Jan. 1, 1990).

Ridgway, J., et al., "'Knobs-into-holes' engineering of antibody CH3 domains for heavy chain heterodimerization" Protein Eng 9(7):617-621 (Jul. 1, 1996).

Riechmann, L., et al., "Reshaping human antibodies for therapy" Nature 332:323-327 (Mar. 24, 1988).

Ripka, J., et al., "Two chinese hamster ovary glycosylation mutants affected in the conversion of GDP-mannose to GDP-fucose" Arch Biochem Biophys 249(2):533-545 (Sep. 1, 1986).

Roitt et al., "nteraction of Antibodies with Antigens" Immunology (Translation from Engl: Mir), 150:110 ( 2000).

Rosok, M., et al., "A combinatorial library strategy for the rapid humanization of anticarcinoma BR96 Fab" J Biol Chem 271(37):22611-22618 (Sep. 13, 1996).

Rudikoff, S., et al., "Single amino acid substitution altering antigen-binding specificity" PNAS USA 79(6):1979-1983 (Mar. 1, 1982).

Saffran et al., "Anti-PSCA mAbs inhibit tumor growth and metastasis formation and prolong the survival of mice bearing human prostate cancer xenografts" PNAS 98(5):2658-2663 ( 2001).

Schaefer, W., et al., "Immunoglobulin domain crossover as a generic approach for the production of bispecific igG antibodies" PNAS USA 108(27):11187-11192 (Jul. 5, 2011).

Seimetz, D., et al., "Development and approval of the trifunctional antibody catumaxomab (anti-EpCAM x anti-CD3) as a target cancer immunotherapy" Cancer Treat Rev 36(6):458-467 (Oct. 1, 2010).

Shantz et al., "Translational regulation of ornithine decarboxylase and other enzymes of the polyamine pathway" Inernational J Biochemistry Cell Biology 31:107-122 (1999).

Sims et al., "A Humanized CD18 Antibody Can Block Function without Cell Destruction" J. Immunol. 151(4):2296-2308 (Aug. 1993).

Skryma et al., "Potassium cnductance in the androgen-sensitive prostate cancer cell line, LNCaP: involvement in cell proliferation" Prostate 33:112-122 ( 1997).

Spiess, C., et al., "Alternative molecular formats and therapeutic applications for bispecific antibodies" Mol Immunol 67( Suppl 2 Pt A):95-106 (Jan. 27, 2015).

Spitler et al., "Cancer Vaccines: The Interferon Analogy" Cancer Biotherapy 10(1):1-3 ( 1995).

Takashi Yamamoto et al., "Six-transmembrane epithelialantigenofthe prostate-1 playsaroleforinvivotumorgrowthvia intercellular communication" Exp Cell Res 319(17):2617-2626 (Aug. 2, 2013).

Tutt et al., "Trispecific F(ab')\\\subscript:3\\\ derivatives that use cooperative signaling via the TCR/CD3 complex and CD2 to activate and redirect resting cytotoxic T cells" J Immunol 147(1):60-69 (Jul. 1991).

Umana, P., et al., "Engineered Glycoforms of an Antineuroblastoma IgG1 with Optimized Antibody-Dependent Cellular Cytotoxic Activity" Nat Biotechnol 17(2):176-180 (Feb. 1, 1999).

Urlaub et al., "Isolation of Chinese hamster cell mutants deficient in dihydrofolate reductase activity" Proc Natl Acad Sci USA 77(7):4216-4220 (Jul. 1980).

Valjakka et al., "Crystal structure of an in vitro affinity- and specificity-matured anti-testosterone Fab in complex with testosterone" J.Biol. Chem 277:44021-44027 ( 2002).

Van Dijk, M., et al., "Human antibodies as next generation therapeutics" Curr Opin Chem Biol 5(4):368-374 (Aug. 1, 2001).

Vitetta et al., "Redesigning nature's poisons to create anti-tumor reagents" Science 238:1098-1104 ( 1987).

Vollmers, H., et al., "The 'early birds': Natural IgM antibodies and immune surveillance" Histol Histopathol 20(3):927-937 (Jul. 1, 2005).

Wang et al., "Tyramide signal amplification method in multiple-label immunofluorescence confocal microscopy" Methods 18(4):459-464 (Aug. 1999).

Winter, G., et al., "Making antibodies by phage display technology" Annu Rev Immunol 12(1):433-455 (Winter 1994).

Wright, A., et al., "Effect of glycosylation on antibody function: implications for genetic engineering" Trends Biotechnol. 15(1):26-32 (Jan. 1, 1997).

Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).

Yang et al., "Murine Six-Transmembrane Epithelial Antigen of The Prostate, Prostate Stem Cell Antigen And Prostate-Specific Membrane Antigen. Prostate-Specific Cell-Surface Antigens Highly Expressed In Prostate Cancer of Transgenic Adenocarcinoma Mouse Prostate Mice" Cancer Res. 61(15):5857-5860 ( 2001).

Yazaki, P. J., et al. Methods in Molecular Biology "Expression of recombinant antibodies in mammalian cell lines" Lo, B.K.C. (ed.), Totowa, NJ:Humana Press, vol. 248:255-268 ( 2004).

Zhao, A., et al., "Phage antibody display libraries: a powerful antibody discover platform for immunotherapy" Crit Rev Biotechnol 36(2):276-289 (Nov. 14, 2014).

(56) References Cited

OTHER PUBLICATIONS

Zhao, Q., et al. Methods in Molecular Biology: Therapeutic Proteins—Methods and Protocols "Chapter 5: Yeast Display of Engineered Antibody Domains" Voynov, Vladimir, ed., New York, NY:Springer, vol. 889:73-84 (Jan. 17, 2012).

* cited by examiner

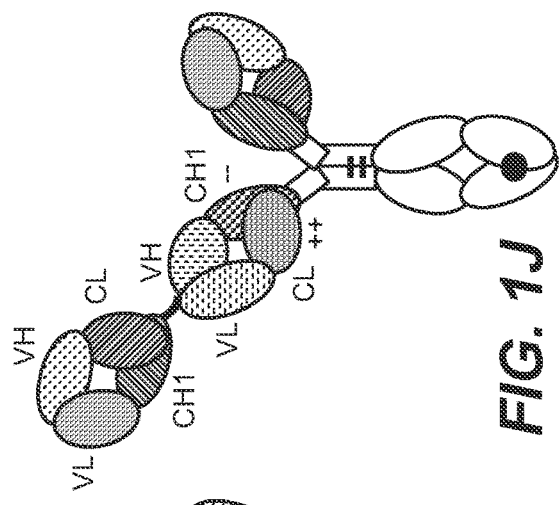
FIG. 1G
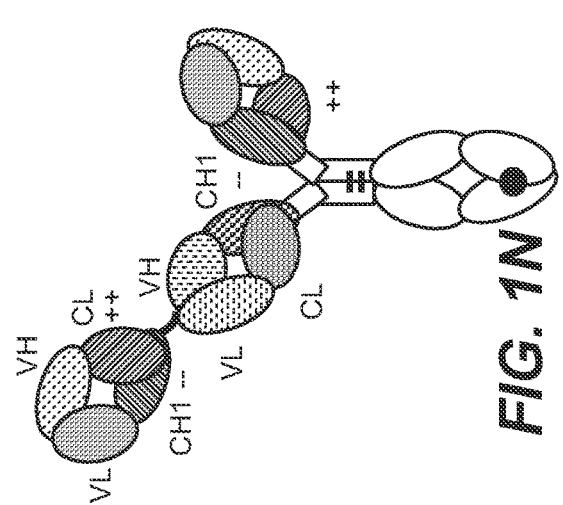
FIG. 1H
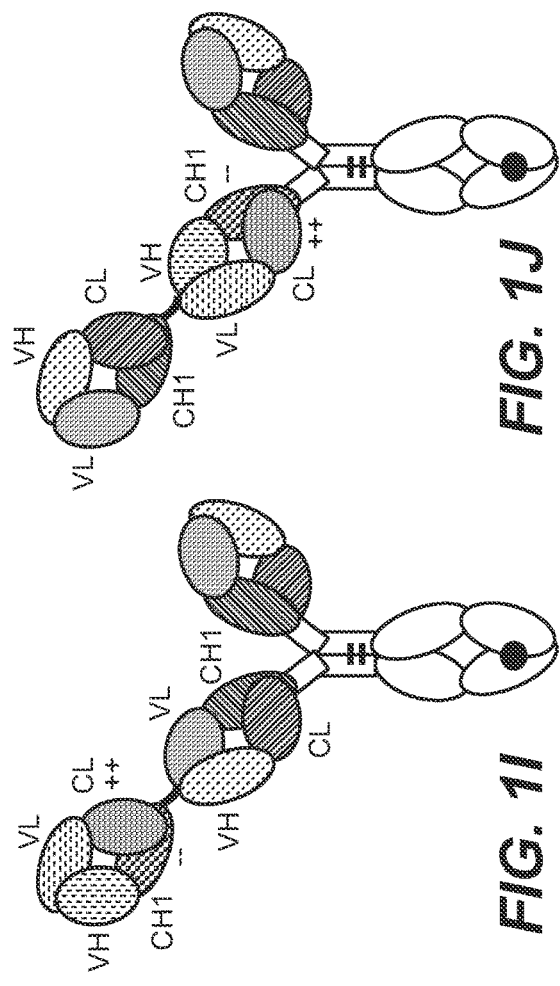
FIG. 1I
FIG. 1J
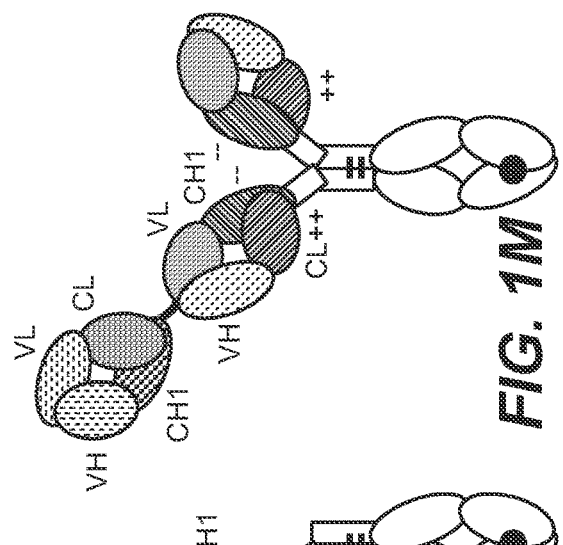
FIG. 1K
FIG. 1L
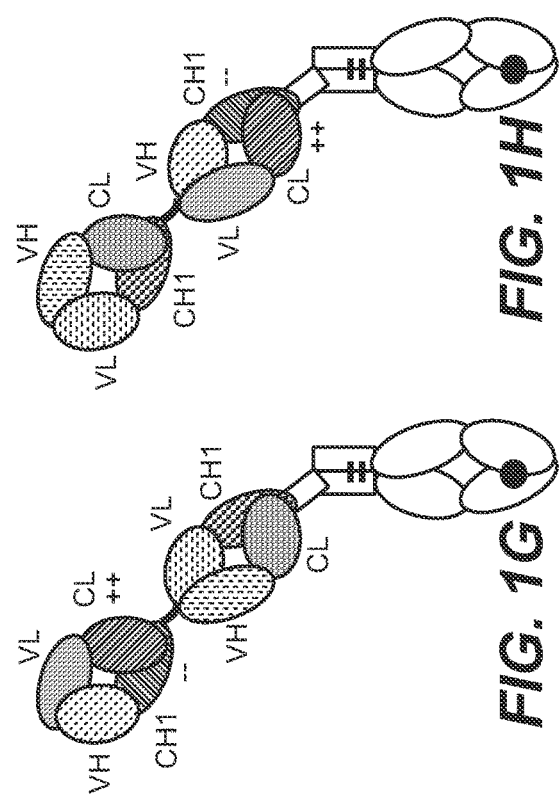
FIG. 1M
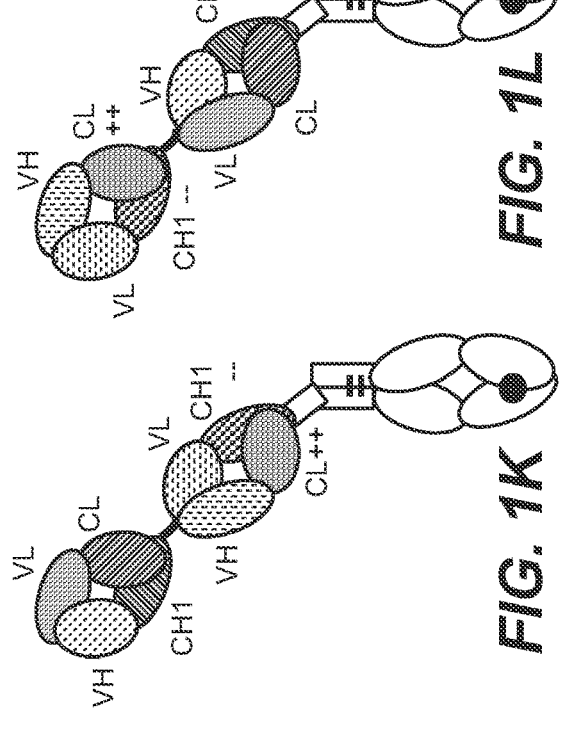
FIG. 1N

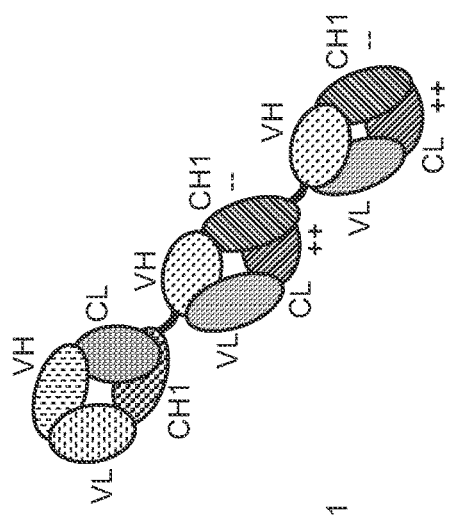
FIG. 1O
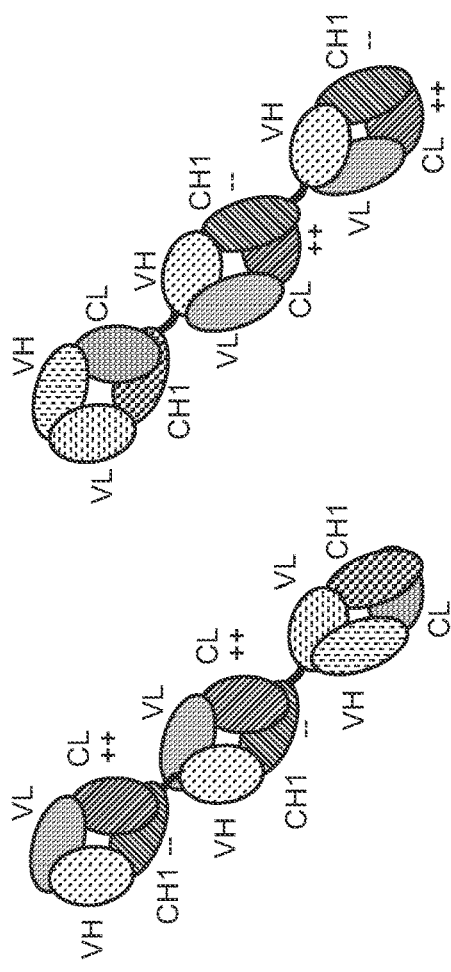
FIG. 1P
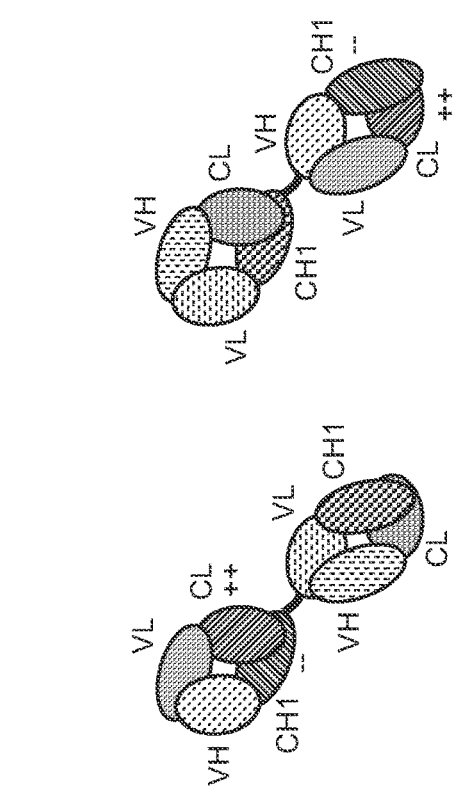
FIG. 1Q
FIG. 1R
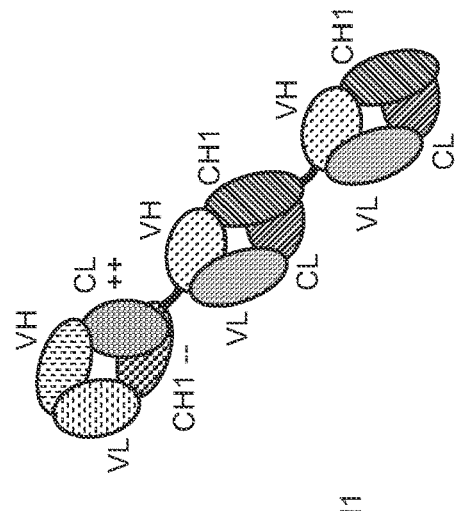
FIG. 1S
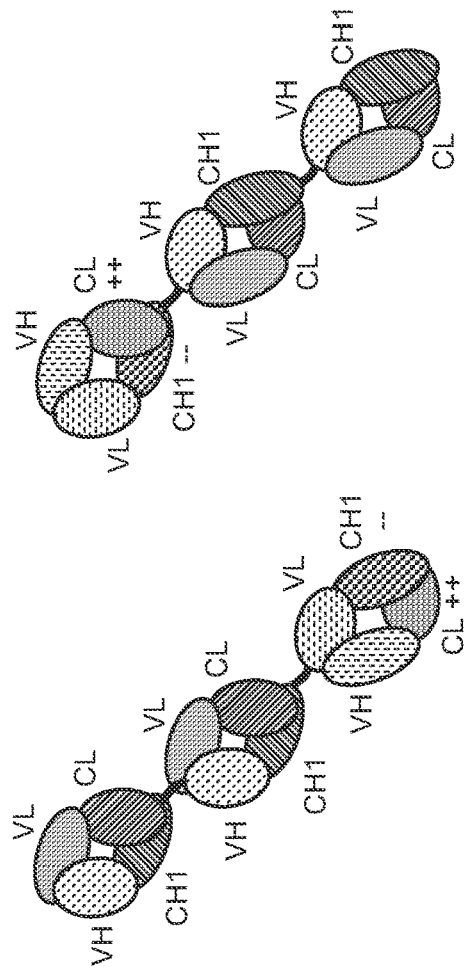
FIG. 1T
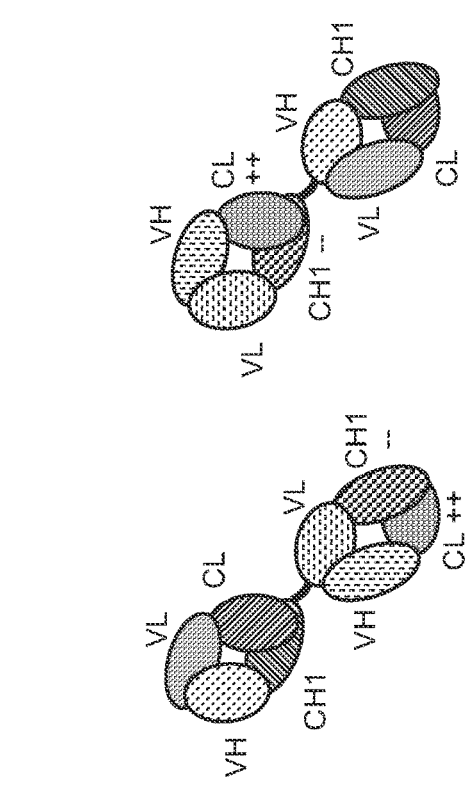
FIG. 1U
FIG. 1V

| Parameter | expected value for an "ideal" lead | Vandortuzumab |
|---|---|---|
| additional Cys or N-Glycosylation sites in CDRs | 0 | 0 |
| Putative Asn/Asp degradation motifs in CDRs | 0 | 3 (N53, N97 & D100a)* |
| Putative Trp oxidation hotspots in CDRs | 0 | 1 (W50) |

*Kabat numeration

FIG. 3A

VH
EVQLVESGGGLVQPGGSLRLSCAVSGYSITSDYAWNWVRQAPGKGLEWVGYISNSGSTS
YNPSLKSRFTISRDTSKNTLYLQMNSLRAEDTAVYYCARERNYDYDDYYAMDYWGQGT
LVTVSS (SEQ ID NO: 10)

VL
DIQMTQSPSSLSASVGDRVTITCKSSQSLLYRSNQKNYLAWYQQKPGKAPKLLIYWAST
RESGVPSRFSGSGSGTDFTLTISSLQPEDFATYYCQQYNYPRTFGQGTKVEIK (SEQ ID NO: 14)

FIG. 3B

SEQUENCE LISTING

```
<160> NUMBER OF SEQ ID NOS: 41

<210> SEQ ID NO 1
<211> LENGTH: 6
<212> TYPE: PRT
<213> ORGANISM: Artificial Sequence
<220> FEATURE:
<223> OTHER INFORMATION: STEAP-1 HCDR1

<400> SEQUENCE: 1

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: STEAP-1 HCDR2

<400> SEQUENCE: 2

Tyr Ile Ser Asn Ser Gly Ser Thr Ser Tyr Asn Pro Ser Leu Lys Ser
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: STEAP-1 HCDR3 (DD)

<400> SEQUENCE: 3

Glu Arg Asn Tyr Asp Tyr Asp Asp Tyr Tyr Ala Met Asp Tyr
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: STEAP-1 HCDR3 (ED)

<400> SEQUENCE: 4

Glu Arg Asn Tyr Asp Tyr Glu Asp Tyr Tyr Ala Met Asp Tyr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: STEAP-1 HCDR3 (DE)
```

<400> SEQUENCE: 5

Glu Arg Asn Tyr Asp Tyr Asp Glu Tyr Tyr Ala Met Asp Tyr
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: STEAP-1 HCDR3 (EE)

<400> SEQUENCE: 6

Glu Arg Asn Tyr Asp Tyr Glu Glu Tyr Tyr Ala Met Asp Tyr
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: STEAP-1 LCDR1

<400> SEQUENCE: 7

Lys Ser Ser Gln Ser Leu Leu Tyr Arg Ser Asn Gln Lys Asn Tyr Leu
1               5                   10                  15
Ala

<210> SEQ ID NO 8
<211> LENGTH: 7
<212> TYPE: PRT
<213> ORGANISM: Artificial Sequence
<220> FEATURE:
<223> OTHER INFORMATION: STEAP-1 LCDR2

<400> SEQUENCE: 8

Trp Ala Ser Thr Arg Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: STEAP-1 LCDR3

<400> SEQUENCE: 9

Gln Gln Tyr Tyr Asn Tyr Pro Arg Thr
1               5

<210> SEQ ID NO 10
<211> LENGTH: 124
<212> TYPE: PRT
<213> ORGANISM: Artificial Sequence
<220> FEATURE:
<223> OTHER INFORMATION: STEAP-1 VH (DD)

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
                20                  25                  30

Tyr Ala Trp Asn Trp Val Arg Gln Ala Pro Gly Lys Gly Leu Glu Trp
            35                  40                  45

```
Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Asn Tyr Asp Tyr Asp Asp Tyr Tyr Tyr Ala Met Asp
                100                 105                 110

Tyr Trp Gly Gln Gly Thr Leu Val Thr Val Ser Ser
            115                 120

<210> SEQ ID NO 11
<211> LENGTH: 124
<212> TYPE: PRT
<213> ORGANISM: Artificial Sequence
<220> FEATURE:
<223> OTHER INFORMATION: STEAP-1 VH (ED)

<400> SEQUENCE: 11

Glu Val Gln Leu Val Glu Ser Gly Gly Gly Leu Val Gln Pro Gly Gly
  1               5                  10                  15

Ser Leu Arg Leu Ser Cys Ala Val Ser Gly Tyr Ser Ile Thr Ser Asp
             20                  25                  30

Tyr Ala Trp Asn Trp Val Arg Gln Ala Pro Gly Lys Gly Leu Glu Trp
         35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Asn Tyr Asp Tyr Glu Asp Tyr Tyr Tyr Ala Met Asp
                100                 105                 110

Tyr Trp Gly Gln Gly Thr Leu Val Thr Val Ser Ser
            115                 120

<210> SEQ ID NO 12
<211> LENGTH: 124
<212> TYPE: PRT
<213> ORGANISM: Artificial Sequence
<220> FEATURE:
<223> OTHER INFORMATION: STEAP-1 VH (DE)

<400> SEQUENCE: 12

Glu Val Gln Leu Val Glu Ser Gly Gly Gly Leu Val Gln Pro Gly Gly
  1               5                  10                  15

Ser Leu Arg Leu Ser Cys Ala Val Ser Gly Tyr Ser Ile Thr Ser Asp
             20                  25                  30

Tyr Ala Trp Asn Trp Val Arg Gln Ala Pro Gly Lys Gly Leu Glu Trp
         35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Asn Tyr Asp Tyr Asp Glu Tyr Tyr Tyr Ala Met Asp
                100                 105                 110
```

```
Tyr Trp Gly Gln Gly Thr Leu Val Thr Val Ser Ser
        115                 120

<210> SEQ ID NO 13
<211> LENGTH: 124
<212> TYPE: PRT
<213> ORGANISM: Artificial Sequence
<220> FEATURE:
<223> OTHER INFORMATION: STEAP-1 VH (EE)

<400> SEQUENCE: 13

Glu Val Gln Leu Val Glu Ser Gly Gly Gly Leu Val Gln Pro Gly Gly
1               5                  10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Glu Glu Tyr Tyr Tyr Ala Met Asp
            100                 105                 110

Tyr Trp Gly Gln Gly Thr Leu Val Thr Val Ser Ser
        115                 120

<210> SEQ ID NO 14
<211> LENGTH: 113
<212> TYPE: PRT
<213> ORGANISM: Artificial Sequence
<220> FEATURE:
<223> OTHER INFORMATION: STEAP-1 VL

<400> SEQUENCE: 14

Asp Ile Gln Met Thr Gln Ser Pro Ser Ser Leu Ser Ala Ser Val Gly
1               5                  10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys

<210> SEQ ID NO 15
<211> LENGTH: 5
<212> TYPE: PRT
<213> ORGANISM: Artificial Sequence
<220> FEATURE:
<223> OTHER INFORMATION: CD3 HCDR1
```

```
<400> SEQUENCE: 15

Thr Tyr Ala Met Asn
1               5

<210> SEQ ID NO 16
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 16

Arg Ile Arg Ser Lys Tyr Asn Asn Tyr Ala Thr Tyr Tyr Ala Asp Ser
1               5                   10                  15

Val Lys Gly

<210> SEQ ID NO 17
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 17

His Gly Asn Phe Gly Asn Ser Tyr Val Ser Trp Phe Ala Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 18

Gly Ser Ser Thr Gly Ala Val Thr Thr Ser Asn Tyr Ala Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 19

Gly Thr Asn Lys Arg Ala Pro
1               5

<210> SEQ ID NO 20
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 20

Ala Leu Trp Tyr Ser Asn Leu Trp Val
1               5

<210> SEQ ID NO 21
<211> LENGTH: 125
<212> TYPE: PRT
<213> ORGANISM: Artificial Sequence
<220> FEATURE:
<223> OTHER INFORMATION: CD3 VH
```

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 22
<211> LENGTH: 109
<212> TYPE: PRT
<213> ORGANISM: Artificial Sequence
<220> FEATURE:
<223> OTHER INFORMATION: CD3 VL

<400> SEQUENCE: 22

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 23
<211> LENGTH: 339
<212> TYPE: PRT
<213> ORGANISM: Homo sapiens

<400> SEQUENCE: 23

```
Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
```

```
            65                  70                  75                  80
    Ile Ala Ser Leu Thr Phe Leu Tyr Thr Leu Leu Arg Glu Val Ile His
                        85                  90                  95

Pro Leu Ala Thr Ser His Gln Gln Tyr Phe Tyr Lys Ile Pro Ile Leu
                    100                 105                 110

Val Ile Asn Lys Val Leu Pro Met Val Ser Ile Thr Leu Leu Ala Leu
                    115                 120                 125

Val Tyr Leu Pro Gly Val Ile Ala Ala Ile Val Gln Leu His Asn Gly
                130                 135                 140

Thr Lys Tyr Lys Lys Phe Pro His Trp Leu Asp Lys Trp Met Leu Thr
    145                 150                 155                 160

Arg Lys Gln Phe Gly Leu Leu Ser Phe Phe Ala Val Leu His Ala
                        165                 170                 175

Ile Tyr Ser Leu Ser Tyr Pro Met Arg Arg Ser Tyr Arg Tyr Lys Leu
                    180                 185                 190

Leu Asn Trp Ala Tyr Gln Gln Val Gln Gln Asn Lys Glu Asp Ala Trp
                195                 200                 205

Ile Glu His Asp Val Trp Arg Met Glu Ile Tyr Val Ser Leu Gly Ile
                210                 215                 220

Val Gly Leu Ala Ile Leu Ala Leu Leu Ala Val Thr Ser Ile Pro Ser
    225                 230                 235                 240

Val Ser Asp Ser Leu Thr Trp Arg Glu Phe His Tyr Ile Gln Ser Lys
                        245                 250                 255

Leu Gly Ile Val Ser Leu Leu Leu Gly Thr Ile His Ala Leu Ile Phe
                    260                 265                 270

Ala Trp Asn Lys Trp Ile Asp Ile Lys Gln Phe Val Trp Tyr Thr Pro
                    275                 280                 285

Pro Thr Phe Met Ile Ala Val Phe Leu Pro Ile Val Val Leu Ile Phe
                290                 295                 300

Lys Ser Ile Leu Phe Leu Pro Cys Leu Arg Lys Lys Ile Leu Lys Ile
    305                 310                 315                 320

Arg His Gly Trp Glu Asp Val Thr Lys Ile Asn Lys Thr Glu Ile Cys
                        325                 330                 335

Ser Gln Leu

<210> SEQ ID NO 24
<211> LENGTH: 207
<212> TYPE: PRT
<213> ORGANISM: Homo sapiens

<400> SEQUENCE: 24

Met Gln Ser Gly Thr His Trp Arg Val Leu Gly Leu Cys Leu Leu Ser
    1               5                   10                  15

Val Gly Val Trp Gly Gln Asp Gly Asn Glu Glu Met Gly Gly Ile Thr
                    20                  25                  30

Gln Thr Pro Tyr Lys Val Ser Ile Ser Gly Thr Thr Val Ile Leu Thr
                35                  40                  45

Cys Pro Gln Tyr Pro Gly Ser Glu Ile Leu Trp Gln His Asn Asp Lys
                50                  55                  60

Asn Ile Gly Gly Asp Glu Asp Asp Lys Asn Ile Gly Ser Asp Glu Asp
    65                  70                  75                  80

His Leu Ser Leu Lys Glu Phe Ser Glu Leu Glu Gln Ser Gly Tyr Tyr
                        85                  90                  95

Val Cys Tyr Pro Arg Gly Ser Lys Pro Glu Asp Ala Asn Phe Tyr Leu
```

```
            100                 105                 110
Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 25
<211> LENGTH: 198
<212> TYPE: PRT
<213> ORGANISM: Macaca fascicularis

<400> SEQUENCE: 25

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
    130                 135                 140                 Lys

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
        195

<210> SEQ ID NO 26
<211> LENGTH: 452
<212> TYPE: PRT
<213> ORGANISM: Artificial Sequence
<220> FEATURE:
<223> OTHER INFORMATION: Molecule A (STEAP-1 VH-CH1(EE)-Fc(knob,
      PGLALA))

<400> SEQUENCE: 26

Glu Val Gln Leu Val Glu Ser Gly Gly Gly Leu Val Gln Pro Gly Gly
```

-continued

```
1               5                   10                  15
Ser Leu Arg Leu Ser Cys Ala Val Ser Gly Tyr Ser Ile Thr Ser Asp
                20                  25                  30
Tyr Ala Trp Asn Trp Val Arg Gln Ala Pro Gly Lys Gly Leu Glu Trp
                35                  40                  45
Val Gly Tyr Ile Ser Asn Ser Gly Ser Thr Ser Tyr Asn Pro Ser Leu
            50                  55                  60
Lys Ser Arg Phe Thr Ile Ser Arg Asp Thr Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Arg Asn Tyr Asp Tyr Asp Asp Tyr Tyr Ala Met Asp
                100                 105                 110
Tyr Trp Gly Gln Gly Thr Leu Val Thr Val Ser Ala Ser Thr Lys
                115                 120                 125
Gly Pro Ser Val Phe Pro Leu Ala Pro Ser Ser Lys Ser Thr Ser Gly
        130                 135                 140
Gly Thr Ala Ala Leu Gly Cys Leu Val Glu Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
            195                 200                 205
Val Asn His Lys Pro Ser Asn Thr Lys Val Asp Glu Lys Val Glu Pro
        210                 215                 220
Lys Ser Cys Asp Lys Thr His Thr Cys Pro Pro Cys Pro Ala Pro Glu
225                 230                 235                 240
Ala Ala Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
            275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Gly
                325                 330                 335
Ala Pro Ile Glu Lys Thr Ile Ser Lys Ala Lys Gly Gln Pro Arg Glu
                340                 345                 350
Pro Gln Val Cys Thr Leu Pro Pro Ser Arg Asp Glu Leu Thr Lys Asn
                355                 360                 365
Gln Val Ser Leu Ser Cys Ala Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Val Ser Lys
                405                 410                 415
Leu Thr Val Asp Lys Ser Arg Trp Gln Gln Gly Asn Val Phe Ser Cys
                420                 425                 430
```

-continued

Ser Val Met His Glu Ala Leu His Asn His Tyr Thr Gln Lys Ser Leu
        435                 440                 445

Ser Leu Ser Pro
    450

<210> SEQ ID NO 27
<211> LENGTH: 677
<212> TYPE: PRT
<213> ORGANISM: Artificial Sequence
<220> FEATURE:
<223> OTHER INFORMATION: Molecule A (STEAP-1 VH-CH1(EE)-CD3
      VL-CH1-Fc(knob, PGLALA))

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Asp Tyr Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Glu Lys Val Glu Pro
    210                 215                 220

Lys Ser Cys Asp Gly Gly Gly Gly Ser Gly Gly Gly Gly Ser Gln Ala
225                 230                 235                 240

Val Val Thr Gln Glu Pro Ser Leu Thr Val Ser Pro Gly Gly Thr Val
                245                 250                 255

Thr Leu Thr Cys Gly Ser Ser Thr Gly Ala Val Thr Thr Ser Asn Tyr
            260                 265                 270

Ala Asn Trp Val Gln Glu Lys Pro Gly Gln Ala Phe Arg Gly Leu Ile
        275                 280                 285

Gly Gly Thr Asn Lys Arg Ala Pro Gly Thr Pro Ala Arg Phe Ser Gly
    290                 295                 300

Ser Leu Leu Gly Gly Lys Ala Ala Leu Thr Leu Ser Gly Ala Gln Pro
305                 310                 315                 320

Glu Asp Glu Ala Glu Tyr Tyr Cys Ala Leu Trp Tyr Ser Asn Leu Trp

```
            325                 330                 335
Val Phe Gly Gly Gly Thr Lys Leu Thr Val Leu Ser Ser Ala Ser Thr
            340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
            370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
                420                 425                 430

Asn Val Asn His Lys Pro Ser Asn Thr Lys Val Asp Lys Lys Val Glu
                435                 440                 445

Pro Lys Ser Cys Asp Lys Thr His Thr Cys Pro Pro Cys Pro Ala Pro
            450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                    485                 490                 495

Asp Val Ser His Glu Asp Pro Glu Val Lys Phe Asn Trp Tyr Val Asp
                500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                    565                 570                 575

Glu Pro Gln Val Tyr Thr Leu Pro Pro Cys Arg Asp Glu Leu Thr Lys
                580                 585                 590

Asn Gln Val Ser Leu Trp Cys Leu Val Lys Gly Phe Tyr Pro Ser Asp
            595                 600                 605

Ile Ala Val Glu Trp Glu Ser Asn Gly Gln Pro Glu Asn Asn Tyr Lys
            610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                    645                 650                 655

Cys Ser Val Met His Glu Ala Leu His Asn His Tyr Thr Gln Lys Ser
                660                 665                 670

Leu Ser Leu Ser Pro
                675

<210> SEQ ID NO 28
<211> LENGTH: 452
<212> TYPE: PRT
<213> ORGANISM: Artificial Sequence
<220> FEATURE:
<223> OTHER INFORMATION: Molecule B (STEAP-1 VH-CH1(EE)-Fc(knob,
      PGLALA))

<400> SEQUENCE: 28
```

-continued

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Glu Asp Tyr Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Glu Lys Val Glu Pro
210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
            325                 330                 335

Ala Pro Ile Glu Lys Thr Ile Ser Lys Ala Lys Gly Gln Pro Arg Glu
        340                 345                 350

Pro Gln Val Cys Thr Leu Pro Pro Ser Arg Asp Glu Leu Thr Lys Asn
    355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
            405                 410                 415

Leu Thr Val Asp Lys Ser Arg Trp Gln Gln Gly Asn Val Phe Ser Cys

```
                    420                 425                 430

Ser Val Met His Glu Ala Leu His Asn His Tyr Thr Gln Lys Ser Leu
        435                 440                 445

Ser Leu Ser Pro
    450

<210> SEQ ID NO 29
<211> LENGTH: 677
<212> TYPE: PRT
<213> ORGANISM: Artificial Sequence
<220> FEATURE:
<223> OTHER INFORMATION: Molecule B (STEAP-1 VH-CH1(EE)-CD3
      VL-CH1-Fc(knob, PGLALA))

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Glu Asp Tyr Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Gly Gly Gly Ser Gly Gly Gly Ser Gln Ala
225                 230                 235                 240

Val Val Thr Gln Glu Pro Ser Leu Thr Val Ser Pro Gly Gly Thr Val
                245                 250                 255

Thr Leu Thr Cys Gly Ser Ser Thr Gly Ala Val Thr Thr Ser Asn Tyr
            260                 265                 270

Ala Asn Trp Val Gln Glu Lys Pro Gly Gln Ala Phe Arg Gly Leu Ile
        275                 280                 285

Gly Gly Thr Asn Lys Arg Ala Pro Gly Thr Pro Ala Arg Phe Ser Gly
    290                 295                 300

Ser Leu Leu Gly Gly Lys Ala Ala Leu Thr Leu Ser Gly Ala Gln Pro
305                 310                 315                 320
```

```
Glu Asp Glu Ala Glu Tyr Tyr Cys Ala Leu Trp Tyr Ser Asn Leu Trp
                325                 330                 335

Val Phe Gly Gly Gly Thr Lys Leu Thr Val Leu Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Lys Asp Tyr Phe Pro Glu
    370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
    450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
    530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Tyr Thr Leu Pro Pro Cys Arg Asp Glu Leu Thr Lys
            580                 585                 590

Asn Gln Val Ser Leu Trp Cys Leu Val Lys Gly Phe Tyr Pro Ser Asp
        595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro
        675

<210> SEQ ID NO 30
<211> LENGTH: 452
<212> TYPE: PRT
<213> ORGANISM: Artificial Sequence
<220> FEATURE:
<223> OTHER INFORMATION: Molecule C (STEAP-1 VH-CH1(EE)-Fc(knob,
      PGLALA))

<400> SEQUENCE: 30
```

-continued

```
Glu Val Gln Leu Val Glu Ser Gly Gly Gly Leu Val Gln Pro Gly Gly
1               5                   10                  15
Ser Leu Arg Leu Ser Cys Ala Val Ser Gly Tyr Ser Ile Thr Ser Asp
            20                  25                  30
Tyr Ala Trp Asn Trp Val Arg Gln Ala Pro Gly Lys Gly Leu Glu Trp
        35                  40                  45
Val Gly Tyr Ile Ser Asn Ser Gly Ser Thr Ser Tyr Asn Pro Ser Leu
    50                  55                  60
Lys Ser Arg Phe Thr Ile Ser Arg Asp Thr Ser Lys Asn Thr Leu Tyr
65              70                  75                  80
Leu Gln Met Asn Ser Leu Arg Ala Glu Asp Thr Ala Val Tyr Tyr Cys
            85                  90                  95
Ala Arg Glu Arg Asn Tyr Asp Tyr Asp Glu Tyr Tyr Ala Met Asp
        100                 105                 110
Tyr Trp Gly Gln Gly Thr Leu Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Glu Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Glu Lys Val Glu Pro
    210                 215                 220
Lys Ser Cys Asp Lys Thr His Thr Cys Pro Pro Cys Pro Ala Pro Glu
225                 230                 235                 240
Ala Ala Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Gly
                325                 330                 335
Ala Pro Ile Glu Lys Thr Ile Ser Lys Ala Lys Gly Gln Pro Arg Glu
            340                 345                 350
Pro Gln Val Cys Thr Leu Pro Pro Ser Arg Asp Glu Leu Thr Lys Asn
        355                 360                 365
Gln Val Ser Leu Ser Cys Ala Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Val Ser Lys
                405                 410                 415
```

```
Leu Thr Val Asp Lys Ser Arg Trp Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro
            450

<210> SEQ ID NO 31
<211> LENGTH: 677
<212> TYPE: PRT
<213> ORGANISM: Artificial Sequence
<220> FEATURE:
<223> OTHER INFORMATION: Molecule C (STEAP-1 VH-CH1(EE)-CD3
      VL-CH1-Fc(knob, PGLALA))

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
            35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Arg Glu Arg Asn Tyr Asp Tyr Asp Glu Tyr Tyr Tyr Ala Met Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Glu Lys Val Glu Pro
    210                 215                 220

Lys Ser Cys Asp Gly Gly Gly Ser Gly Gly Gly Ser Gln Ala
225                 230                 235                 240

Val Val Thr Gln Glu Pro Ser Leu Thr Val Ser Pro Gly Gly Thr Val
            245                 250                 255

Thr Leu Thr Cys Gly Ser Ser Thr Gly Ala Val Thr Thr Ser Asn Tyr
            260                 265                 270

Ala Asn Trp Val Gln Glu Lys Pro Gly Gln Ala Phe Arg Gly Leu Ile
            275                 280                 285

Gly Gly Thr Asn Lys Arg Ala Pro Gly Thr Pro Ala Arg Phe Ser Gly
            290                 295                 300

Ser Leu Leu Gly Gly Lys Ala Ala Leu Thr Leu Ser Gly Ala Gln Pro
305                 310                 315                 320
```

Glu Asp Glu Ala Glu Tyr Tyr Cys Ala Leu Trp Tyr Ser Asn Leu Trp
                325                 330                 335

Val Phe Gly Gly Gly Thr Lys Leu Thr Val Leu Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Lys Asp Tyr Phe Pro Glu
    370                 375                 380

Pro Val Thr Val Ser Trp Asn Ser Gly Ala Leu Thr Ser Gly Val His
385                 390                 395                 400

Thr Phe Pro Ala Val Leu Gln Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
        435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
    530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Tyr Thr Leu Pro Pro Cys Arg Asp Glu Leu Thr Lys
            580                 585                 590

Asn Gln Val Ser Leu Trp Cys Leu Val Lys Gly Phe Tyr Pro Ser Asp
        595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro
        675

<210> SEQ ID NO 32
<211> LENGTH: 452
<212> TYPE: PRT
<213> ORGANISM: Artificial Sequence
<220> FEATURE:
<223> OTHER INFORMATION: Molecule D (STEAP-1 VH-CH1(EE)-Fc(knob,
      PGLALA))

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Glu Tyr Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Glu Lys Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Gly
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Asp Glu Leu Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

```
Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro
        450

<210> SEQ ID NO 33
<211> LENGTH: 677
<212> TYPE: PRT
<213> ORGANISM: Artificial Sequence
<220> FEATURE:
<223> OTHER INFORMATION: Molecule D (STEAP-1 VH-CH1(EE)-CD3
      VL-CH1-Fc(knob, PGLALA))

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Glu Glu Tyr Tyr Tyr Ala Met Asp
                100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Glu Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Glu Lys Val Glu Pro
    210                 215                 220

Lys Ser Cys Asp Gly Gly Gly Ser Gly Gly Gly Ser Gln Ala
225                 230                 235                 240

Val Val Thr Gln Glu Pro Ser Leu Thr Val Ser Pro Gly Gly Thr Val
                245                 250                 255

Thr Leu Thr Cys Gly Ser Ser Thr Gly Ala Val Thr Thr Ser Asn Tyr
            260                 265                 270

Ala Asn Trp Val Gln Glu Lys Pro Gly Gln Ala Phe Arg Gly Leu Ile
        275                 280                 285

Gly Gly Thr Asn Lys Arg Ala Pro Gly Thr Pro Ala Arg Phe Ser Gly
    290                 295                 300

Ser Leu Leu Gly Gly Lys Ala Ala Leu Thr Leu Ser Gly Ala Gln Pro
```

```
            305                 310                 315                 320
Glu Asp Glu Ala Glu Tyr Tyr Cys Ala Leu Trp Tyr Ser Asn Leu Trp
                    325                 330                 335

Val Phe Gly Gly Gly Thr Lys Leu Thr Val Leu Ser Ser Ala Ser Thr
                340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
        370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Leu Gly Thr Gln Thr Tyr Ile Cys
                420                 425                 430

Asn Val Asn His Lys Pro Ser Asn Thr Lys Val Asp Lys Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
        530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Tyr Thr Leu Pro Pro Cys Arg Asp Glu Leu Thr Lys
                580                 585                 590

Asn Gln Val Ser Leu Trp Cys Leu Val Lys Gly Phe Tyr Pro Ser Asp
            595                 600                 605

Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
                660                 665                 670

Leu Ser Leu Ser Pro
        675

<210> SEQ ID NO 34
<211> LENGTH: 220
<212> TYPE: PRT
<213> ORGANISM: Artificial Sequence
<220> FEATURE:
<223> OTHER INFORMATION: Molecule A-D (STEAP-1 VL-CL(RK))
```

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Arg Lys Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 35
<211> LENGTH: 232
<212> TYPE: PRT
<213> ORGANISM: Artificial Sequence
<220> FEATURE:
<223> OTHER INFORMATION: Molecule A-D (CD3 VH-CL)

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys

```
Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
            210                 215                 220

Lys Ser Phe Asn Arg Gly Glu Cys
225                 230

<210> SEQ ID NO 36
<211> LENGTH: 225
<212> TYPE: PRT
<213> ORGANISM: Homo sapiens

<400> SEQUENCE: 36

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225

<210> SEQ ID NO 37
<211> LENGTH: 10
<212> TYPE: PRT
<213> ORGANISM: Artificial Sequence
<220> FEATURE:
```

<223> OTHER INFORMATION: linker

<400> SEQUENCE: 37

Gly Gly Gly Gly Ser Gly Gly Gly Gly Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: linker

<400> SEQUENCE: 38

Asp Gly Gly Gly Ser Gly Gly Gly Gly Ser
1               5                   10

<210> SEQ ID NO 39
<211> LENGTH: 107
<212> TYPE: PRT
<213> ORGANISM: Homo sapiens

<400> SEQUENCE: 39

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 40
<211> LENGTH: 105
<212> TYPE: PRT
<213> ORGANISM: Homo sapiens

<400> SEQUENCE: 40

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

```
<210> SEQ ID NO 41
<211> LENGTH: 328
<212> TYPE: PRT
<213> ORGANISM: Homo sapiens

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

ANTIBODIES BINDING TO STEAP-1

CROSS REFERENCE TO RELATED APPLICATIONS

This application is a continuation of U.S. application Ser. No. 16/587,606, filed Sep. 30, 2019, which is a continuation of International Application No. PCT/EP2018/058043, filed Mar. 29, 2018, the entire contents of which are incorporated herein by reference, and which claims benefit under 35 U.S.C. § 119 to European Patent Application No. 17164466.9, filed Apr. 3, 2017.

SEQUENCE LISTING

This application contains a Sequence Listing which has been submitted electronically via EFS-Web in ASCII format and is hereby incorporated by reference in its entirety. Said ASCII copy, created on Aug. 10, 2021, is named "P34188-US-1_Sequence_Listing.txt" and is 68,947 bytes in size.

FIELD OF THE INVENTION

The present invention generally relates to antibodies that bind to STEAP-1, including bispecific antigen binding molecules e.g. for activating T cells. In addition, the present invention relates to polynucleotides encoding such antibodies, and vectors and host cells comprising such polynucleotides. The invention further relates to methods for producing the antibodies, and to methods of using them in the treatment of disease.

BACKGROUND

STEAP-1 (six-transmembrane epithelial antigen of the prostate-1) is a 339 amino acid cell surface protein which in normal tissues is expressed predominantly in prostate cells. STEAP-1 protein expression is maintained at high levels across various states of prostate cancer, and STEAP-1 is also highly over-expressed in other human cancers such as lung and colon. The expression profile of STEAP-1 in normal and cancer tissues suggested its potential use as a therapeutic target, e.g. for immunotherapy. WO 2008/052187 reports anti-STEAP-1 antibodies and immunoconjugates thereof. A STEAP-1/CD3 (scFv)$_2$ bispecific antibody is described in WO 2014/165818. There exists a need for additional drugs to treat various cancers and metastases of cancers in the prostate, lung and colon. Particularly useful drugs for this purpose include antibodies that bind STEAP-1, in particular bispecific antibodies that bind STEAP-1 on target cells and an activating T cell antigen such as CD3 on T-cells. The simultaneous binding of such an antibody to both of its targets will force a temporary interaction between target cell and T cell, causing activation of any cytotoxic T cell and subsequent lysis of the target cell.

For therapeutic purposes, an important requirement that antibodies have to fulfill is sufficient stability both in vitro (for storage of the drug) an in vivo (after administration to the patient).

Modifications like asparagine deamidation, aspartate isomerization, succinimide formation, and tryptophane oxidation are typical degradations for recombinant antibodies and can affect both in vitro stability and in vivo biological functions.

The present invention provides novel antibodies, including bispecific antibodies, that bind STEAP-1 and are resistant to degradation by e.g. succinimide formation and thus show good stability. The (bispecific) antibodies provided further combine good efficacy and producibility with low toxicity and favorable pharmacokinetic properties.

SUMMARY OF THE INVENTION

The present inventors have developed a novel antibody with unexpected, improved properties, that binds to STEAP-1. In particular, the antibody is resistant to degradation e.g. by succinimide formation, and thus particularly stable as required for therapeutic purposes. Furthermore, the inventors have developed bispecific antigen binding molecules that bind to STEAP-1 and an activating T cell antigen, incorporating the novel STEAP-1 antibody.

Thus, in a first aspect the present invention provides an antibody that binds to STEAP-1, wherein the antibody shows less than about 5% succinimide degradation after 4 weeks at pH 7.4, 37° C., and/or less than about 10% succinimide degradation after 4 weeks at pH 6.0, 40° C., as determined by mass spectrometry.

In a further aspect the present invention provides an antibody that binds to STEAP-1, wherein the antibody comprises a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9. In one embodiment, the VH comprises an amino acid sequence that is at least about 95%, 96%, 97%, 98%, 99% or 100% identical to an amino acid sequence selected from the group of SEQ ID NO: 11, SEQ ID NO: 12 and SEQ ID NO: 13, and the VL comprises an amino acid sequence that is at least about 95%, 96%, 97%, 98%, 99% or 100% identical to the amino acid sequence of SEQ ID NO: 14. In one embodiment, the antibody is an IgG, particularly an IgG$_1$, antibody. In one embodiment, the antibody is a full-length antibody. In another embodiment, the antibody is an antibody fragment selected from the group of an Fv molecule, a scFv molecule, a Fab molecule, and a F(ab')$_2$ molecule. In one embodiment, the antibody is a multispecific antibody.

The invention also provides a bispecific antigen binding molecule, comprising (a) a first antigen binding moiety that binds to a first antigen, wherein the first antigen is STEAP-1 and the first antigen binding moiety comprises a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9, and (b) a second antigen binding moiety which specifically binds to a second antigen. In one embodiment, the VH of the first antigen binding moiety comprises an amino acid sequence that is at least about 95%, 96%, 97%, 98%, 99% or 100% identical to an amino acid sequence selected from the group of SEQ ID NO: 11, SEQ ID NO: 12 and SEQ ID NO: 13, and the VL of the first antigen binding moiety comprises an amino acid sequence that is at least about 95%, 96%, 97%, 98%, 99% or 100% identical to the amino acid sequence of SEQ ID NO: 14. In one embodiment, the second antigen is CD3, particularly CD3ε. In one embodiment, the second antigen binding moiety comprises a VH comprising a HCDR 1 of SEQ ID NO: 15, a HCDR 2 of SEQ ID NO: 16, and a HCDR 3 of SEQ ID NO: 17, and a VL comprising a LCDR 1 of SEQ ID NO: 18, a LCDR 2 of SEQ ID NO: 19 and a LCDR 3 of SEQ ID NO: 20. In one embodiment, the VH of the second antigen binding moiety comprises an amino acid sequence that is at least about 95%, 96%, 97%, 98%, 99% or 100% identical to the amino acid sequence of SEQ ID NO: 21, and the VL of the second antigen binding moiety comprises an amino acid sequence that is at least about 95%, 96%, 97%, 98%, 99% or 100% identical to the amino acid sequence of SEQ ID NO: 22. In one embodiment, the first and/or the second antigen binding moiety is a Fab molecule. In one embodiment, the second antigen binding moiety is a Fab molecule wherein the variable domains VL and VH or the constant domains CL and CH1, particularly the variable domains VL and VH, of the Fab light chain and the Fab heavy chain are replaced by each other. In one embodiment, the first antigen binding moiety is a Fab molecule wherein in the constant domain the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index). In one embodiment, the first and the second antigen binding moiety are fused to each other, optionally via a peptide linker. In one embodiment, the first and the second antigen binding moiety are each a Fab molecule and either (i) the second antigen binding moiety is fused at the C-terminus of the Fab heavy chain to the N-terminus of the Fab heavy chain of the first antigen binding moiety, or (ii) the first antigen binding moiety is fused at the C-terminus of the Fab heavy chain to the N-terminus of the Fab heavy chain of the second antigen binding moiety. In one embodiment, the bispecific antigen binding molecule comprises a third antigen binding moiety. In one embodiment, the third antigen moiety is identical to the first antigen binding moiety. In one embodiment, the bispecific antigen binding molecule comprises an Fc domain composed of a first and a second subunit. In one embodiment, the first, the second and, where present, the third antigen binding moiety are each a Fab molecule; and either (i) the second antigen binding moiety is fused at the C-terminus of the Fab heavy chain to the N-terminus of the Fab heavy chain of the first antigen binding moiety and the first antigen binding moiety is fused at the C-terminus of the Fab heavy chain to the N-terminus of the first subunit of the Fc domain, or (ii) the first antigen binding moiety is fused at the C-terminus of the Fab heavy chain to the N-terminus of the Fab heavy chain of the second antigen binding moiety and the second antigen binding moiety is fused at the C-terminus of the Fab heavy chain to the N-terminus of the first subunit of the Fc domain; and the third antigen binding moiety, where present, is fused at the C-terminus of the Fab heavy chain to the N-terminus of the second subunit of the Fc domain. In one embodiment, the Fc domain is an IgG, particularly an IgG$_1$, Fc domain. In one embodiment, the Fc domain is a human Fc domain. In one embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. In one embodiment, the Fc domain comprises one or more amino acid substitution that reduces binding to an Fc receptor and/or effector function.

According to another aspect of the invention there is provided one or more isolated polynucleotide(s) encoding an antibody or bispecific antigen binding molecule of the invention. The invention further provides one or more expression vector(s) comprising the isolated polynucleotide(s) of the invention, and a host cell comprising the isolated polynucleotide(s) or the expression vector(s) of the invention. In some embodiments the host cell is a eukaryotic cell, particularly a mammalian cell.

In another aspect is provided a method of producing an antibody that binds to STEAP-1, comprising the steps of a) culturing the host cell of the invention under conditions suitable for the expression of the antibody and b) recovering the antibody. The invention also encompasses an antibody that binds to STEAP-1 produced by the method of the invention.

The invention further provides a pharmaceutical composition comprising the antibody or bispecific antigen binding molecule of the invention and a pharmaceutically acceptable carrier.

Also encompassed by the invention are methods of using the antibody, bispecific antigen binding molecule and pharmaceutical composition of the invention. In one aspect the invention provides an antibody, bispecific antigen binding molecule or pharmaceutical composition according to the invention for use as a medicament. In one aspect is provided an antibody, bispecific antigen binding molecule or pharmaceutical composition according to the invention for use in the treatment of a disease. In a specific embodiment the disease is cancer.

Also provided is the use of an antibody or bispecific antigen binding molecule according to the invention in the manufacture of a medicament for the treatment of a disease; as well as a method of treating a disease in an individual, comprising administering to said individual a therapeutically effective amount of a composition comprising the antibody or bispecific antigen binding molecule according to the invention in a pharmaceutically acceptable form. In a specific embodiment the disease is cancer. In any of the above embodiments the individual preferably is a mammal, particularly a human.

BRIEF DESCRIPTION OF THE DRAWINGS

(FIG. 1A, FIG. 1D) Illustration of the "1+1 CrossMab" molecule. (FIG. 1G, FIG. 1K) Illustration of the "1+1 IgG Crossfab" molecule with alternative order of Crossfab and Fab components ("inverted"). (FIG. 1H, FIG. 1L) Illustration of the "1+1 IgG Crossfab" molecule. (FIG. 1I, FIG. 1M) Illustration of the "2+1 IgG Crossfab" molecule with two CrossFabs. (FIG. 1J, FIG. 1N) Illustration of the "2+1 IgG Crossfab" molecule with two CrossFabs and alternative order of Crossfab and Fab components ("inverted"). (FIG. 1O, FIG. 1S) Illustration of the "Fab-Crossfab" molecule. (FIG. 1P, FIG. 1T) Illustration of the "Crossfab-Fab" molecule. (FIG. 1Q, FIG. 1U) Illustration of the "(Fab)$_2$-Crossfab" molecule. (FIG. 1R, FIG. 1V) Illustration of the "Crossfab-(Fab)$_2$" molecule. (FIG. 1X, FIG. 1Z) Illustration of the "(Crossfab)$_2$-Fab" molecule. Black dot: optional modification in the Fc domain promoting heterodimerization. ++, --: amino acids of opposite charges optionally introduced in the CH1 and CL domains. Crossfab molecules are depicted as comprising an exchange of VH and VL regions, but may—in embodiments wherein no charge modifications are introduced in CH1 and CL domains—alternatively comprise an exchange of the CH1 and CL domains.

FIG. 3A-FIG. 3J. Sequence analysis of the variable domains of vandortuzumab. (FIG. 3A) Prediction of hotspot positions in the sequence. (FIG. 3B) Annotation of the CDR regions and the predicted hotspots in the variable domain sequences of vandortuzumab.

DETAILED DESCRIPTION OF THE INVENTION

Definitions

Figure 1A:
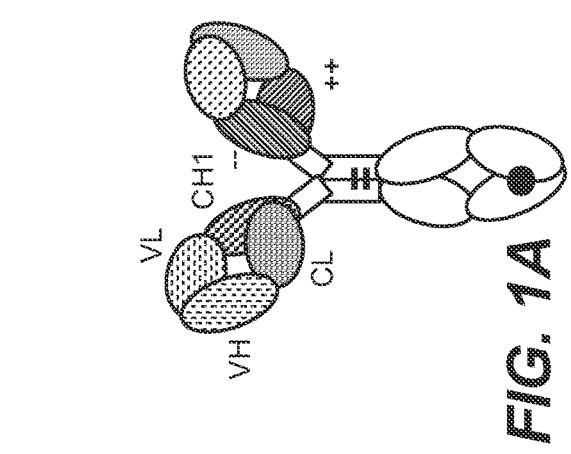
FIG. 1A-FIG. 1Z. Exemplary configurations of the bispecific antigen binding molecules of the invention.

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives. e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope", and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. STEAP-1, CD3) can be any native form of the proteins from any vertebrate source, including mammals such as primates (e.g. humans), non-human primates (e.g. cynomolgus monkeys) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein. e.g. splice variants or allelic variants. An exemplary human protein useful as antigen is CD3, particularly the epsilon subunit of CD3 (see UniProt no. P07766 (version 185), NCBI RefSeq no. NP_000724.1, SEQ ID NO: 24 for the human sequence; or UniProt no. Q95LI5 (version 69), NCBI GenBank no. BAB71849.1, SEQ ID NO: 25 for the cynomolgus [Macaca fascicularis] sequence), or STEAP-1 (six-transmembrane epithelial antigen of prostate 1; see UniProt no. Q9UHE8 (version 137): NCBI RefSeq no. NP_036581.1, SEQ ID NO: 23 for the human sequence). In certain embodiments the antibody or bispecific antigen binding molecule of the invention binds to an epitope of CD3 or STEAP-1 that is conserved among the CD3 or STEAP-1 antigens from different species. In particular embodiments, the antibody or bispecific antigen binding molecule of the invention binds to human STEAP-1.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity, the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 144), NCBI RefSeq no. NP_000724.1, SEQ ID NO. 24 for the human sequence; or UniProt no. Q95LI5 (version 49), NCBI GenBank no. BAB71849.1, SEQ ID NO: 25 for the cynomolgus [Macaca fascicularis] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. Suitable assays to measure T cell activation are known in the art and described herein.

A "target cell antigen" as used herein refers to an antigenic determinant presented on the surface of a target cell, for example a cell in a tumor such as a cancer cell or a cell of the tumor stroma. In a particular embodiment, the target cell antigen is STEAP-1, particularly human STEAP-1.

As used herein, the terms "first", "second" or "third" with respect to Fab molecules etc., are used for convenience of distinguishing when there is more than one of each type of moiety. Use of these terms is not intended to confer a specific order or orientation of the bispecific antigen binding molecule unless explicitly so stated.

By "fused" is meant that the components (e.g. a Fab molecule and an Fc domain subunit) are linked by peptide bonds, either directly or via one or more peptide linkers.

A "Fab molecule" refers to a protein consisting of the VH and CH1 domain of the heavy chain (the "Fab heavy chain") and the VL and CL domain of the light chain (the "Fab light chain") of an immunoglobulin.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 daltons, consisting of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or µ (IgM), some of which may be further divided into subtypes, e.g. $γ_1$ ($IgG_1$), $γ_2$ ($IgG_2$), $γ_3$ ($IgG_3$), $γ_4$ ($IgG_4$), $α_1$ ($IgA_1$) and $α_2$ ($IgA_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity.

The term "monoclonal antibody" as used herein refers to an antibody obtained from a population of substantially homogeneous antibodies, i.e. the individual antibodies comprised in the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "isolated" antibody is one which has been separated from a component of its natural environment. i.e. that is not in its natural milieu. No particular level of purification is required. For example, an isolated antibody can be removed from its native or natural environment.

Recombinantly produced antibodies expressed in host cells are considered isolated for the purpose of the invention, as are native or recombinant antibodies which have been separated, fractionated, or partially or substantially purified by any suitable technique. As such, the antibodies and bispecific antigen binding molecules of the present invention are isolated. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007).

The terms "full length antibody," "intact antibody," and "whole antibody" are used herein interchangeably to refer to an antibody having a structure substantially similar to a native antibody structure.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Pluckthun, in The Pharmacology of Monoclonal Antibodies, vol. 113, Rosenburg and Moore eds., Springer-Verlag, New York, pp. 269-315 (1994): see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.: see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity. As used herein in connection with variable region sequences, "Kabat numbering" refers to the numbering system set forth by Kabat et al., *Sequences of Proteins of Immunological Interest*, 5th Ed. Public Health Service, National Institutes of Health, Bethesda, Md. (1991).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991), referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health. Bethesda, Md. (1991)) is used for the light chain constant domain CL of kappa and lambda isotype and the Kabat EU index numbering system (see pages 661-723) is used for the heavy chain constant domains (CH1. Hinge, CH2 and CH3), which is herein further clarified by referring to "numbering according to Kabat EU index" in this case.

The term "hypervariable region" or "HVR", as used herein, refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs; three in the VH (H1, H2, H3), and three in the VL (L1, L2, L3). Exemplary HVRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following order in VH (or VL): FR1-H1(L1)-FR2-H2(L2)-FR3-H3(L3)-FR4.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. In some embodiments, some FR residues in a humanized antibody are substituted with corresponding residues from a non-human antibody (e.g., the antibody from which the HVR residues are derived), e.g., to restore or improve antibody specificity or affinity. A "humanized form" of an antibody. e.g. of a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. In certain embodiments, a human antibody is derived from a non-human transgenic mammal, for example a mouse, a rat, or a rabbit. In certain embodiments, a human antibody is derived from a hybridoma cell line. Antibodies or antibody fragments isolated from human antibody libraries are also considered human antibodies or human antibody fragments herein.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in an antibody or bispecific antigen binding molecule according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in an antibody or bispecific antigen binding molecule according to the invention, comprises an additional C-terminal glycine residue (G446, numbering according to EU index of Kabat). Compositions of the invention, such as the pharmaceutical compositions described herein, comprise a population of antibodies or bispecific antigen binding molecules of the invention. The population of antibodies or bispecific antigen binding molecules may comprise molecules having a full-length heavy chain and molecules having a cleaved variant heavy chain. The population of antibodies or bispecific antigen binding molecules may consist of a mixture of molecules having a full-length heavy chain and molecules having a cleaved variant heavy chain, wherein at least 50%, at least 60%, at least 70%, at least 80% or at least 90% of the antibodies or bispecific antigen binding molecules have a cleaved variant heavy chain. In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of antibodies or bispecific antigen binding molecules of the invention comprises an antibody or bispecific antigen binding molecule comprising a heavy chain including a subunit of an Fc domain as specified herein with an additional C-terminal glycine residue (G446, numbering according to EU index of Kabat). In one embodiment of the invention such a composition comprises a population of antibodies or bispecific antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, Clustal W, Megalign (DNASTAR) software or the FASTA program package. Those skilled in the art can determine appropriate parameters for aligning sequences, including any algorithms needed to achieve maximal alignment over the full length of the sequences being compared. For purposes herein, however, % amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36. Alternatively, a public server can be used to compare the sequences, using the ggsearch (global protein:protein) program and default options (BLOSUM50; open: −10; ext: −2; Ktup=2) to ensure a global, rather than local, alignment is performed. Percent amino acid identity is given in the output alignment header.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

"Isolated polynucleotide (or nucleic acid) encoding [e.g. an antibody or bispecific antigen binding molecule of the invention]" refers to one or more polynucleotide molecules encoding antibody heavy and light chains (or fragments thereof), including such polynucleotide molecule(s) in a single vector or separate vectors, and such nucleic acid molecule(s) present at one or more locations in a host cell.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette comprises polynucleotide sequences that encode antibodies or bispecific antigen binding molecules of the invention or fragments thereof.

The term "vector" or "expression vector" refers to a DNA molecule that is used to introduce and direct the expression of a specific gene to which it is operably associated in a cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the cell, the ribonucleic acid molecule or protein that is encoded by the gene is produced by the cellular transcription and/or translation machinery. In one embodiment, the expression vector of the invention comprises an expression cassette that comprises polynucleotide sequences that encode antibodies or bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies or bispecific antigen binding molecules of the present invention. Host cells include cultured cells, e.g. mammalian cultured cells, such as HEK cells, CHO cells, BHK cells, NS0 cells. SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue. An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies or bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The invention provides antibodies and bispecific antigen binding molecules that bind STEAP-1, particularly human STEAP-1, and are resistant to resistant to degradation e.g. by succinimide formation, and thus particularly stable as required for therapeutic purposes. In addition, the molecules have also other favorable properties for therapeutic application, e.g. with respect to efficacy and/or safety as well as producibility.

STEAP-1 Antibody

Thus, in a first aspect the present invention provides an antibody that binds to STEAP-1, wherein the antibody shows less than about 5% succinimide degradation after 4 weeks at pH 7.4, 37° C., and/or less than about 10% succinimide degradation after 4 weeks at pH 6.0, 40° C., as determined by mass spectrometry. In one embodiment, the antibody shows less than about 3% succinimide degradation, particularly less than about 1% succinimide degradation, after 4 weeks at pH 7.4, 37° C., as determined by mass spectrometry. In one embodiment, the antibody shows less than about 7.5% succinimide degradation, particularly less than about 5% succinimide degradation, after 4 weeks at pH 6.0, 40° C., as determined by mass spectrometry.

In a further aspect the present invention provides an antibody that binds to STEAP-1, wherein the antibody comprises a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9.

In a particular embodiment, the antibody comprises a VH comprising a HCDR 1 of SEQ ID NO: 1, a HCDR 2 of SEQ ID NO: 2, and a HCDR 3 of SEQ ID NO: 6, and a VL comprising a LCDR 1 of SEQ ID NO: 7, a LCDR 2 of SEQ ID NO: 8 and a LCDR 3 of SEQ ID NO: 9.

In some embodiments, the antibody is a humanized antibody. In one embodiment, the VH is a humanized VH and/or the VL is a humanized VL. In one embodiment, the antibody comprises CDRs as in any of the above embodiments, and further comprises an acceptor human framework, e.g. a human immunoglobulin framework or a human consensus framework.

In one embodiment, the VH comprises an amino acid sequence that is at least about 95%, 96%, 97%, 98%, 99% or 1000% identical to an amino acid sequence selected from the group of SEQ ID NO: 11, SEQ ID NO: 12 and SEQ ID NO: 13, and the VL comprises an amino acid sequence that is at least about 95%, 96%, 97%, 98%, 99% or 100% identical to the amino acid sequence of SEQ ID NO: 14.

In one embodiment, the antibody comprises a VH sequence that is at least about 95%, 96%, 97%, 98%, 99% or 100% identical to an amino acid sequence selected from the group of SEQ ID NO: 11, SEQ ID NO: 12 and SEQ ID NO: 13, and a VL sequence that is at least about 95%, 96%, 97%, 98%, 99% or 100% identical to the amino acid sequence of SEQ ID NO: 14.

In certain embodiments, a VH or VL sequence having at least 95%, 96%, 97%, 98%, or 99% identity contains substitutions (e.g., conservative substitutions), insertions, or deletions relative to the reference sequence, but an antibody comprising that sequence retains the ability to bind to STEAP-1. In certain embodiments, a total of 1 to 10 amino acids have been substituted, inserted and/or deleted in SEQ ID NO: 11, 12 or 13 and/or a total of 1 to 10 amino acids have been substituted, inserted and/or deleted in SEQ ID NO: 14. In certain embodiments, substitutions, insertions, or deletions occur in regions outside the HVRs (i.e., in the FRs). Optionally, the antibody comprises the VH sequence in SEQ ID NO: 11, 12 or 13 and/or the VL sequence in SEQ ID NO:14, including post-translational modifications of that sequence.

In one embodiment, the antibody comprises a VH comprising an amino acid sequence selected from the group of SEQ ID NO: 11, SEQ ID NO: 12 and SEQ ID NO: 13, and a VL comprising the amino acid sequence of SEQ ID NO: 14.

In one embodiment, the antibody comprises a VH sequence selected from the group of SEQ ID NO: 11, SEQ ID NO: 12 and SEQ ID NO. 13, and the VL sequence of SEQ ID NO: 14.

In a particular embodiment, the antibody comprises a VH comprising the amino acid sequence of SEQ ID NO: 13 and a VL comprising the amino acid sequence of SEQ ID NO: 14.

In a particular embodiment, the antibody comprises the VH sequence of SEQ ID NO: 13 and the VL sequence of SEQ ID NO: 14.

In one embodiment, the antibody comprises a human constant region. In one embodiment, the antibody is an immunoglobulin molecule comprising a human constant region, particularly an IgG class immunoglobulin molecule comprising a human CH1, CH2, CH3 and/or CL domain.

Exemplary sequences of human constant domains are given in SEQ ID NOs 39 and 40 (human kappa and lambda CL domains, respectively) and SEQ ID NO: 41 (human IgG1 heavy chain constant domains CH1-CH2-CH3). In some embodiments, the antibody comprises a light chain constant region comprising an amino acid sequence that is at least about 95%, 96%, 97%, 98%, 99% or 100% identical to the amino acid sequence of SEQ ID NO: 39 or SEQ ID NO:

40, particularly the amino acid sequence of SEQ ID NO: 39. In some embodiments, the antibody comprises a heavy chain constant region comprising an amino acid sequence that is at least about 95%, 96%, 97%, 98%, 99% or 100% identical to the amino acid sequence of SEQ ID NO: 41. Particularly, the heavy chain constant region may comprise amino acid mutations in the Fc domain as described herein.

In one embodiment, the antibody is a monoclonal antibody.

In one embodiment, the antibody is an IgG, particularly an IgG$_1$, antibody. In one embodiment, the antibody is a full-length antibody.

In one embodiment, the antibody comprises an Fc domain, particularly an IgG Fc domain, more particularly an IgG1 Fc domain. In one embodiment the Fc domain is a human Fc domain. The Fc domain of the antibody may incorporate any of the features, singly or in combination, described herein in relation to the Fc domain of the bispecific antigen binding molecule of the invention.

In another embodiment, the antibody is an antibody fragment selected from the group of an Fv molecule, a scFv molecule, a Fab molecule, and a F(ab')$_2$ molecule; particularly a Fab molecule.

In another embodiment, the antibody fragment is a diabody, a triabody or a tetrabody.

In a further aspect, the antibody according to any of the above embodiments may incorporate any of the features, singly or in combination, as described in the sections below.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the oligosaccharide attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a non-fucosylated oligosaccharide, i.e. an oligosaccharide structure that lacks fucose attached (directly or indirectly) to an Fc region. Such non-fucosylated oligosaccharide (also referred to as "afucosylated" oligosaccharide) particularly is an N-linked oligosaccharide which lacks a fucose residue attached to the first GlcNAc in the stem of the biantennary oligosaccharide structure. In one embodiment, antibody variants are provided having an increased proportion of non-fucosylated oligosaccharides in the Fc region as compared to a native or parent antibody. For example, the proportion of non-fucosylated oligosaccharides may be at least about 20%, at least about 40%, at least about 60%, at least about 80%, or even about 100% (i.e. no fucosylated oligosaccharides are present). The percentage of non-fucosylated oligosaccharides is the (average) amount of oligosaccharides lacking fucose residues, relative to the sum of all oligosaccharides attached to Asn 297 (e. g. complex, hybrid and high mannose structures) as measured by MALDI-TOF mass spectrometry, as described in WO 2006/082515, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such antibodies having an increased proportion of non-fucosylated oligosaccharides in the Fc region may have improved FcγRIIIa receptor binding and/or improved effector function, in particular improved ADCC function. See, e.g., US 2003/0157108; US 2004/0093621.

Examples of cell lines capable of producing antibodies with reduced fucosylation include Lec13 CHO cells deficient in protein fucosylation (Ripka et al. *Arch. Biochem. Biophys.* 249:533-545 (1986); US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87:614-622 (2004); Kanda, Y. et al., *Biotechnol. Bioeng.*, 94(4):680-688 (2006); and WO2003/085107), or cells with reduced or abolished activity of a GDP-fucose synthesis or transporter protein (see, e.g., US2004259150, US2005031613, US2004132140, US2004110282).

In a further embodiment, antibody variants are provided with bisected oligosaccharides, e.g., in which a biantennary oligosaccharide attached to the Fc region of the antibody is bisected by GlcNAc. Such antibody variants may have reduced fucosylation and/or improved ADCC function as described above. Examples of such antibody variants are described, e.g., in Umana et al., Nat Biotechnol 17, 176-180 (1999); Ferrara et al., Biotechn Bioeng 93, 851-861 (2006); WO 99/54342; WO 2004/065540, WO 2003/011878.

Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. Cysteine engineered antibodies may be generated as described, e.g., in U.S. Pat. Nos. 7,521,541, 830,930, 7,855,275, 9,000,130, or WO2016040856.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Immunoconjugates

The invention also provides immunoconjugates comprising an anti-STEAP-1 antibody as described herein conjugated (chemically bonded) to one or more therapeutic agents such as cytotoxic agents, chemotherapeutic agents, drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more of the therapeutic agents mentioned above. The antibody is typically connected to one or more of the therapeutic agents using linkers. An overview of ADC technology including examples of therapeutic agents and drugs and linkers is set forth in *Pharmacol Review* 68:3-19 (2016).

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992): U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Multispecific Antibodies

In certain embodiments, an antibody provided herein is a multispecific antibody, e.g. a bispecific antibody. Multispecific antibodies are monoclonal antibodies that have binding specificities for at least two different sites, i.e., different epitopes on different antigens or different epitopes on the same antigen. In certain embodiments, the multispecific antibody has three or more binding specificities. In certain embodiments, one of the binding specificities is for STEAP-1 and the other (two or more) specificity is for any other antigen. In certain embodiments, bispecific antibodies may bind to two (or more) different epitopes of STEAP-1. Multispecific (e.g., bispecific) antibodies may also be used to localize cytotoxic agents or cells to cells which express STEAP-1. Multispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see. e.g., U.S. Pat. No. 5,731,168, and Atwell et al., *J. Mol. Biol.* 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368

(1994)); and preparing trispecific antibodies as described, e.g., in Tutt et al. *J Immunol.* 147: 60 (1991).

Engineered antibodies with three or more antigen binding sites, including for example, "Octopus antibodies." or DVD-Ig are also included herein (see, e.g. WO 2001/77342 and WO 2008/024715). Other examples of multispecific antibodies with three or more antigen binding sites can be found in WO 2010/115589, WO 2010/112193, WO 2010/136172, WO2010/145792, and WO 2013/026831. The bispecific antibody or antigen binding fragment thereof also includes a "Dual Acting FAb" or "DAF" comprising an antigen binding site that binds to STEAP-1 as well as another different antigen, or two different epitopes of STEAP-1 (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., *Mol Immunol* 67 (2015) 95-106).

A particular type of multispecific antibodies, also included herein, are bispecific antibodies designed to simultaneously bind to a surface antigen on a target cell, e.g., a tumor cell, and to an activating, invariant component of the T cell receptor (TCR) complex, such as CD3, for retargeting of T cells to kill target cells. Hence, in certain embodiments, an antibody provided herein is a multispecific antibody, particularly a bispecific antibody, wherein one of the binding specificities is for STEAP-1 and the other is for CD3.

Examples of bispecific antibody formats that may be useful for this purpose include, but are not limited to, the so-called "BiTE" (bispecific T cell engager) molecules wherein two scFv molecules are fused by a flexible linker (see, e.g., WO2004/106381, WO2005/061547, WO2007/042261, and WO2008/119567, Nagorsen and Bäuerle, *Exp Cell Res* 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO2013/026839, WO 2016/020309; Bacac et al., Oncoimmunology 5(8) (2016) e1203498.

Bispecific Antigen Binding Molecules that Bind to STEAP-1 and a Second Antigen

The invention also provides a bispecific antigen binding molecule, i.e. an antigen binding molecule that comprises at least two antigen binding moieties capable of specific binding to two distinct antigenic determinants (a first and a second antigen).

According to particular embodiments of the invention, the antigen binding moieties comprised in the bispecific antigen binding molecule are Fab molecules (i.e. antigen binding domains composed of a heavy and a light chain, each comprising a variable and a constant domain). In one embodiment, the first and/or the second antigen binding moiety is a Fab molecule. In one embodiment, said Fab molecule is human. In a particular embodiment, said Fab molecule is humanized. In yet another embodiment, said Fab molecule comprises human heavy and light chain constant domains.

Preferably, at least one of the antigen binding moieties is a crossover Fab molecule. Such modification reduces mispairing of heavy and light chains from different Fab molecules, thereby improving the yield and purity of the bispecific antigen binding molecule of the invention in recombinant production. In a particular crossover Fab molecule useful for the bispecific antigen binding molecule of the invention, the variable domains of the Fab light chain and the Fab heavy chain (VL and VH, respectively) are exchanged. Even with this domain exchange, however, the preparation of the bispecific antigen binding molecule may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired bispecific antigen binding molecule, charged amino acids with opposite charges may be introduced at specific amino acid positions in the CH1 and CL domains of either the Fab molecule(s) binding to the first antigen (STEAP-1), or the Fab molecule binding to the second antigen (e.g. an activating T cell antigen such as CD3), as further described herein. Charge modifications are made either in the conventional Fab molecule(s) comprised in the bispecific antigen binding molecule (such as shown e.g. in FIG. 1A-FIG. 1C, FIG. 1G-FIG. 1J), or in the VH/VL crossover Fab molecule(s) comprised in the bispecific antigen binding molecule (such as shown e.g. in FIG. 1D-FIG. 1F, FIG. 1K-FIG. 1N) (but not in both). In particular embodiments, the charge modifications are made in the conventional Fab molecule(s) comprised in the bispecific antigen binding molecule (which in particular embodiments bind(s) to the first antigen, i.e. STEAP-1).

In a particular embodiment according to the invention, the bispecific antigen binding molecule is capable of simultaneous binding to the first antigen (i.e. STEAP-1), and the second antigen (e.g. an activating T cell antigen, particularly CD3). In one embodiment, the bispecific antigen binding molecule is capable of crosslinking a T cell and a target cell by simultaneous binding STEAP-1 and an activating T cell antigen. In an even more particular embodiment, such simultaneous binding results in lysis of the target cell, particularly a STEAP-1 expressing tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the bispecific antigen binding molecule to the activating T cell antigen, particularly CD3, without simultaneous binding to STEAP-1 does not result in T cell activation.

In one embodiment, the bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell. Particularly, a T cell according to any of the embodiments of the invention is a cytotoxic T cell. In some embodiments the T cell is a CD4⁺ or a CD8⁺ T cell, particularly a CD8⁺ T cell.

First Antigen Binding Moiety

The bispecific antigen binding molecule of the invention comprises at least one antigen binding moiety, particularly a Fab molecule, that binds to STEAP-1 (first antigen). In certain embodiments, the bispecific antigen binding molecule comprises two antigen binding moieties, particularly Fab molecules, which bind to STEAP-1. In a particular such embodiment, each of these antigen binding moieties binds to the same antigenic determinant. In an even more particular embodiment, all of these antigen binding moieties are identical, i.e. they comprise the same amino acid sequences including the same amino acid substitutions in the CH1 and CL domain as described herein (if any). In one embodiment, the bispecific antigen binding molecule comprises not more than two antigen binding moieties, particularly Fab molecules, which bind to STEAP-1.

In particular embodiments, the antigen binding moiety(ies) which bind to STEAP-1 is/are a conventional Fab molecule. In such embodiments, the antigen binding moiety(ies) that binds to a second antigen is a crossover Fab molecule as described herein, i.e. a Fab molecule wherein the variable domains VH and VL or the constant domains CH1 and CL of the Fab heavy and light chains are exchanged/replaced by each other.

In alternative embodiments, the antigen binding moiety(ies) which bind to STEAP-1 is/are a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds a second antigen is a conventional Fab molecule.

The STEAP-1 binding moiety is able to direct the bispecific antigen binding molecule to a target site, for example to a specific type of tumor cell that expresses STEAP-1.

The first antigen binding moiety of the bispecific antigen binding molecule may incorporate any of the features, singly or in combination, described herein in relation to the antibody that binds STEAP-1, unless scientifically clearly unreasonable or impossible.

Thus, in one aspect, the invention provides a bispecific antigen binding molecule, comprising (a) a first antigen binding moiety that binds to a first antigen, wherein the first antigen is STEAP-1 and the first antigen binding moiety comprises a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9, and (b) a second antigen binding moiety that binds to a second antigen.

In a particular embodiment, the first antigen binding moiety comprises a VH comprising a HCDR 1 of SEQ ID NO: 1, a HCDR 2 of SEQ ID NO: 2, and a HCDR 3 of SEQ ID NO: 6, and a VL comprising a LCDR 1 of SEQ ID NO: 7, a LCDR 2 of SEQ ID NO: 8 and a LCDR 3 of SEQ ID NO: 9.

In some embodiments, the first antigen binding moiety is (derived from) a humanized antibody.

In one embodiment, the VH is a humanized VH and/or the VL is a humanized VL. In one embodiment, the first antigen binding moiety comprises CDRs as in any of the above embodiments, and further comprises an acceptor human framework, e.g. a human immunoglobulin framework or a human consensus framework.

In one embodiment, the VH of the first antigen binding moiety comprises an amino acid sequence that is at least about 95%, 96%, 97%, 98%, 99% or 100% identical to an amino acid sequence selected from the group of SEQ ID NO: 11, SEQ ID NO: 12 and SEQ ID NO: 13, and the VL of the first antigen binding moiety comprises an amino acid sequence that is at least about 95%, 96%, 97%, 98%, 99% or 100% identical to the amino acid sequence of SEQ ID NO: 14.

In one embodiment, the first antigen binding moiety comprises a VH sequence that is at least about 95%, 96%, 97%, 98%, 99% or 100% identical to an amino acid sequence selected from the group of SEQ ID NO: 11, SEQ ID NO: 12 and SEQ ID NO: 13, and a VL sequence that is at least about 95%, 96%, 97%, 98%, 99% or 100% identical to the amino acid sequence of SEQ ID NO: 14.

In one embodiment, the first antigen binding moiety comprises a VH comprising an amino acid sequence selected from the group of SEQ ID NO: 11, SEQ ID NO: 12 and SEQ ID NO: 13, and a VL comprising the amino acid sequence of SEQ ID NO: 14.

In one embodiment, the first antigen binding moiety comprises a VH sequence selected from the group of SEQ ID NO: 11, SEQ ID NO: 12 and SEQ ID NO: 13, and the VL sequence of SEQ ID NO: 14.

In a particular embodiment, the first antigen binding moiety comprises a VH comprising the amino acid sequence of SEQ ID NO: 13 and a VL comprising the amino acid sequence of SEQ ID NO: 14.

In a particular embodiment, the first antigen binding moiety comprises the VH sequence of SEQ ID NO: 13 and the VL sequence of SEQ ID NO: 14.

In one embodiment, the first antigen binding moiety comprises a human constant region. In one embodiment, the first antigen binding moiety is a Fab molecule comprising a human constant region, particularly a human CH1 and/or CL domain. Exemplary sequences of human constant domains are given in SEQ ID NOs 39 and 40 (human kappa and lambda CL domains, respectively) and SEQ ID NO: 41 (human IgG₁ heavy chain constant domains CH1-CH2-CH3). In some embodiments, the first antigen binding moiety comprises a light chain constant region comprising an amino acid sequence that is at least about 95%, 96%, 97%, 98%, 99% or 100% identical to the amino acid sequence of SEQ ID NO: 39 or SEQ ID NO: 40, particularly the amino acid sequence of SEQ ID NO: 39. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the first antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 41. Particularly, the heavy chain constant region (specifically CH1 domain) may comprise amino acid mutations as described herein under "charge modifications".

Second Antigen Binding Moiety

The bispecific antigen binding molecule of the invention comprises at least one antigen binding moiety, particularly a Fab molecule, that binds to a second antigen (different from STEAP-1).

In particular embodiments, the antigen binding moiety that binds the second antigen is a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) that binds to the first antigen (i.e. STEAP-1) is preferably a conventional Fab molecule. In embodiments where there is more than one antigen binding moiety, particularly Fab molecule, that binds to STEAP-1 comprised in the bispecific antigen binding molecule, the antigen binding moiety that binds to the second antigen preferably is a crossover Fab molecule and the antigen binding moieties that bind to STEAP-1 are conventional Fab molecules.

In alternative embodiments, the antigen binding moiety that binds to the second antigen is a conventional Fab molecule. In such embodiments, the antigen binding moiety(ies) that binds to the first antigen (i.e. STEAP-1) is a crossover Fab molecule as described herein, i.e. a Fab molecule wherein the variable domains VH and VL or the constant domains CH1 and CL of the Fab heavy and light chains are exchanged/replaced by each other. In embodiments where there is more than one antigen binding moiety, particularly Fab molecule, that binds to a second antigen comprised in the bispecific antigen binding molecule, the antigen binding moiety that binds to STEAP-1 preferably is a crossover Fab molecule and the antigen binding moieties that bind to the second antigen are conventional Fab molecules.

In some embodiments, the second antigen is an activating T cell antigen (also referred to herein as an "activating T cell antigen binding moiety, or activating T cell antigen binding Fab molecule").

In a particular embodiment, the bispecific antigen binding molecule comprises not more than one antigen binding moiety capable of specific binding to an activating T cell antigen. In one embodiment the bispecific antigen binding molecule provides monovalent binding to the activating T cell antigen.

In particular embodiments, the second antigen is CD3, particularly human CD3 (SEQ ID NO: 24) or cynomolgus CD3 (SEQ ID NO: 25), most particularly human CD3. In one embodiment the second antigen binding moiety is cross-reactive for (i.e. specifically binds to) human and cynomolgus CD3. In some embodiments, the second antigen is the epsilon subunit of CD3 (CD3 epsilon).

In one embodiment, the second antigen binding moiety comprises a HCDR 1 of SEQ ID NO: 15, a HCDR 2 of SEQ ID NO: 16, a HCDR 3 of SEQ ID NO: 17, a LCDR 1 of SEQ ID NO: 18, a LCDR 2 of SEQ ID NO: 19 and a LCDR 3 of SEQ ID NO: 20.

In one embodiment, the second antigen binding moiety comprises a VH comprising a HCDR 1 of SEQ ID NO: 15, a HCDR 2 of SEQ ID NO: 16, and a HCDR 3 of SEQ ID NO: 17, and a VL comprising a LCDR 1 of SEQ ID NO: 18, a LCDR 2 of SEQ ID NO: 19 and a LCDR 3 of SEQ ID NO: 20.

In some embodiments, the second antigen binding moiety is (derived from) a humanized antibody.

In one embodiment, the VH is a humanized VH and/or the VL is a humanized VL. In one embodiment, the second antigen binding moiety comprises CDRs as in any of the above embodiments, and further comprises an acceptor human framework, e.g. a human immunoglobulin framework or a human consensus framework.

In one embodiment, the second antigen binding moiety comprises a VH sequence that is at least about 95%, 96%, 97%, 98%, 99% or 100% identical to the amino acid sequence of SEQ ID NO: 21. In one embodiment, the second antigen binding moiety comprises a V L sequence that is at least about 95%, 96%, 97%, 98%, 99% or 100% identical to the amino acid sequence of SEQ ID NO: 22.

In one embodiment, the second antigen binding moiety comprises a VH sequence that is at least about 95%, 96%, 97%, 98%, 99% or 100% identical to the amino acid sequence of SEQ ID NO: 21, and a VL sequence that is at least about 95%, 96%, 97%, 98%, 99% or 100% identical to the amino acid sequence of SEQ ID NO: 22.

In one embodiment, the VH of the second antigen binding moiety comprises an amino acid sequence that is at least about 95%, 96%, 97%, 98%, 99% or 100% identical to the amino acid sequence of SEQ ID NO: 21, and the VL of the second antigen binding moiety comprises an amino acid sequence that is at least about 95%, 96%, 97%, 98%, 99% or 100% identical to the amino acid sequence of SEQ ID NO: 22.

In one embodiment, the second antigen binding moiety comprises a VH comprising the amino acid sequence of SEQ ID NO: 21, and a VL comprising the amino acid sequence of SEQ ID NO: 22.

In one embodiment, the second antigen binding moiety comprises the VH sequence of SEQ ID NO: 21, and the VL sequence of SEQ ID NO: 22.

In one embodiment, the second antigen binding moiety comprises a human constant region. In one embodiment, the second antigen binding moiety is a Fab molecule comprising a human constant region, particularly a human CH1 and/or CL domain. Exemplary sequences of human constant domains are given in SEQ ID NOs 39 and 40 (human kappa and lambda CL domains, respectively) and SEQ ID NO: 41 (human IgG$_1$ heavy chain constant domains CH1-CH2-CH3). In some embodiments, the second antigen binding moiety comprises a light chain constant region comprising an amino acid sequence that is at least about 95%, 96%, 97%, 98%, 99% or 100% identical to the amino acid sequence of SEQ ID NO: 39 or SEQ ID NO: 40, particularly the amino acid sequence of SEQ ID NO: 39. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the second antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 41. Particularly, the heavy chain constant region (specifically CH1 domain) may comprise amino acid mutations as described herein under "charge modifications".

In some embodiments, the second antigen binding moiety is a Fab molecule wherein the variable domains VL and VH or the constant domains CL and CH1, particularly the variable domains VL and VH, of the Fab light chain and the Fab heavy chain are replaced by each other (i.e. according to such embodiment, the second antigen binding moiety is a crossover Fab molecule wherein the variable or constant domains of the Fab light chain and the Fab heavy chain are exchanged). In one such embodiment, the first (and the third, if any) antigen binding moiety is a conventional Fab molecule.

In one embodiment, not more than one antigen binding moiety that binds to the second antigen (e.g. an activating T cell antigen such as CD3) is present in the bispecific antigen binding molecule (i.e. the bispecific antigen binding molecule provides monovalent binding to the second antigen).

Charge Modifications

The bispecific antigen binding molecules of the invention may comprise amino acid substitutions in Fab molecules comprised therein which are particularly efficient in reducing mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety). The ratio of a desired bispecific antigen binding molecule compared to undesired side products, in particular Bence Jones-type side products occurring in bispecific antigen binding molecules with a VH/VL domain exchange in one of their binding arms, can be improved by the introduction of charged amino acids with opposite charges at specific amino acid positions in the CH1 and CL domains (sometimes referred to herein as "charge modifications").

Accordingly, in some embodiments wherein the first and the second antigen binding moiety of the bispecific antigen binding molecule are both Fab molecules, and in one of the antigen binding moieties (particularly the second antigen binding moiety) the variable domains VL and VH of the Fab light chain and the Fab heavy chain are replaced by each other, i) in the constant domain CL of the first antigen binding moiety the amino acid at position 124 is substituted by a positively charged amino acid (numbering according to Kabat), and wherein in the constant domain CH1 of the first antigen binding moiety the amino acid at position 147 or the amino acid at position 213 is substituted by a negatively charged amino acid (numbering according to Kabat EU index); or ii) in the constant domain CL of the second antigen binding moiety the amino acid at position 124 is substituted by a positively charged amino acid (numbering according to Kabat), and wherein in the constant domain CH1 of the second antigen binding moiety the amino acid at position 147 or the amino acid at position 213 is substituted by a negatively charged amino acid (numbering according to Kabat EU index).

The bispecific antigen binding molecule does not comprise both modifications mentioned under i) and ii). The constant domains CL and CH1 of the antigen binding moiety having the VH/VL exchange are not replaced by each other (i.e. remain unexchanged).

In a more specific embodiment, i) in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index); or ii) in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D) (numbering according to Kabat EU index).

In one such embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 or the amino acid at position 213 is substituted independently by glutamic acid (E), or aspartic acid (D) (numbering according to Kabat EU index).

In a further embodiment, in the constant domain CL of the first antigen binding moiety the amino acid at position 124 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index).

In a particular embodiment, in the constant domain CL of the first antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first antigen binding moiety the amino acid at position 124 is substituted by lysine (K) (numbering according to Kabat) and the amino acid at position 123 is substituted by lysine (K) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first antigen binding moiety the amino acid at position 124 is substituted by lysine (K) (numbering according to Kabat) and the amino acid at position 123 is substituted by arginine (R) (numbering according to Kabat), and in the constant domain CH1 of the first antigen binding moiety the amino acid at position 147 is substituted by glutamic acid (E) (numbering according to Kabat EU index) and the amino acid at position 213 is substituted by glutamic acid (E) (numbering according to Kabat EU index).

In particular embodiments, if amino acid substitutions according to the above embodiments are made in the constant domain CL and the constant domain CH1 of the first antigen binding moiety, the constant domain CL of the first antigen binding moiety is of kappa isotype.

Alternatively, the amino acid substitutions according to the above embodiments may be made in the constant domain CL and the constant domain CH1 of the second antigen binding moiety instead of in the constant domain CL and the constant domain CH1 of the first antigen binding moiety. In particular such embodiments, the constant domain CL of the second antigen binding moiety is of kappa isotype.

Accordingly, in one embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 or the amino acid at position 213 is substituted independently by glutamic acid (E), or aspartic acid (D)(numbering according to Kabat EU index).

In a further embodiment, in the constant domain CL of the second antigen binding moiety the amino acid at position 124 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index).

In still another embodiment, in the constant domain CL of the second antigen binding moiety the amino acid at position 124 is substituted independently by lysine (K), arginine (R) or histidine (H) (numbering according to Kabat) and the amino acid at position 123 is substituted independently by lysine (K), arginine (R) or histidine (H) (numbering according to Kabat), and in the constant domain CH1 of the second antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second antigen binding moiety the amino acid at position 124 is substituted by lysine (K) (numbering according to Kabat) and the amino acid at position 123 is substituted by lysine (K) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In another embodiment, in the constant domain CL of the second antigen binding moiety the amino acid at position 124 is substituted by lysine (K) (numbering according to Kabat) and the amino acid at position 123 is substituted by arginine (R) (numbering according to Kabat), and in the constant domain CH1 of the second antigen binding moiety the amino acid at position 147 is substituted by glutamic acid (E) (numbering according to Kabat EU index) and the amino acid at position 213 is substituted by glutamic acid (E) (numbering according to Kabat EU index).

In a particular embodiment, the bispecific antigen binding molecule of the invention comprises (a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9, and (b) a second antigen binding moiety that binds to a second antigen, wherein the second antigen binding moiety is a Fab molecule wherein the variable domains VL and VH of the Fab light chain and the Fab heavy chain are replaced by each other;

wherein in the constant domain CL of the first antigen binding moiety the amino acid at position 124 is substituted independently by lysine (K), arginine (R) or histidine (H) (numbering according to Kabat) (in a particular embodiment independently by lysine (K) or arginine (R)) and the amino acid at position 123 is substituted independently by lysine (K), arginine (R) or histidine (H) (numbering according to Kabat) (in a particular embodiment independently by lysine (K) or arginine (R)), and in the constant domain CH1 of the first antigen binding moiety the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

Bispecific Antigen Binding Molecule Formats

Figure 1B:
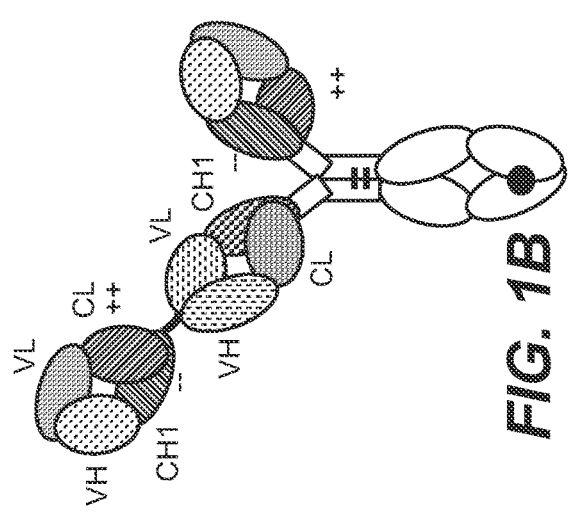
(FIG. 1B, FIG. 1E) Illustration of the "2+1 IgG Crossfab" molecule with alternative order of Crossfab and Fab components ("inverted").
Figure 1C:
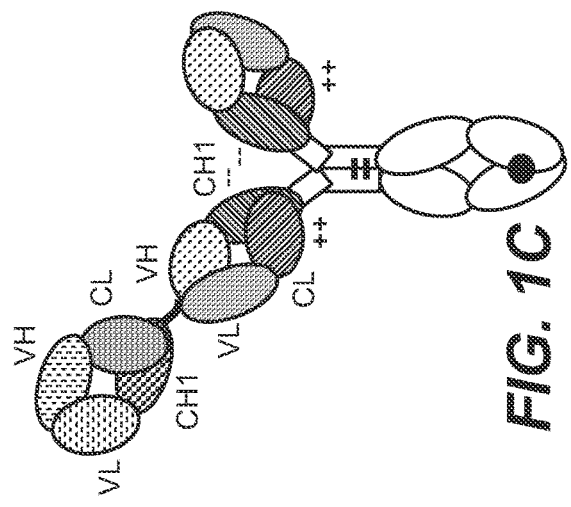
(FIG. 1C, FIG. 1F) Illustration of the "2+1 IgG Crossfab" molecule.
Figure 1D:
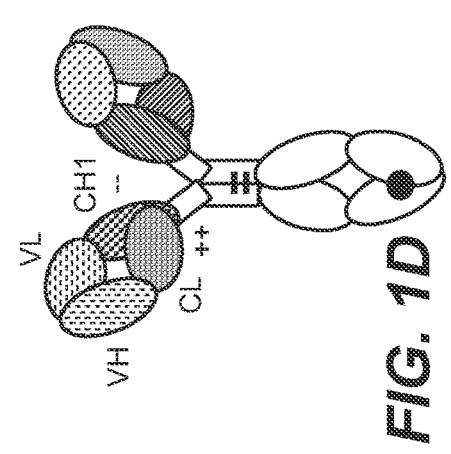
Figure 1E:
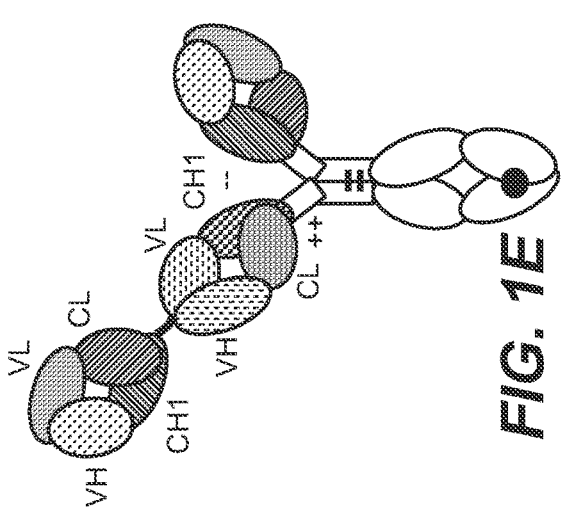
Figure 1F:
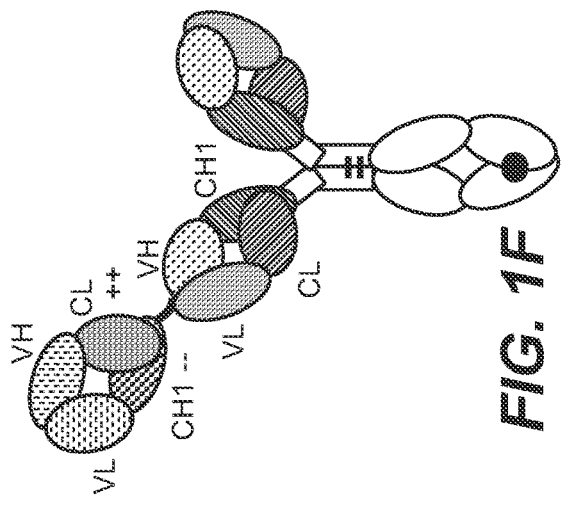
Figure 1W:
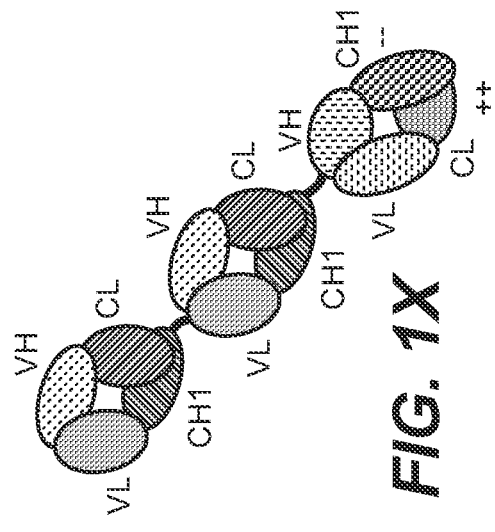
(FIG. 1W, FIG. 1Y) Illustration of the "Fab-(Crossfab)$_2$" molecule.
Figure 1X:
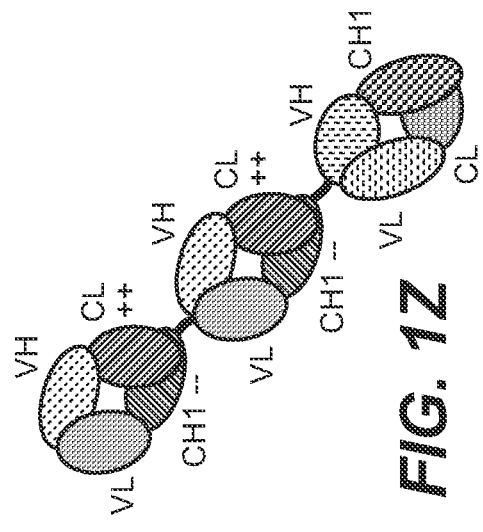
Figure 1Y:
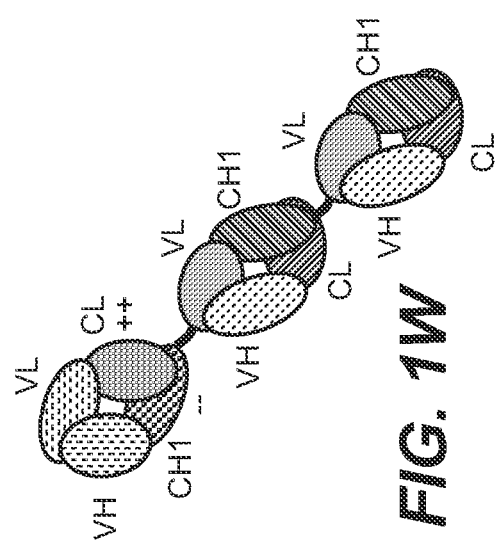
Figure 1Z:
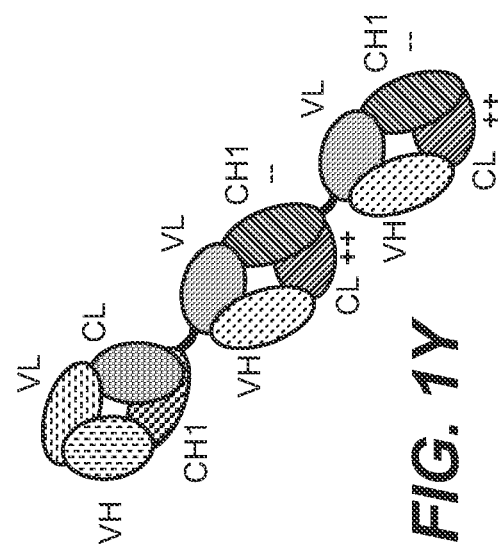

The components of the bispecific antigen binding molecule according to the present invention can be fused to each other in a variety of configurations. Exemplary configurations are depicted in FIG. 1A-FIG. 1Z.

In particular embodiments, the antigen binding moieties comprised in the bispecific antigen binding molecule are Fab molecules. In such embodiments, the first, second, third etc. antigen binding moiety may be referred to herein as first, second, third etc. Fab molecule, respectively.

In one embodiment, the first and the second antigen binding moiety of the bispecific antigen binding molecule are fused to each other, optionally via a peptide linker. In particular embodiments, the first and the second antigen binding moiety are each a Fab molecule. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety. In embodiments wherein either (i) the second antigen binding moiety is fused at the C-terminus of the Fab heavy chain to the N-terminus of the Fab heavy chain of the first antigen binding moiety or (ii) the first antigen binding moiety is fused at the C-terminus of the Fab heavy chain to the N-terminus of the Fab heavy chain of the second antigen binding moiety, additionally the Fab light chain of the first antigen binding moiety and the Fab light chain of the second antigen binding moiety may be fused to each other, optionally via a peptide linker.

A bispecific antigen binding molecule with a single antigen binding moiety (such as a Fab molecule) capable of specific binding to a target cell antigen such as STEAP-1 (for example as shown in FIG. 1A, FIG. 1D, FIG. 1G, FIG. 1H, FIG. 1K, FIG. 1L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In other cases, however, it will be advantageous to have a bispecific antigen binding molecule comprising two or more antigen binding moieties (such as Fab molecules) specific for a target cell antigen (see examples shown in FIG. 1B, FIG. 1C, FIG. 1E, FIG. 1F, FIG. 1I, FIG. 1J, FIG. 1M or FIG. 1N), for example to optimize targeting to the target site or to allow crosslinking of target cell antigens.

Accordingly, in particular embodiments, the bispecific antigen binding molecule according to the present invention comprises a third antigen binding moiety.

In one embodiment, the third antigen binding moiety binds to the first antigen, i.e. STEAP-1. In one embodiment, the third antigen binding moiety is a Fab molecule.

In one embodiment, the third antigen moiety is identical to the first antigen binding moiety.

The third antigen binding moiety of the bispecific antigen binding molecule may incorporate any of the features, singly or in combination, described herein in relation to the first antigen binding moiety and/or the antibody that binds STEAP-1, unless scientifically clearly unreasonable or impossible.

In one embodiment, the third antigen binding moiety comprises a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9.

In a particular embodiment, the third antigen binding moiety comprises a VH comprising a HCDR 1 of SEQ ID NO: 1, a HCDR 2 of SEQ ID NO: 2, and a HCDR 3 of SEQ ID NO: 6, and a VL comprising a LCDR 1 of SEQ ID NO: 7, a LCDR 2 of SEQ ID NO: 8 and a LCDR 3 of SEQ ID NO: 9.

In some embodiments, the third antigen binding moiety is (derived from) a humanized antibody.

In one embodiment, the VH is a humanized VH and/or the VL is a humanized VL. In one embodiment, the third antigen binding moiety comprises CDRs as in any of the above embodiments, and further comprises an acceptor human framework, e.g. a human immunoglobulin framework or a human consensus framework.

In one embodiment, the VH of the third antigen binding moiety comprises an amino acid sequence that is at least about 95%, 96%, 97%, 98%, 99% or 100% identical to an amino acid sequence selected from the group of SEQ ID NO: 11, SEQ ID NO: 12 and SEQ ID NO: 13, and the VL of the third antigen binding moiety comprises an amino acid sequence that is at least about 95%, 96%, 97%, 98%, 99% or 100% identical to the amino acid sequence of SEQ ID NO: 14.

In one embodiment, the third antigen binding moiety comprises a VH sequence that is at least about 95%, 96%, 97%, 98%, 99% or 100% identical to an amino acid sequence selected from the group of SEQ ID NO: 11, SEQ ID NO: 12 and SEQ ID NO: 13, and a VL sequence that is at least about 95%, 96%, 97%, 98%, 99% or 100% identical to the amino acid sequence of SEQ ID NO: 14.

In one embodiment, the third antigen binding moiety comprises a VH comprising an amino acid sequence selected from the group of SEQ ID NO: 11, SEQ ID NO: 12 and SEQ ID NO: 13, and a VL comprising the amino acid sequence of SEQ ID NO: 14.

In one embodiment, the third antigen binding moiety comprises a VH sequence selected from the group of SEQ ID NO: 11, SEQ ID NO: 12 and SEQ ID NO: 13, and the VL sequence of SEQ ID NO: 14.

In a particular embodiment, the third antigen binding moiety comprises a VH comprising the amino acid sequence of SEQ ID NO: 13 and a VL comprising the amino acid sequence of SEQ ID NO: 14.

In a particular embodiment, the third antigen binding moiety comprises the VH sequence of SEQ ID NO: 13 and the VL sequence of SEQ ID NO: 14.

In one embodiment, the third antigen binding moiety comprises a human constant region. In one embodiment, the third antigen binding moiety is a Fab molecule comprising a human constant region, particularly a human CH1 and/or CL domain. Exemplary sequences of human constant domains are given in SEQ ID NOs 39 and 40 (human kappa and lambda CL domains, respectively) and SEQ ID NO: 41 (human IgG$_1$ heavy chain constant domains CH1-CH2-CH3). In some embodiments, the third antigen binding moiety comprises a light chain constant region comprising an amino acid sequence that is at least about 95%, 96%, 97%, 98%, 99% or 100% identical to the amino acid sequence of SEQ ID NO: 39 or SEQ ID NO: 40, particularly the amino acid sequence of SEQ ID NO: 39. Particularly, the light chain constant region may comprise amino acid mutations as described herein under "charge modifications" and/or may comprise deletion or substitutions of one or more (particularly two) N-terminal amino acids if in a crossover Fab molecule. In some embodiments, the third antigen binding moiety comprises a heavy chain constant region comprising an amino acid sequence that is at least about 95%, 96%, 97%, 98%, 99% or 100% identical to the CH1 domain sequence comprised in the amino acid sequence of SEQ ID NO: 41. Particularly, the heavy chain constant region (specifically CH1 domain) may comprise amino acid mutations as described herein under "charge modifications".

In particular embodiments, the third and the first antigen binding moiety are each a Fab molecule and the third antigen binding moiety is identical to the first antigen binding moiety. Thus, in these embodiments the first and the third antigen binding moiety comprise the same heavy and light chain amino acid sequences and have the same arrangement of domains (i.e. conventional or crossover)). Furthermore, in these embodiments, the third antigen binding moiety comprises the same amino acid substitutions, if any, as the first antigen binding moiety. For example, the amino acid substitutions described herein as "charge modifications" will be made in the constant domain CL and the constant domain CH1 of each of the first antigen binding moiety and the third antigen binding moiety. Alternatively, said amino acid substitutions may be made in the constant domain CL and the constant domain CH1 of the second antigen binding moiety (which in particular embodiments is also a Fab molecule), but not in the constant domain CL and the constant domain CH1 of the first antigen binding moiety and the third antigen binding moiety.

Like the first antigen binding moiety, the third antigen binding moiety particularly is a conventional Fab molecule. Embodiments wherein the first and the third antigen binding moieties are crossover Fab molecules (and the second antigen binding moiety is a conventional Fab molecule) are, however, also contemplated. Thus, in particular embodiments, the first and the third antigen binding moieties are each a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other embodiments, the first and the third antigen binding moieties are each a crossover Fab molecule and the second antigen binding moiety is a conventional Fab molecule.

If a third antigen binding moiety is present, in a particular embodiment the first and the third antigen moiety bind to STEAP-1, and the second antigen binding moiety binds to a second antigen, particularly an activating T cell antigen, more particularly CD3, most particularly CD3 epsilon.

In particular embodiments, the bispecific antigen binding molecule comprises an Fc domain composed of a first and a second subunit. The first and the second subunit of the Fc domain are capable of stable association.

The bispecific antigen binding molecule according to the invention can have different configurations, i.e. the first, second (and optionally third) antigen binding moiety may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In some embodiments, the first and the second antigen binding moiety are each a Fab molecule and the second antigen binding moiety is fused at the C-terminus of the Fab heavy chain to the N-terminus of the first or the second subunit of the Fc domain. In such embodiments, the first antigen binding moiety may be fused at the C-terminus of the Fab heavy chain to the N-terminus of the Fab heavy chain of the second antigen binding moiety or to the N-terminus of the other one of the subunits of the Fc domain. In particular such embodiments, said first antigen binding moiety is a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other.

In other such embodiments, said first Fab molecule is a crossover Fab molecule and the second Fab molecule is a conventional Fab molecule.

In one embodiment, the first and the second antigen binding moiety are each a Fab molecule, the second antigen binding moiety is fused at the C-terminus of the Fab heavy chain to the N-terminus of the first or the second subunit of the Fc domain, and the first antigen binding moiety is fused at the C-terminus of the Fab heavy chain to the N-terminus of the Fab heavy chain of the second antigen binding moiety. In a specific embodiment, the bispecific antigen binding molecule essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1G and FIG. 1K (with the second antigen binding domain in these examples being a VH/VL crossover Fab molecule). Optionally, the Fab light chain of the first Fab molecule and the Fab light chain of the second Fab molecule may additionally be fused to each other.

In another embodiment, the first and the second antigen binding moiety are each a Fab molecule and the first and the second antigen binding moiety are each fused at the C-terminus of the Fab heavy chain to the N-terminus of one of the subunits of the Fc domain. In a specific embodiment, the bispecific antigen binding molecule essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D (in these examples with the second antigen binding domain being a VH/VL crossover Fab molecule and the first antigen binding moiety being a conventional Fab molecule). The first and the second Fab molecule may be fused to the Fc domain directly or through a peptide linker. In a particular embodiment the first and the second Fab molecule are each fused to the Fc domain through an immunoglobulin hinge region.

In a specific embodiment, the immunoglobulin hinge region is a human IgG$_1$ hinge region, particularly where the Fc domain is an IgG$_1$ Fc domain.

In some embodiments, the first and the second antigen binding moiety are each a Fab molecule and the first antigen binding moiety is fused at the C-terminus of the Fab heavy chain to the N-terminus of the first or the second subunit of the Fc domain. In such embodiments, the second antigen binding moiety may be fused at the C-terminus of the Fab heavy chain to the N-terminus of the Fab heavy chain of the second antigen binding moiety or (as described above) to the N-terminus of the other one of the subunits of the Fc domain. In particular such embodiments, said first antigen binding moiety is a conventional Fab molecule, and the second antigen binding moiety is a crossover Fab molecule as described herein, i.e. a Fab molecule wherein the variable domains VH and VL or the constant domains CL and CH1 of the Fab heavy and light chains are exchanged/replaced by each other. In other such embodiments, said first Fab molecule is a crossover Fab molecule and the second Fab molecule is a conventional Fab molecule.

In one embodiment, the first and the second antigen binding moiety are each a Fab molecule, the first antigen binding moiety is fused at the C-terminus of the Fab heavy chain to the N-terminus of the first or the second subunit of the Fc domain, and the second antigen binding moiety is fused at the C-terminus of the Fab heavy chain to the N-terminus of the Fab heavy chain of the first antigen binding moiety. In a specific embodiment, the bispecific antigen binding molecule essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIG. 1H and FIG. 1L (in these examples with the second antigen binding domain being a VH/VL crossover Fab molecule and the first antigen binding moiety being a conventional Fab molecule). Optionally, the Fab light chain of the first Fab molecule and the Fab light chain of the second Fab molecule may additionally be fused to each other.

In some embodiments, a third antigen binding moiety, particularly a third Fab molecule, is fused at the C-terminus of the Fab heavy chain to the N-terminus of the first or second subunit of the Fc domain. In particular such embodiments, said first and third Fab molecules are each a conventional Fab molecule, and the second Fab molecule is a crossover Fab molecule as described herein, i.e. a Fab molecule wherein the variable domains VH and VL or the constant domains CL and CH1 of the Fab heavy and light chains are exchanged/replaced by each other. In other such embodiments, said first and third Fab molecules are each a crossover Fab molecule and the second Fab molecule is a conventional Fab molecule.

In a particular such embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second Fab molecule. In a specific embodiment, the bispecific antigen binding molecule essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1B and FIG. 1E (in these examples with the second antigen binding moiety being a VH/VL crossover Fab molecule, and the first and the third antigen binding moiety being a conventional Fab molecule), and FIG. 1J and FIG. 1N (in these examples with the second antigen binding moiety being a conventional Fab molecule, and the first and the third antigen binding moiety being a VH/VL crossover Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another such embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In a specific embodiment, the bispecific antigen binding molecule essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1C and FIG. 1F (in these examples with the second antigen binding moiety being a VH/VL crossover Fab molecule, and the first and the third antigen binding moiety being a conventional Fab molecule) and in FIG. 1I and FIG. 1M (in these examples with the second antigen binding moiety being a conventional Fab molecule, and the first and the third antigen binding moiety being a VH/VL crossover Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In configurations of the bispecific antigen binding molecule wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin. In one embodiment, the immunoglobulin comprises a human constant region, particularly a human Fc region.

In some of the bispecific antigen binding molecule of the invention, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the bispecific antigen binding molecules of the invention.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 37 and 38). Another suitable such linker comprises the sequence $(G_4S)_4$. Additionally, linkers may comprise (a portion of) an immunoglobulin hinge region Particularly where a Fab molecule is fused to the N-terminus of an Fc domain subunit, it may be fused via an immunoglobulin hinge region or a portion thereof, with or without an additional peptide linker.

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit ($VL_{(2)}$-$CH1_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(3)}$-CL$_{(1)}$). In certain embodiments the polypeptides are covalently linked, e.g., by a disulfide bond.

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(2)}$-CL$_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In certain embodiments the polypeptides are covalently linked, e.g., by a disulfide bond.

In some embodiments, the bispecific antigen binding molecule comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit (VL$_{(2)}$-CH1$_{(2)}$-VH$_{(1)}$-CH1$_{(1)}$-CH2-CH3(-CH4)). In other embodiments, the bispecific antigen binding molecule comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit (VH$_{(1)}$-CH1$_{(1)}$-VL$_{(2)}$-CH1$_{(2)}$-CH2-CH3(-CH4)).

In some of these embodiments the bispecific antigen binding molecule further comprises a crossover Fab light chain polypeptide of the second Fab molecule, wherein the Fab heavy chain variable region of the second Fab molecule shares a carboxy-terminal peptide bond with the Fab light chain constant region of the second Fab molecule (VH$_{(2)}$-CL$_{(2)}$), and the Fab light chain polypeptide of the first Fab molecule (VL$_{(1)}$-CL$_{(1)}$). In others of these embodiments the bispecific antigen binding molecule further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule (VH$_{(2)}$CL$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$CL$_{(1)}$VH$_{(2)}$CL$_{(2)}$), as appropriate.

The bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$CL$_{(3)}$). In certain embodiments the polypeptides are covalently linked, e.g., by a disulfide bond.

In some embodiments, the bispecific antigen binding molecule comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit (VH$_{(2)}$-CL$_{(2)}$-VH$_{(1)}$-CH1$_{(1)}$CH2-CH3(-CH4)). In other embodiments, the bispecific antigen binding molecule comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(1)}$-CH1$_{(1)}$-VH$_{(2)}$CL$_{(2)}$-CH2-CH3(-CH4)).

In some of these embodiments the bispecific antigen binding molecule further comprises a crossover Fab light chain polypeptide of the second Fab molecule, wherein the Fab light chain variable region of the second Fab molecule shares a carboxy-terminal peptide bond with the Fab heavy chain constant region of the second Fab molecule (VL$_{(2)}$CH1$_{(2)}$), and the Fab light chain polypeptide of the first Fab molecule (VL$_{(1)}$-CL$_{(1)}$). In others of these embodiments the bispecific antigen binding molecule further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule (VL$_{(2)}$-CH1$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$-CL$_{(1)}$-VH$_{(2)}$-CL$_{(2)}$), as appropriate.

The bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

In certain embodiments, the bispecific antigen binding molecule does not comprise an Fc domain. In particular such embodiments, said first and, if present third Fab molecules are each a conventional Fab molecule, and the second Fab molecule is a crossover Fab molecule as described herein. i.e. a Fab molecule wherein the variable domains VH and VL or the constant domains CL and CH1 of the Fab heavy and light chains are exchanged/replaced by each other. In other such embodiments, said first and, if present third Fab molecules are each a crossover Fab molecule and the second Fab molecule is a conventional Fab molecule.

In one such embodiment, the bispecific antigen binding molecule essentially consists of the first and the second antigen binding moiety, and optionally one or more peptide linkers, wherein the first and the second antigen binding moiety are both Fab molecules and the first antigen binding moiety is fused at the C-terminus of the Fab heavy chain to the N-terminus of the Fab heavy chain of the second antigen binding moiety. Such a configuration is schematically depicted in FIG. 1O and FIG. 1S (in these examples with the second antigen binding domain being a VH/VL crossover Fab molecule and the first antigen binding moiety being a conventional Fab molecule).

In another such embodiment, the bispecific antigen binding molecule essentially consists of the first and the second antigen binding moiety, and optionally one or more peptide linkers, wherein the first and the second antigen binding moiety are both Fab molecules and the second antigen binding moiety is fused at the C-terminus of the Fab heavy chain to the N-terminus of the Fab heavy chain of the first antigen binding moiety. Such a configuration is schematically depicted in FIG. 1P and FIG. 1T (in these examples with the second antigen binding domain being a VH/VL crossover Fab molecule and the first antigen binding moiety being a conventional Fab molecule).

In some embodiments, the first Fab molecule is fused at the C-terminus of the Fab heavy chain to the N-terminus of the Fab heavy chain of the second Fab molecule, and the bispecific antigen binding molecule further comprises a third antigen binding moiety, particularly a third Fab molecule, wherein said third Fab molecule is fused at the C-terminus of the Fab heavy chain to the N-terminus of the Fab heavy chain of the first Fab molecule. In certain such embodiments, the bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIG. 1Q and FIG. 1U (in these examples with the second antigen binding domain being a VH/VL crossover Fab molecule and the first and the antigen binding moiety each being a conventional Fab molecule), or FIG. 1X and FIG. 1Z (in these examples with the second antigen binding domain being a conventional Fab molecule and the first and the third antigen binding moiety each being a VH/VL crossover Fab molecule).

In some embodiments, the second Fab molecule is fused at the C-terminus of the Fab heavy chain to the N-terminus of the Fab heavy chain of the first Fab molecule, and the bispecific antigen binding molecule further comprises a third antigen binding moiety, particularly a third Fab molecule, wherein said third Fab molecule is fused at the N-terminus of the Fab heavy chain to the C-terminus of the Fab heavy chain of the first Fab molecule. In certain such embodiments, the bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIG. 1R and FIG. 1V (in these examples with the second antigen binding domain being a VH/VL crossover Fab molecule and the first and the antigen binding moiety each being a conventional Fab molecule), or FIG. 1W and FIG. 1Y (in these examples with the second antigen binding domain being a conventional Fab molecule and the first and the third antigen binding moiety each being a VH/VL crossover Fab molecule).

In certain embodiments the bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) (VH$_{(1)}$-CH1$_{(1)}$-VL$_{(2)}$-CH1$_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule (VL$_{(2)}$-CH1$_{(2)}$-VH$_{(2)}$-CH1$_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule (VH$_{(2)}$-CL$_{(2)}$-VH$_{(1)}$-CH1$_{(1)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region)($VH_{(3)}$-$CH1_{(3)}$-$VH_{(1)}$-$CH1_{(1)}$-$VL_{(2)}$-$CH1_{(2)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region)($VH_{(3)}$-$CH1_{(3)}$-$VH_{(1)}$-$CH1_{(1)}$-$VH_{(2)}$-$CL_{(2)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule ($VL_{(2)}$-$CH1_{(2)}$-$VH_{(1)}$-$CH1_{(1)}$-$VH_{(3)}$-$CH1_{(3)}$). In some embodiments the bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule ($VH_{(2)}$-$CL_{(2)}$-$VH_{(1)}$-$CH1_{(1)}$-$VH_{(3)}$-$CH1_{(3)}$). In some embodiments the bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the bispecific antigen binding molecule further comprises the Fab light chain polypeptide of a third Fab molecule ($VL_{(3)}$-$CL_{(3)}$).

In certain embodiments the bispecific antigen binding molecule according to the invention comprises a polypeptide wherein the Fab heavy chain of the second Fab molecule shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(2)}$-$CH1_{(2)}$-$VL_{(1)}$-$CH1_{(1)}$-$VL_{(3)}$-$CH1_{(3)}$). In some embodiments the bispecific antigen binding molecule further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some embodiments the bispecific antigen binding molecule further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the bispecific antigen binding molecule according to the invention comprises a polypeptide wherein the Fab heavy chain of the second Fab molecule shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(2)}$-$CH1_{(2)}$-$VH_{(1)}$-$CL_{(1)}$-$VH_{(3)}$-$CL_{(3)}$). In some embodiments the bispecific antigen binding molecule further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some embodiments the bispecific antigen binding molecule further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In certain embodiments the bispecific antigen binding molecule according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the first Fab molecule, which in turn shares a carboxy-terminal peptide bond with the Fab heavy chain constant region of the first Fab molecule (i.e. the first Fab molecule comprises a crossover Fab heavy chain, wherein the heavy chain variable region is replaced by a light chain variable region), which in turn shares a carboxy-terminal peptide bond with the Fab heavy chain of the second Fab molecule ($VL_{(3)}$-$CH1_{(3)}$-$VL_{(1)}$$CH1_{(1)}$-$VH_{(2)}$-$CH1_{(2)}$). In some embodiments the bispecific antigen binding molecule further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In some embodiments the bispecific antigen binding molecule further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the bispecific antigen binding molecule according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the first Fab molecule, which in turn shares a carboxy-terminal peptide bond with the Fab light chain constant region of the first Fab molecule (i.e. the first Fab molecule comprises a crossover Fab heavy chain, wherein the heavy chain constant region is replaced by a light chain constant region), which in turn shares a carboxy-terminal peptide bond with the Fab heavy chain of the second Fab molecule ($VH_{(3)}$-$CL_{(3)}$-$VH_{(1)}$-$CL_{(1)}$-$VH_{(2)}$-$CH1_{(1)}$). In some embodiments the bispecific antigen binding molecule further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In some embodiments the bispecific antigen binding molecule further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In one embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other; c) an Fc domain composed of a first and a second subunit:

wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL)

comprising a light chain complementarity determining region (LCDR) 1 of SEQ ID NO: 7, a LCDR 2 of SEQ ID NO: 8 and a LCDR 3 of SEQ ID NO: 9;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other:

c) a third antigen binding moiety that binds to the first antigen and is identical to the first antigen binding moiety; and d) an Fc domain composed of a first and a second subunit; wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH or the constant domains CL and CH1 of the Fab light chain and the Fab heavy chain are replaced by each other:

c) an Fc domain composed of a first and a second subunit; wherein (i) the first antigen binding moiety under a) and the second antigen binding moiety under b) are each fused at the C-terminus of the Fab heavy chain to the N-terminus of one of the subunits of the Fc domain under c).

In all of the different configurations of the bispecific antigen binding molecule according to the invention, the amino acid substitutions described herein, if present, may either be in the CH1 and CL domains of the first and (if present) the third antigen binding moiety/Fab molecule, or in the CH1 and CL domains of the second antigen binding moiety/Fab molecule. Preferably, they are in the CH1 and CL domains of the first and (if present) the third antigen binding moiety/Fab molecule. In accordance with the concept of the invention, if amino acid substitutions as described herein are made in the first (and, if present, the third) antigen binding moiety/Fab molecule, no such amino acid substitutions are made in the second antigen binding moiety/Fab molecule. Conversely, if amino acid substitutions as described herein are made in the second antigen binding moiety/Fab molecule, no such amino acid substitutions are made in the first (and, if present, the third) antigen binding moiety/Fab molecule. Amino acid substitutions are particularly made in bispecific antigen binding molecules comprising a Fab molecule wherein the variable domains VL and VH1 of the Fab light chain and the Fab heavy chain are replaced by each other.

In particular embodiments of the bispecific antigen binding molecule according to the invention, particularly wherein amino acid substitutions as described herein are made in the first (and, if present, the third) antigen binding moiety/Fab molecule, the constant domain CL of the first (and, if present, the third) Fab molecule is of kappa isotype. In other embodiments of the bispecific antigen binding molecule according to the invention, particularly wherein amino acid substitutions as described herein are made in the second antigen binding moiety/Fab molecule, the constant domain CL of the second antigen binding moiety/Fab molecule is of kappa isotype. In some embodiments, the constant domain CL of the first (and, if present, the third) antigen binding moiety/Fab molecule and the constant domain CL of the second antigen binding moiety/Fab molecule are of kappa isotype.

In one embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9;

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;

c) an Fc domain composed of a first and a second subunit;

wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) is fused at the C-terminus of the Fab heavy chain to the N-terminus of one of the subunits of the Fc domain under c), or (ii) the second antigen binding moiety under b) is fused at the C-terminus of the Fab heavy chain to the N-terminus of the Fab heavy chain of the first antigen binding moiety under a), and the first antigen binding moiety under a) is fused at the C-terminus of the Fab heavy chain to the N-terminus of one of the subunits of the Fc domain under c).

In a particular embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9:

b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other:

c) a third antigen binding moiety that binds to the first antigen and is identical to the first antigen binding moiety; and d) an Fc domain composed of a first and a second subunit:

wherein in the constant domain CL of the first antigen binding moiety under a) and the third antigen binding moiety under c) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) and the third antigen binding moiety under c) the amino acid at position 147 is substituted by glutamic acid (E) (numbering according to Kabat EU index) and the amino acid at position 213 is substituted by glutamic acid (E) (numbering according to Kabat EU index); and wherein (i) the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under c) are each fused at the C-terminus of the Fab heavy chain to the N-terminus of one of the subunits of the Fc domain under d), or (ii) the second antigen binding moiety under b) is fused at the C-terminus of the Fab heavy chain to the N-terminus of the Fab heavy chain of the first antigen binding moiety under a), and the first antigen binding moiety under a) and the third antigen binding moiety under c) are each fused at the C-terminus of the Fab heavy chain to the N-terminus of one of the subunits of the Fc domain under d).

In another embodiment, the invention provides a bispecific antigen binding molecule comprising a) a first antigen binding moiety that binds to a first antigen, wherein the first antigen is STEAP-1 and the first antigen binding moiety is a Fab molecule comprising a heavy chain variable region (VH) comprising a heavy chain complementary determining region (HCDR) 1 of SEQ ID NO: 1, a HCDR 2 of SEQ ID NO: 2, and a HCDR 3 selected from the group consisting of SEQ ID NO: 4, SEQ ID NO: 5 and SEQ ID NO: 6, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9, b) a second antigen binding moiety that binds to a second antigen, wherein the second antigen is an activating T cell antigen, particularly CD3, more particularly CD3 epsilon, and the second antigen binding moiety is a Fab molecule wherein the variable domains VL and VH of the Fab light chain and the Fab heavy chain are replaced by each other;

c) an Fc domain composed of a first and a second subunit;

wherein in the constant domain CL of the first antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first antigen binding moiety under a) the amino acid at position 147 is substituted by glutamic acid (E) (numbering according to Kabat EU index) and the amino acid at position 213 is substituted by glutamic acid (E) (numbering according to Kabat EU index); and wherein the first antigen binding moiety under a) and the second antigen binding moiety under b) are each fused at the C-terminus of the Fab heavy chain to the N-terminus of one of the subunits of the Fc domain under c).

According to any of the above embodiments, components of the bispecific antigen binding molecule (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

In a particular aspect, the invention provides a bispecific antigen binding molecule comprising a) a first and a third antigen binding moiety that binds to a first antigen; wherein the first antigen is STEAP-1 and wherein the first and the second antigen binding moiety are each a (conventional) Fab molecule comprising a heavy chain variable region comprising the amino acid sequence of SEQ ID NO: 13 and a light chain variable region comprising the amino acid sequence of SEQ ID NO: 14;

b) a second antigen binding moiety that binds to a second antigen; wherein the second antigen is CD3 and wherein the second antigen binding moiety is Fab molecule wherein the variable domains VL and VH of the Fab light chain and the Fab heavy chain are replaced by each other, comprising a heavy chain variable region comprising the amino acid sequence of SEQ ID NO: 21 and a light chain variable region comprising the amino acid sequence of SEQ ID NO: 22:

c) an Fc domain composed of a first and a second subunit; wherein in the constant domain CL of the first and the third antigen binding moiety under a) the amino acid at position 124 is substituted by lysine (K) (numbering according to Kabat) and the amino acid at position 123 is substituted by lysine (K) or arginine (R) (numbering according to Kabat) (most particularly by arginine (R)), and wherein in the constant domain CH1 of the first and the third antigen binding moiety under a) the amino acid at position 147 is substituted by glutamic acid (E) (numbering according to Kabat EU index) and the amino acid at position 213 is substituted by glutamic acid (E) (numbering according to Kabat EU index);

and wherein further the first antigen binding moiety under a) is fused at the C-terminus of the Fab heavy chain to the N-terminus of the Fab heavy chain of the second antigen binding moiety under b), and the second antigen binding moiety under b) and the third antigen binding moiety under a) are each fused at the C-terminus of the Fab heavy chain to the N-terminus of one of the subunits of the Fc domain under c).

In one embodiment according to this aspect of the invention, in the first subunit of the Fc domain the threonine residue at position 366 is replaced with a tryptophan residue (T366W), and in the second subunit of the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numberings according to Kabat EU index).

In a further embodiment according to this aspect of the invention, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index).

In still a further embodiment according to this aspect of the invention, in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In still a further embodiment according to this aspect of the invention, the Fc domain is a human $IgG_1$ Fc domain.

In particular specific embodiment, the bispecific antigen binding molecule comprises a polypeptide comprising an amino acid sequence that is at least 95%, 96%, 97%, 98%, or 99% identical to the sequence of SEQ ID NO: 32, a polypeptide comprising an amino acid sequence that is at least 95%, 96%, 97%, 98%, or 99;% identical to the sequence of SEQ ID NO: 33, a polypeptide comprising an amino acid sequence that is at least 95%, 96%, 97%, 98%, or 99% identical to the sequence of SEQ ID NO: 34, and a polypeptide comprising an amino acid sequence that is at least 95%, 96%, 97%, 98%, or 99% identical to the sequence of SEQ ID NO: 35. In a further particular specific embodiment, the bispecific antigen binding molecule comprises a polypeptide comprising the amino acid sequence of SEQ ID NO: 32, a polypeptide comprising the amino acid sequence of SEQ ID NO: 33, a polypeptide comprising the amino acid sequence of SEQ ID NO: 34 and a polypeptide comprising the amino acid sequence of SEQ ID NO: 35.

In another specific embodiment, the bispecific antigen binding molecule comprises a polypeptide comprising an amino acid sequence that is at least 95%, 96%, 97%, 98%, or 99% identical to the sequence of SEQ ID NO: 28, a polypeptide comprising an amino acid sequence that is at least 95%, 96%, 97%, 98%, or 99% identical to the sequence of SEQ ID NO: 29, a polypeptide comprising an amino acid sequence that is at least 95%, 96%, 97%, 98%, or 99% identical to the sequence of SEQ ID NO: 34, and a polypeptide comprising an amino acid sequence that is at least 95%, 96%, 97%, 98%, or 99% identical to the sequence of SEQ ID NO: 35. In a further specific embodiment, the bispecific antigen binding molecule comprises a polypeptide comprising the amino acid sequence of SEQ ID NO: 28, a polypeptide comprising the amino acid sequence of SEQ ID NO: 29, a polypeptide comprising the amino acid sequence of SEQ ID NO: 34 and a polypeptide comprising the amino acid sequence of SEQ ID NO: 35.

In still another specific embodiment, the bispecific antigen binding molecule comprises a polypeptide comprising an amino acid sequence that is at least 95%, 96%, 97%, 98%, or 99% identical to the sequence of SEQ ID NO: 30, a polypeptide comprising an amino acid sequence that is at least 95%, 96%, 97%, 98%, or 99% identical to the sequence of SEQ ID NO: 61, a polypeptide comprising an amino acid sequence that is at least 95%, 96%, 97%, 98%, or 99% identical to the sequence of SEQ ID NO: 34, and a polypeptide comprising an amino acid sequence that is at least 95%, 96%, 97%, 98%, or 99% identical to the sequence of SEQ ID NO: 35. In a further specific embodiment, the bispecific antigen binding molecule comprises a polypeptide comprising the amino acid sequence of SEQ ID NO: 30, a polypeptide comprising the amino acid sequence of SEQ ID NO: 31, a polypeptide comprising the amino acid sequence of SEQ ID NO: 34 and a polypeptide comprising the amino acid sequence of SEQ ID NO: 35.

Fc Domain

In particular embodiments, the bispecific antigen binding molecule of the invention comprises an Fc domain composed of a first and a second subunit. It is understood, that the features of the Fc domain described herein in relation to the bispecific antigen binding molecule can equally apply to an Fc domain comprised in an antibody of the invention.

The Fc domain of the bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment, the bispecific antigen binding molecule of the invention comprises not more than one Fc domain.

In one embodiment, the Fc domain of the bispecific antigen binding molecule is an IgG Fc domain.

In a particular embodiment, the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat EU index numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)).

In a further particular embodiment, the Fc domain is a human Fc domain. In an even more particular embodiment, the Fc domain is a human $IgG_1$ Fc domain. An exemplary sequence of a human $IgG_1$ Fc region is given in SEQ ID NO: 36.

Fc Domain Modifications Promoting Heterodimerization

Bispecific antigen binding molecules according to the invention comprise different antigen binding moieties, which may be fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of bispecific antigen binding molecules in recombinant production, it will thus be advantageous to introduce in the Fc domain of the bispecific antigen binding molecule a modification promoting the association of the desired polypeptides.

Accordingly, in particular embodiments, the Fc domain of the bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011. WO 98/050431, EP 1870459, WO 2007/110205, WO 2007/147901, WO 2009/089004. WO 2010/129304, WO 2011/90754, WO 2011/143545, WO 2012058768, WO 2013157954. WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (e.g. VH and VL exchange/replacement in one binding arm and the introduction of substitutions of charged amino acids with opposite charges in the CH1/CL interface) in the bispecific antigen binding molecule which reduce heavy/light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter. J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in (the CH3 domain of) the first subunit of the Fc domain (the "knobs" subunit) the threonine residue at position 366 is replaced with a tryptophan residue (T366W), and in (the CH3 domain of) the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises the amino acid substitutions S354C and T366W, and the second subunit of the Fc domain comprises the amino acid substitutions Y349C, T366S, L368A and Y407V (numbering according to Kabat EU index). In a particular embodiment the antigen binding moiety that binds to the second antigen (e.g. an activating T cell antigen) is fused (optionally via the first antigen binding moiety, which binds to STEAP-1, and/or a peptide linker) to the first subunit of the Fc domain (comprising the "knob" modification). Without wishing to be bound by theory, fusion of the antigen binding moiety that binds a second antigen, such as an activating T cell antigen, to the knob-containing subunit of the Fc domain will (further) minimize the generation of antigen binding molecules comprising two antigen binding moieties that bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment, the heterodimerization approach described in EP 1870459, is used alternatively. This approach is based on the introduction of charged amino acids with opposite charges at specific amino acid positions in the CH3/CH3 domain interface between the two subunits of the Fc domain. One preferred embodiment for the bispecific antigen binding molecule of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment, the bispecific antigen binding molecule of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment, the bispecific antigen binding molecule of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said bispecific antigen binding molecule comprises amino acid mutations Y349C, T366W in the CH3 domain of the first subunit of the Fc domain and amino acid mutations S354C. T366S, L368A, Y407V in the CH3 domains of the second subunit of the Fc domain and additionally amino acid mutations R409D: K370E in the CH3 domain of the first subunit of the Fc domain and amino acid mutations D399K; E357K in the CH3 domain of the second subunit of the Fc domain (all numberings according to Kabat EU index).

In one embodiment, the heterodimerization approach described in WO 2013/157953 is used alternatively. In one embodiment, a first CH3 domain comprises amino acid mutation T366K and a second CH3 domain comprises amino acid mutation L351D (numberings according to Kabat EU index). In a further embodiment, the first CH3 domain comprises further amino acid mutation L351K. In a further embodiment, the second CH3 domain comprises further an amino acid mutation selected from Y349E, Y349D and L368E (preferably L368E) (numberings according to Kabat EU index).

In one embodiment, the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, S400, F405, N390, or K392, e.g. selected from a) T411 N, T411R, T411Q, T411K, T411 D, T411E or T411W, b) D399R, D399W, D399Y or D399K, c) S400E, S400D, S400R, or S400K, d) F405I, F405M, F405T, F405S, F405V or F405W, e) N390R. N390K or N390D, f) K392V. K392M, K392R, K392L, K392F or K392E (numberings according to Kabat EU index). In a further embodiment a first CH3 domain comprises amino acid mutations L351Y, Y407A and a second CH3 domain comprises amino acid mutations T366V. K409F. In a further embodiment, a first CH3 domain comprises amino acid mutation Y407A and a second CH3 domain comprises amino acid mutations T366A, K409F. In a further embodiment, the second CH3 domain further comprises amino acid mutations K392E, T411 E, D399R and S400R (numberings according to Kabat EU index).

In one embodiment, the heterodimerization approach described in WO 2011/143545 is used alternatively. e.g. with the amino acid modification at a position selected from the group consisting of 368 and 409 (numbering according to Kabat EU index).

In one embodiment, the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (numberings according to Kabat EU index).

In one embodiment, the bispecific antigen binding molecule or its Fc domain is of $IgG_2$ subclass and the heterodimerization approach described in WO 2010/129304 is used alternatively.

In an alternative embodiment, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment, the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (numberings according to Kabat EU index).

In still another embodiment, the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the bispecific antigen binding molecule (or the antibody) favorable pharmacokinetic properties, including a long serum half-life which contributes to good accumulation in the target tissue and a favorable tissue-blood distribution ratio. At the same time it may, however, lead to undesirable targeting of the bispecific antigen binding molecule (or the antibody) to cells expressing Fc receptors rather than to the preferred antigen-bearing cells. Moreover, the co-activation of Fc receptor signaling pathways may lead to cytokine release which, in combination with the T cell activating properties (e.g. in embodiments of the bispecific antigen binding molecule wherein the second antigen binding moiety binds to an activating T cell antigen) and the long half-life of the bispecific antigen binding molecule, results in excessive activation of cytokine receptors and severe side effects upon systemic administration. Activation of (Fc receptor-bearing) immune cells other than T cells may even reduce efficacy of the bispecific antigen binding molecule (particularly a bispecific antigen binding molecule wherein the second antigen binding moiety binds to an activating T cell antigen) due to the potential destruction of T cells e.g. by NK cells.

Accordingly, in particular embodiments, the Fc domain of the bispecific antigen binding molecule according to the invention exhibits reduced binding affinity to an Fc receptor and/or reduced effector function, as compared to a native $IgG_1$ Fc domain. In one such embodiment the Fc domain (or the bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain (or a bispecific antigen binding molecule comprising a native $IgG_1$ Fc domain). In one embodiment, the Fc domain (or the bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment, the effector function is ADCC. In one embodiment, the Fc domain exhibits substantially similar binding affinity to neonatal Fc receptor (FcRn), as compared to a native $IgG_1$ Fc domain. Substantially similar binding to FcRn is achieved when the Fc domain (or the bispecific antigen binding molecule comprising said Fc domain) exhibits greater than about 70%, particularly greater than about 80%, more particularly greater than about 90% of the binding affinity of a native $IgG_1$ Fc domain (or the bispecific antigen binding molecule comprising a native $IgG_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment, the amino acid mutation reduces the binding affinity of the Fc domain to an Fc receptor. In one embodiment, the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the bispecific antigen binding molecule comprising an engineered Fc domain exhibits less than 20%, particularly less than 10%, more particularly less than 5% of the binding affinity to an Fc receptor as compared to a bispecific antigen binding molecule comprising a non-engineered Fc domain. In a particular embodiment, the Fc receptor is an Fcγ receptor. In some embodiments, the Fc receptor is a human Fc receptor. In some embodiments, the Fc receptor is an activating Fc receptor. In a specific embodiment, the Fc receptor is an activating human Fcγ receptor, more specifically human FcγRIIIa, Fc-γRI or FcγRIIa, most specifically human FcγRIIIa. Preferably, binding to each of these receptors is reduced. In some embodiments, binding affinity to a complement component, specifically binding affinity to C1q, is also reduced. In one embodiment, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule comprising said Fc domain) exhibits greater than about 70% of the binding affinity of a non-engineered form of the Fc domain (or the bispecific antigen binding molecule comprising said non-engineered form of the Fc domain) to FcRn. The Fc domain, or bispecific antigen binding molecules of the invention comprising said Fc domain, may exhibit greater than about 80% and even greater than about 90% of such affinity. In certain embodiments, the Fc domain of the bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced cross-linking of target-bound antibodies, reduced dendritic cell maturation, or reduced T cell priming. In one embodiment, the reduced effector function is one or more selected from the group of reduced CDC, reduced ADCC, reduced ADCP, and reduced cytokine secretion. In a particular embodiment, the reduced effector function is reduced ADCC. In one embodiment the reduced ADCC is less than 20% of the ADCC induced by a non-engineered Fc domain (or a bispecific antigen binding molecule comprising a non-engineered Fc domain).

In one embodiment, the amino acid mutation that reduces the binding affinity of the Fc domain to an Fc receptor and/or effector function is an amino acid substitution. In one embodiment, the Fc domain comprises an amino acid substitution at a position selected from the group of E233, L234, L235, N297, P331 and P329 (numberings according to Kabat EU index). In a more specific embodiment, the Fc domain comprises an amino acid substitution at a position selected from the group of L234, L235 and P329 (numberings according to Kabat EU index). In some embodiments, the Fc domain comprises the amino acid substitutions L234A and L235A (numberings according to Kabat EU index). In one such embodiment, the Fc domain is an $IgG_1$ Fc domain, particularly a human $IgG_1$ Fc domain. In one embodiment, the Fc domain comprises an amino acid substitution at position P329. In a more specific embodiment, the amino acid substitution is P329A or P329G, particularly P329G (numberings according to Kabat EU index). In one embodiment, the Fc domain comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc domain comprises amino acid substitutions at positions P329, L234 and L235 (numberings according to Kabat EU index). In more particular embodiments, the Fc domain comprises the amino acid mutations L234A, L235A and P329G ("P329G LALA", "PGLALA" or "LALAPG"). Specifically, in particular embodiments, each subunit of the Fc domain comprises the amino acid substitutions L234A, L235A and P329G (Kabat EU index numbering), i.e. in each of the first and the second subunit of the Fc domain the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, which is incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some embodiments, the Fc domain of the bispecific antigen binding molecules of the invention is an $IgG_4$ Fc domain, particularly a human $IgG_4$ Fc domain. In one embodiment, the $IgG_4$ Fc domain comprises amino acid substitutions at position S228, specifically the amino acid substitution S228P (numberings according to Kabat EU index). To further reduce its binding affinity to an Fc receptor and/or its effector function, in one embodiment, the $IgG_4$ Fc domain comprises an amino acid substitution at position L235, specifically the amino acid substitution L235E (numberings according to Kabat EU index). In another embodiment, the $IgG_4$ Fc domain comprises an amino acid substitution at position P329, specifically the amino acid substitution P329G (numberings according to Kabat EU index). In a particular embodiment, the $IgG_4$ Fc domain comprises amino acid substitutions at positions S228, L235 and P329, specifically amino acid substitutions S228P, L235E and P329G (numberings according to Kabat EU index). Such $IgG_4$ Fc domain mutants and their Fcγ receptor binding properties are described in PCT publication no. WO 2012/130831, incorporated herein by reference in its entirety.

In a particular embodiment, the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A and optionally P329G, or a human $IgG_4$ Fc domain comprising the amino acid substitutions S228P, L235E and optionally P329G (numberings according to Kabat EU index).

In certain embodiments, N-glycosylation of the Fc domain has been eliminated. In one such embodiment, the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. Alternatively, binding affinity of Fc domains or bispecific antigen binding molecules comprising an Fc domain for Fc receptors may be evaluated using cell lines known to express particular Fc receptors, such as human NK cells expressing FcγIIIa receptor.

Effector function of an Fc domain, or a bispecific antigen binding molecule comprising an Fc domain, can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega. Madison. Wis.)). Useful effector cells for such assays include peripheral blood mononuclear cells (PBMC) and Natural Killer (NK) cells. Alternatively. or additionally. ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or the bispecific antigen binding molecule comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie. Blood 103, 2738-2743 (2004)).

FcRn binding and in vivo clearance/half life determinations can also be performed using methods known in the art (see, e.g., Petkova, S. B. et al., *Int'l. Immunol.* 18(12):1759-1769 (2006); WO 2013/120929).

Polynucleotides

The invention further provides isolated polynucleotides encoding an antibody or bispecific antigen binding molecule as described herein or a fragment thereof. In some embodiments, said fragment is an antigen binding fragment.

The polynucleotides encoding antibodies or bispecific antigen binding molecules of the invention may be expressed as a single polynucleotide that encodes the entire antibody or bispecific antigen binding molecule or as multiple (e.g., two or more) polynucleotides that are co-expressed.

Polypeptides encoded by polynucleotides that are co-expressed may associate through, e.g., disulfide bonds or other means to form a functional antibody or bispecific antigen binding molecule. For example, the light chain portion of an antibody or bispecific antigen binding molecule may be encoded by a separate polynucleotide from the portion of the antibody or bispecific antigen binding molecule comprising the heavy chain of the antibody or bispecific antigen binding molecule. When co-expressed, the heavy chain polypeptides will associate with the light chain polypeptides to form the antibody or bispecific antigen binding molecule. In another example, the portion of the antibody or bispecific antigen binding molecule comprising one of the two Fc domain subunits and optionally (part of) one or more Fab molecules could be encoded by a separate polynucleotide from the portion of the antibody or bispecific antigen binding molecule comprising the other of the two Fc domain subunits and optionally (part of) a Fab molecule. When co-expressed, the Fc domain subunits will associate to form the Fc domain.

In some embodiments, the isolated polynucleotide encodes the entire antibody or bispecific antigen binding molecule according to the invention as described herein. In other embodiments, the isolated polynucleotide encodes a polypeptide comprised in the antibody or bispecific antigen binding molecule according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antibodies or bispecific antigen binding molecules of the invention may be obtained, for example, by solid-state peptide synthesis (e.g. Merrifield solid phase synthesis) or recombinant production. For recombinant production one or more polynucleotide encoding the antibody or bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an antibody or bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., *MOLECULAR CLONING: A LABORATORY MANUAL*, Cold Spring Harbor Laboratory. N.Y. (1989); and Ausubel et al., *CURRENT PROTOCOLS IN MOLECULAR BIOLOGY*, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody or bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody or bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody or bispecific antigen binding molecule is desired, DNA encoding a signal sequence may be placed upstream of the nucleic acid encoding an antibody or bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the antibody or bispecific antigen binding molecule may be included within or at the ends of the antibody or bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) one or more vector comprising one or more polynucleotide that encodes (part of) an antibody or bispecific antigen binding molecule of the invention. As used herein, the term "host cell" refers to any kind of cellular system which can be engineered to generate the antibody or bispecific antigen binding molecule of the invention or fragments thereof. Host cells suitable for replicating and for supporting expression of antibodies or bispecific antigen binding molecules are well known in the art. Such cells may be transfected or transduced as appropriate with the particular expression vector and large quantities of vector containing cells can be grown for seeding large scale fermenters to obtain sufficient quantities of the antibody or bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TR1 cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77,4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing an antibody or bispecific antigen binding molecule according to the invention is provided, wherein the method comprises culturing a host cell comprising a polynucleotide encoding the antibody or bispecific antigen binding molecule, as provided herein, under conditions suitable for expression of the antibody or bispecific antigen binding molecule, and optionally recovering the antibody or bispecific antigen binding molecule from the host cell (or host cell culture medium).

The components of the bispecific antigen binding molecule (or the antibody) of the invention may be genetically fused to each other. The bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are provided herein. Additional sequences may also be included to incorporate a cleavage site to separate the individual components of the fusion if desired, for example an endopeptidase recognition sequence.

The antibody or bispecific antigen binding molecule of the invention generally comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region may be used in the antibody or bispecific antigen binding molecule of the invention. Non-limiting antibodies, antibody fragments, antigen binding domains or variable regions useful in the present invention can be of murine, primate, or human origin. If the antibody or bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J Cancer,* 83:252-260 (2000) (describing the "guided selection" approach to FR shuffling). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human antibodies can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology: U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified. e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boemer et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolation from human antibody libraries, as described herein.

Antibodies useful in the invention may be isolated by screening combinatorial libraries for antibodies with the desired activity or activities. Methods for screening combinatorial libraries are reviewed, e.g., in Lerner et al. in *Nature Reviews* 16.498-508 (2016). For example, a variety of methods are known in the art for generating phage display libraries and screening such libraries for antibodies possessing the desired binding characteristics. Such methods are reviewed, e.g., in Frenzel et al. in *mAbs* 8:1177-1194 (2016); Bazan et al. in *Human Vaccines and Immunotherapeutics* 8:1817-1828 (2012) and Zhao et al. in *Critical Reviews in Biotechnology* 36:276-289 (2016) as well as in Hoogenboom et al. in *Methods in Molecular Biology* 178:1-37 (O'Brien et al., ed., Human Press, Totowa, N.J., 2001) and in Marks and Bradbury in *Methods in Molecular Biology* 248:161-175 (Lo, ed., Human Press, Totowa, N.J., 2003).

In certain phage display methods, repertoires of VH and VL genes are separately cloned by polymerase chain reaction (PCR) and recombined randomly in phage libraries, which can then be screened for antigen-binding phage as described in Winter et al. in *Annual Review of Immunology* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. in *EMBO Journal* 12: 725-734 (1993). Finally, naïve libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter in *Journal of Molecular Biology* 227: 381-388 (1992). Patent publications describing human antibody phage libraries include, for example: U.S. Pat. Nos. 5,750,373; 7,985,840; 7,785,903 and 8,679,490 as well as US Patent Publication Nos. 2005/0079574, 2007/0117126, 2007/0237764 and 2007/0292936. Further examples of methods known in the art for screening combinatorial libraries for antibodies with a desired activity or activities include ribosome and mRNA display, as well as methods for antibody display and selection on bacteria, mammalian cells, insect cells or yeast cells. Methods for yeast surface display are reviewed, e.g., in Scholler et al. in *Methods in Molecular Biology* 503:135-56 (2012) and in Cherf et al. in *Methods in Molecular biology* 1319:155-175 (2015) as well as in the Zhao et al. in *Methods in Molecular Biology* 889:73-84 (2012). Methods for ribosome display are described, e.g., in He et al. in *Nucleic Acids Research* 25:5132-5134 (1997) and in Hanes et al. in *PNAS* 94:4937-4942 (1997).

Antibodies or bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification, an antibody, ligand, receptor or antigen can be used to which the antibody or bispecific antigen binding molecule binds. For example, for affinity chromatography purification of antibodies or bispecific antigen binding molecules of the invention, a matrix with protein A or protein G may be used. Sequential Protein A or G affinity chromatography and size exclusion chromatography can be used to isolate an antibody or bispecific antigen binding molecule essentially as described in the Examples. The purity of the antibody or bispecific antigen binding molecule can be determined by any of a variety of well known analytical methods including gel electrophoresis, high pressure liquid chromatography, and the like.

Assays

Antibodies or bispecific antigen binding molecules provided herein may be identified, screened for, or characterized for their physical/chemical properties and/or biological activities by various assays known in the art.

Affinity Assays

The affinity of the antibody or bispecific antigen binding molecule for an Fc receptor or a target antigen can be determined for example by surface plasmon resonance (SPR), using standard instrumentation such as a BIAcore instrument (GE Healthcare), and receptors or target proteins such as may be obtained by recombinant expression. Alternatively, binding of antibodies or bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following.

According to one embodiment. $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the antibody or bispecific antigen binding molecule (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, antibodies or bispecific antigen binding molecules are captured by an anti human Fab specific antibody (GE Healthcare) that is immobilized on an activated CM5-sensor chip surface as described for the anti Penta-His antibody. The final amount of coupled protein is approximately 12000 RU. The, antibodies or bispecific antigen binding molecules are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the bispecific antigen binding molecules (or antibodies) of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the antibodies or bispecific antigen binding molecules provided herein, e.g., for use in any of the below therapeutic methods. In one embodiment, a pharmaceutical composition comprises any of the antibodies or bispecific antigen binding molecules provided herein and a pharmaceutically acceptable carrier. In another embodiment, a pharmaceutical composition comprises any of the antibodies or bispecific antigen binding molecules provided herein and at least one additional therapeutic agent, e.g., as described below.

Further provided is a method of producing an antibody or bispecific antigen binding molecule of the invention in a form suitable for administration in vivo, the method comprising (a) obtaining an antibody or bispecific antigen binding molecule according to the invention, and (b) formulating the antibody or bispecific antigen binding molecule with at least one pharmaceutically acceptable carrier, whereby a preparation of antibody or bispecific antigen binding molecule is formulated for administration in vivo.

Pharmaceutical compositions of the present invention comprise a therapeutically effective amount of antibody or bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains an antibody or bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

An antibody or bispecific antigen binding molecule of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic.

Parenteral compositions include those designed for administration by injection, e.g. subcutaneous, intradermal, intralesional, intravenous, intraarterial intramuscular, intrathecal or intraperitoneal injection. For injection, the antibodies or bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the antibodies or bispecific antigen binding molecules may be in powder form for constitution with a suitable vehicle, e.g., sterile pyrogen-free water, before use. Sterile injectable solutions are prepared by incorporating the antibodies or bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids: antioxidants including ascorbic acid and methionine; preservatives (such as octadecyldimethylbenzyl ammonium chloride; hexamethonium chloride: benzalkonium chloride; benzethonium chloride; phenol, butyl or benzyl alcohol; alkyl parabens such as methyl or propyl paraben: catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone: amino acids such as glycine, glutamine, asparagine, histidine, arginine, or lysine; monosaccharides, disaccharides, and other carbohydrates including glucose, mannose, or dextrins; chelating agents such as EDTA: sugars such as sucrose, mannitol, trehalose or sorbitol; salt-forming counter-ions such as sodium, metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the antibodies or bispecific antigen binding molecules may also be formulated as a depot preparation. Such long acting formulations may be administered by implantation (for example subcutaneously or intramuscularly) or by intramuscular injection. Thus, for example, the antibodies or bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies or bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies or bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or w % bich are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the antibodies or bispecific antigen binding molecules provided herein may be used in therapeutic methods. Antibodies or bispecific antigen binding molecules of the invention may be used as immunotherapeutic agents, for example in the treatment of cancers.

For use in therapeutic methods, antibodies or bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies or bispecific antigen binding molecules of the invention for use as a medicament are provided. In further aspects, antibodies or bispecific antigen binding molecules of the invention for use in treating a disease are provided. In certain embodiments, antibodies or bispecific antigen binding molecules of the invention for use in a method of treatment are provided. In one embodiment, the invention provides an antibody or bispecific antigen binding molecule as described herein for use in the treatment of a disease in an individual in need thereof. In certain embodiments, the invention provides an antibody or bispecific antigen binding molecule for use in a method of treating an individual having a disease comprising administering to the individual a therapeutically effective amount of the antibody or bispecific antigen binding molecule. In certain embodiments the disease to be treated is a proliferative disorder. Ina particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides an antibody or bispecific antigen binding molecule as described herein for use in inducing lysis of a target cell, particularly a tumor cell. In certain embodiments, the invention provides an antibody or bispecific antigen binding molecule for use in a method of inducing lysis of a target cell, particularly a tumor cell, in an individual comprising administering to the individual an effective amount of the antibody or bispecific antigen binding molecule to induce lysis of a target cell. An "individual" according to any of the above embodiments is a mammal, preferably a human.

In a further aspect, the invention provides for the use of an antibody or bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of an antibody or bispecific antigen binding molecule of the invention. In one embodiment a composition is administered to said individual, comprising the antibody or bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with an antibody or bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of an antibody or bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that may be treated using an antibody or bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of kidney cancer, bladder cancer, skin cancer, lung cancer, colorectal cancer, breast cancer, brain cancer, head and neck cancer and prostate cancer. In one embodiment, the cancer is prostate cancer. A skilled artisan readily recognizes that in many cases the antibody or bispecific antigen binding molecule may not provide a cure but may only provide partial benefit. In some embodiments, a physiological change having some benefit is also considered therapeutically beneficial. Thus, in some embodiments, an amount of antibody or bispecific antigen binding molecule that provides a physiological change is considered an "effective amount" or a "therapeutically effective amount". The subject, patient, or individual in need of treatment is typically a mammal, more specifically a human.

In some embodiments, an effective amount of an antibody or bispecific antigen binding molecule of the invention is administered to a cell. In other embodiments, a therapeutically effective amount of an antibody or bispecific antigen binding molecule of the invention is administered to an individual for the treatment of disease.

For the prevention or treatment of disease, the appropriate dosage of an antibody or bispecific antigen binding molecule of the invention (when used alone or in combination with one or more other additional therapeutic agents) will depend on the type of disease to be treated, the route of administration, the body weight of the patient, the type of antibody or bispecific antigen binding molecule, the severity and course of the disease, whether the antibody or bispecific antigen binding molecule is administered for preventive or therapeutic purposes, previous or concurrent therapeutic interventions, the patient's clinical history and response to the antibody or bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antibody or bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of antibody or bispecific antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently. e.g. every week or every three weeks (e.g. such that the patient receives from about two to about twenty, or e.g. about six doses of the antibody or bispecific antigen binding molecule). An initial higher loading dose, followed by one or more lower doses may be administered. However, other dosage regimens may be useful. The progress of this therapy is easily monitored by conventional techniques and assays.

The antibodies or bispecific antigen binding molecules of the invention will generally be used in an amount effective to achieve the intended purpose. For use to treat or prevent a disease condition, the antibodies or bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data. e.g., animal models, using techniques that are well known in the art. One having ordinary skill in the art could readily optimize administration to humans based on animal data.

Dosage amount and interval may be adjusted individually to provide plasma levels of the antibodies or bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the antibodies or bispecific antigen binding molecules may not be related to plasma concentration. One having skill in the art will be able to optimize therapeutically effective local dosages without undue experimentation.

A therapeutically effective dose of the antibodies or bispecific antigen binding molecules described herein will generally provide therapeutic benefit without causing substantial toxicity. Toxicity and therapeutic efficacy of an antibody or bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies or bispecific antigen binding molecules that exhibit large therapeutic indices are preferred. In one embodiment, the antibody or bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in; The Pharmacological Basis of Therapeutics. Ch. 1, p. 1, incorporated herein by reference in its entirety).

The attending physician for patients treated with antibodies or bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The antibodies and bispecific antigen binding molecules of the invention may be administered in combination with one or more other agents in therapy. For instance, an antibody or bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. Such other agents are suitably present in combination in amounts that are effective for the purpose intended. The effective amount of such other agents depends on the amount of antibody or bispecific antigen binding molecule used, the type of disorder or treatment, and other factors discussed above. The antibodies or bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody or bispecific antigen binding molecule of the invention can occur prior to, simultaneously, and/or following, administration of the additional therapeutic agent and/or adjuvant. Antibodies or bispecific antigen binding molecules of the invention may also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or bispecific antigen binding molecule of the invention. The label or package insert indicates that the composition is used for treating the condition of choice. Moreover, the article of manufacture may comprise (a) a first container with a composition contained therein, wherein the composition comprises an antibody or bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringers solution and dextrose solution. It may further include other materials desirable from a commercial and user standpoint, including other buffers, diluents, filters, needles, and syringes.

Methods and Compositions for Diagnostics and Detection

In certain embodiments, any of the anti-STEAP-1 antibodies provided herein is useful for detecting the presence of STEAP-1 in a biological sample. The term "detecting" as used herein encompasses quantitative or qualitative detection. In certain embodiments, a biological sample comprises a cell or tissue, such as prostate tissue.

In one embodiment, an anti-STEAP-1 antibody for use in a method of diagnosis or detection is provided. In a further aspect, a method of detecting the presence of STEAP-1 in a biological sample is provided. In certain embodiments, the method comprises contacting the biological sample with an anti-STEAP-1 antibody as described herein under conditions permissive for binding of the anti-STEAP-1 antibody to STEAP-1, and detecting whether a complex is formed between the anti-STEAP-1 antibody and STEAP-1. Such method may be an in vitro or in vivo method. In one embodiment, an anti-STEAP-1 antibody is used to select subjects eligible for therapy with an anti-STEAP-1 antibody, e.g. where STEAP-1 is a biomarker for selection of patients.

Exemplary disorders that may be diagnosed using an antibody of the invention include cancer, particularly prostate cancer.

In certain embodiments, labeled anti-STEAP-1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases. e.g., firefly luciferase and bacterial luciferase (U.S. Pat. No. 4,737,456), luciferin, 2,3-dihydrophthala-rinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

| | Amino Acid Sequences | |
|---|---|---|
| | Amino Acid Sequence | SEQ ID NO |
| STEAP-1 HCDR1 | SDYAWN | 1 |
| STEAP-2 HCDR2 | YSINSGSTSYNPSLKS | 2 |
| STEAP-1 HCDR3 (DD) | ERYNYDYDDYYYAMDY | 3 |
| STEAP-1 HCDR3 (ED) | ERNYDYEDYYYAMDY | 4 |
| STEAP-1 HCDR3 (DE) | ERNYDYDEYYYAMDY | 5 |
| STEAP-1 HCDR3 (EE) | ERNYDYEEYYYAMDY | 6 |
| STEAP-1 LCDR1 | KSSQSLLYRSNQKNYLA | 7 |
| STEAP-1 LCDR2 | WASTRES | 8 |
| STEAP-1 LCDR3 | QQYYNYPRT | 9 |
| STEAP-1 | EVQLVESGGGLVQPGGSLRLSCAVSGYSITSDYAWNWVRQAPGKGLEW | 10 |

-continued

Amino Acid Sequences

| | Amino Acid Sequence | SEQ ID NO |
|---|---|---|
| VH (DD) | VGYISNSGSTSYNPSLKSRFTISRDTSKNTLYLQMNSLRAEDTAVYYC ARERNYDYDDYYYAMDYWGQGTLVTVSS | |
| STEAP-1 VH (ED) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYEDYYYAMDYWGQGTLVTVSS | 11 |
| STEAP-1 VH (DE) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYDEYYYAMDYWGQGTLVTVSS | 12 |
| STEAP-1 VH (EE) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYEEYYYAMDYWGQGTLVTVSS | 13 |
| STEAP-1 VL | DIQMTQSPSSLSASVGDRVTITCKSSQSLLYRSNQKNYLAWYQQKPGK APKLLIYWASTRESGVPSRFSGSGSGTDFTLTISSLQPEDFATYYCQQ YYNYPRTFGQGTKVEIK | 14 |
| CD3 HCDR1 | TYAMN | 15 |
| CD3 HCDR2 | RIRSKYNNYATYYADSVKG | 16 |
| CD3 HCDR3 | HGNFGNSYVSWFAY | 17 |
| CD3 LCDR1 | GSSTGAVTTSNYAN | 18 |
| CD3 LCDR2 | GTNKRAP | 19 |
| CD3 LCDR3 | ALWYSNLWV | 20 |
| CD3 VH | EVQLLESGGGLVQPGGSLRLSCAASGFTFSTYAMNWVRQAPGKGLEWV SRIRSKYNNYATYYADSVKGRFTISRDDSKNTLYLQMNSLRAEDTAVY YCVRHGNFGNSYVSWFAYWGQGTLVTVSS | 21 |
| CD3 VL | QAVVTQEPSLTVSPGGTVTLTCGSSTGAVTTSNYANWVQEKPGQAFRG LIGGTNKRAPGTPARFSGSLLGGKAALTLSGAQPEDEAEYYCALWYSN LWVFGGGTKLTVL | 22 |
| hSTEAP-1 | MESRKDITNQEELWKMKPRRNLEEDDYLHKDTGETSMLKRPVLLHLHQ TAHADEFDCPSELQHTQELFPQWHLPIKIAAIIASLTFLYTLLREVIH PLATSHQQYFYKIPILVINKVLPMVSITLLALVYLPGVIAAIVQLHNG TKYKKFPHWLDKWMLTRKQFGLLSFFFAVLHAIYSLSYPMRRSYRYKL LNWAYQQVQQNKEDAWIEHDVWRMEIYVSLGIVGLAILALLAVTSIPS VSDSLTWREFHYIQSKLGIVSLLLGTIHALIFAWNKWIDIKQFVWYTP PTFMIAVFLPIVVLIFKSILFLPCLRKKILKIRHGWEDVTKINKTEIC SQL | 23 |
| hCD3 | MQSGTHWRVLGLCLLSVGVWGQDGNEEMGGITQTPYKVSISGTTVILT CPQYGPSEILWQHNDKNIGGDEDDKNIGSDEDHLSLKEFSELEQSGYY VCYPRGSKPEDANFYLYLRARVCENCMEMDVMSVATIVIVDICITGGL LLLVYYWSKNRKAKAKPVTRGAGAGGRQRGQNKERPPPVPNPDYEPIR KGQRDLYSGLNQRRI | 24 |
| cynoCD3 | MQSGTRWRVLGLCLLSIGVWGQDGNEEMGSITQTPYQVSISGTTVILT CSQHLGSEAQWQHNGKNKEDSGDRLFLPEFSEMEQSGYYVCYPRGSNP EDASHHLYLKARVCENCMEMDVMAVATIVIVDICITLGLLLLVYYWSK NRKAKAKPVTRGAGAGGRQRGQNKERPPPVPNPDYEPIRKGQQDLYSG LNQRRI | 25 |
| Molecule A (STEAP-1 VH-(CH1(EE)-Fc(knob, PGLALA)) | EVLQVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYDDYYYAMDYWGQGTLVTVSSASTKGPSVFPLAPSSKSTSG GTAALGCLVEDYFPEPVTVSWNSGALTSGVHTFPAVLQSSGLYSLSSV VTVPSSSLGTQTYICNVNHKPSNTKVDEKVEPKSCDKTHTCPPCPAPE AAGGPSVFLFPPKPKDTLMISRTPEVTCVVVDVSHEDPEVKFNWYVDG | 26 |

-continued

| | Amino Acid Sequences | |
|---|---|---|
| | Amino Acid Sequence | SEQ ID NO |
| | VEVHNAKTKPREEQYNSTYRVVSVLTVLHQDWLNGKEYKCKVSNKALG APIEKTISKAKGQPREPQVCTLPPSRDELTKNQVSLSLCAVKGFYPSD IAVEWESNGQPENNYKTTPPVLDSDGSFFLVSKLTVDKSRWQQGNVFS CSVMHEALHNHYTQKSLSLSP | |
| Molecule A (STEAP-1 VH-CH1(EE)-CD3 VL-CH1-Fc(knob), PGLALA)) | EVLQVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYDDYYYAMDYWGQGTLVTVSSASTKGPSVFPLAPSSKSTSG GTAALGCLVEDYFPEPVTVSWNSGALTSGVHTFPAVLQSSGLYSLSSV VTVPSSSLGTQTYICNVNHKPSNTKVDEKVEPKSCDGGGSGGGGSQA VVTQEPSLTVSPGGTVTLTCGSSTGAVTTSNYANWVQEKPGQAFRGLI GGTNKRAPGTPARFSGSLLGGKAALTLSGAQPEDEAEYYCALWYSNLW VFGGGTKLTVLSSASTKGPSVFPLAPSSKSTSGGTAALGCLVKDYFPE PVTVSWNSGALTSGVHTFPAVLQSSGLYSLSSVVTVPSSSLGTQTYIC NVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQY NSTYRVVSVLTVLHQDWLNGKEYKCKVSNKALGAPIEKTISKAKGQPR EPQVYTLPPCRDELTKNQVSLWCLVKGFYPSDIAVEWESNGQPENNYK TTPPVLDSDGSFFLYSKLTVDKSRWQQGNVFSCSVMHEALHNHYTQKS LSLSP | 27 |
| Molecule B (STEAP-1 VH-CH1(EE)- Fc(knob), PGLALA)) | EVQLVESGGGLVQPGGSLRLSCASSGYSITSDYQWNWVRQAPGKGLEW VGYISNSGSTSYNPSLKSRFTISRDTSKNTLYLQMNSLRAEDTAVYYC ARERNYDYEDYYYAMDYWGQGTLVTVSSASTKGPSVFPLAPSSKSTSG GTAALGCLVEDYFPEPVTVSWNSGALTSGVHTFPAVLQSSGLYSLSSV VTVPSSSLGTQTYICNVNHKPSNTKVDEKVEPKSCDKTHTCPPCPAPE AAGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALG APIEKTISKAKGQPREPQVCTLPPSRDELTKNQVSLSCACKGFYPSDI AVEWESNGQPENNYKTTPPVLDSDGSFFLVSKLTVDKSRWQQGNVFSC SVMHEALHNHYTQKSLSLSP | 28 |
| Molecule B (STEAP-1 VH-CH1(EE)-CD3 VL-CH1-Fc(knob), PGLALA)) | EVQLVESGGGLVQPGGSLRLSCAVSGYSITSDYSWNWVRQAPGKGLEW VGYISNSGSTSYNPSLKSRFTISRDTSKNTLYLQMNSLRAEDTAVYYC ARERNYDYEDYYYAMDYWGQGTLVTVSSASTKGPSVFPLAPSSKSTSG GTAALGCLVEDYFPEPVTVSWNSGALTSGVHTFPAVLQSSGLYSLSSV VTVPSSSLGTQTYICNVNHKPSNTKVDEKVEPKSCDGGGSGGGGSQA VVTQEPSLTVSPGGTVTLTCGSSTGAVTTSNYANWVQEKPGQAFRGLI GGTNKRAPGTPARFSGSLLGGKAALTLSGAQPEDEAEYYCALWYSNLW VFGGGTKLTVLSSASTKGPSVFPLAPSSKSTSGGTAALGCLVKDYFPE PVTVSWNSGALTSGVHTFPAVLQSSGLYSLSSVVTVPSSSLGTQTYIC NVNHKPSNTKVDKKVEPKSCDKTHTCPPCPAPEAAGGPSVFLFPPKPK DTLMISRTPEVTCVVVDVSHEDPEVKFNWYVDGVEVHNAKTKPREEQY NSTYRVVSVLTVLHQDWLNGKEYKCKVSNKALGAPIEKTISKAKGQPR EPQVYTLPPCRDELTKNQVSLWCLVKGFYPSDIAVEWESNGQPENNYK TTPPVLDSDGSFFLYSKLTVDKSRWQQGNVFSCSVMHEALHNHYTQKA LSLSP | 29 |
| Molecule C (STEAP-1 VH-CH1(EE)- Fc(knob), PGLALA)) | EVQLVESGGGLVQPGGSLRLSCAVSGYSITSDYAWNWVRQAPGKGLEW VGYISNSGSTYTYNPSLKSRFTISRDTSKNTLYLQMNSLRAEDTAVYY CARERNYDYDEYYYAMDYWGQGTLVTVSSASTKGPSVFPLAPSSKSTS GGTAALGCLVEDYFPEPVTVSWNSGALTSGVHTFPAVLQSSGLYSLSS VVTVPSSSLGTQTYICNVNHKPSNTKVDEKVEPKSCDKTHTCPPCPAP EAAGGPSVFLFPPKPKDTLMISRTPEVTCVVVDVSHEDPEVKFNWYVD GVEVHNAKTKPREEQYNSTYRVVSVLTVLHQDWLNGKEYKCKVSNKAL GAPIEKTISKAKGQPREPQVCTLPPSRDELTKNQVSLSCAVKGFYPSD IAVEWESNGQPENNYKTTPPVLDSDGSFFLVSKLTVDKSRWQQGNVFS CSVMHEALHNHYTQKSLSLSP | 30 |
| Molecule C (STEAP-1 VH-CH1(EE)-CD3 VL-CH1-Fc(knob), PGLALA)) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYDEYYYANDYWGQGTLVTVSSASTKGPHTFPAVLQSSGLYS LSSVVTVPSSSLGTQTYICNVNHKPSNTKVDEKVEPKSCDGGGSGGGG GSWAVVTQEPSLTVSPGGTVTLTCGSSTGAVTTSNYANWVQEKPGQAF RGLIGGTNKRAPGTPARFSGSLLGGKAALTLSGAQPEDEAEYYCALWY SNLWVFGGGTKLTVLSSASTKGPSVFPLAPSSKSTSGGTAALGCLVKD YFPEPVTVSWNSGALTSGVHTFPAVLQSSGLYSLSSVVTVPSSSLGTQ TYICNVNHKPSNTKVDKKVEPKSCDKTHTCPPCPAPEAAGGPSVFLFP PKPKDTLMISRTPEVTCVVVDVSHEDPEVKFNWYVDGVEVHNAKTKPR EEQYNSTYRVVSVLTVLHQDWLNGKEYKCKVSNKALGAPIEKTISKAK GQPREPQVYTLPPCRDELTKNQVSLWCLVKGFYPSDIAVEWESNGQPE NNYKTTPPVLDSDGSFFLYSKLTVDKSRWQQGNVFSCSVMHEALHNHY TQKSLSLSP | 31 |

| | Amino Acid Sequence | SEQ ID NO |
|---|---|---|
| Molecule D (STEAP-1 VH(CH1(EE)-Fc(knob), PGLALA)) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYEEYYYAMDYWGQGTLVTVSSASTKGPSVFPLAPSSKSTSG GTAALGCLVEDYFPEPVTVSWNSGALTSGVHTFPAVLQSSGLYSLSSV VTVPSSSLGTQTYICNVNHKPSNTKVDKEVEPKSCDKTHTCPPCPAPE AAGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALG APIEKTISKAKGQPREPQVCTLPPSRDELTKNQVSLSCAVKGFYPSDI AVEWESNGQPENNYKTTPPVLDSDGSFFLVSKLTVDKSRWQQGNVFSC SVMHEALHNHYTQKSLSLSP | 32 |
| Molecule D (STEAP-1 VH-VH1(EE)-CD3 VL-CH1-Fc(knob), PGLALA)) | EVQLVESGGGLVQPGGSLRLSCAVSGYSITSDYAWNWVRQAPGKGLEW VGYISNSGSTSYNPSLKSRFTISRDTSKNTLYLQMNSLRAEDTAVYYC ARERNYDYEEYYYAMDYWGQGTLVTVSSASTKGPSVFPLAPSSKSTSG GTAALGCLVEDYFPEPVTVSWNSGLATSGVHTFPAVLQSSGLYSLSSV VTVPSSSLGTQTYICNVNHKPSNTKVDEKVEPKSCDGGGSGGGGSQA VVTQEPSLTVSPGGTVTLTCGSSTGAVTTSNYANWVQEKPGQAFRGLI GGTNKRAPGTPARFSGSLLGGKAALTLSGAQPEDEAEYYCALWYSNLW VFGGGTKLTVLSSASTKGPSVFPLAPSSKSTSGGTAALGCLVKDYFPE PVTVSWNSGALTSGVHTFPAVLQSSGLYSLSSVVTVPSSSLGTQTYIC NVNHKPSNTKVDKKVEPKSCDKTHTCPPCPAPEAAGGPSVFLFPPKPK DTLMISRPTEVTCVVVDVSHEDPEVKFNWYVDGVEVHNAKTKPREEQY NSTYRVVSVLTVLHQDWLNGKEYKCKVSNKALGAPIEKTISKAKGQPR EPQVYTLPPCRDELTKNQVSLWCLVKGFYPSDIAVEWESNGQPENNYK TTPPVLDSDGSFFLYSKLTVDKSRWQQGNVFSCSVMHEALHNHYTQKS LSLSP | 33 |
| Molecule A-D (STEAP-1 VL-CL(RK)) | DIQMTQSPSSLSASVGDRVTITCKSSQSLLYRSNQKNYLAWYQQKPGK APKLLIYWASTRESGVPSRFSGSGSGTDFTLTISSLQPEDFATYYCQQ YYNYPRTFGQGTKVEIKRTVAAPSVFIFPPSDRKLKSGTASVVCLLNN FYPREAKVQWKVDNALQSGNSQESVTEQDSKDSTYSLSSTLTLSKADY EKHKVYACEVTHQGLSSPVTKSFNRGEC | 34 |
| Molecule A-D (CD3 VH-CL) | EVQLLESGGGLVQPGGSLRLSCAASGFTFSTYAMNWVRQAPGKGLEWV SRIRSKYNNYATYYADSVKGRFTISRDDSKNTLYLMQNSLRAEDTAVY YCVRHGNFGNSYVSWFAYWGQGTLVTVSSASVAAPSVFIFPPSDEQLK SGTASVVCLLNNFYPREAKVQWKVDNALQSGNSQESVTEQDSKDSTYS LSSTLTLSKADYEKHKVYACEVTHQGLSSPVTKSFNRGEC | 35 |
| hIgG1 Fc region | DKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNG KEYKCKVSNKALPAPIEKTISKAKGQPREPQVYTLPPSRDELTKNQVS LTCLVKGFYPSDIAVEWESNGQPENNYKTTPPVLDSDGSFFLYSKLTV DKSRWQQGNVFSCSVMHEALHNHYTQKSLSLSP | 36 |
| linker | GGGGSGGGGS | 37 |
| linker | DGGGGSGGGGS | 38 |
| Human kappa CL domain | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC | 39 |
| Human lambda CL domain | QPKAAPSVTLFPPSSEEQANKATLVCLISDFYPGAVTVAWKADSSPVK AGVETTTPSKQSNNKYAASSYLSLTPEQWKSHRSYSCQVTHEGSTVEK TVAPTECS | 40 |
| Human IgG1 heavy chain constant region (CH1—CH2—CH3) | ASTKGPSVFPLAPSSKSTSGGTAALGCLVKDYFPEPVTVSWNSGALTS GVHTFPAVLQSSLGYSLSSVVTVPSSSLGTQTYICNVNHKPSNTKVDK KVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDE LTKNQVSLTCLVKGFYPSDIAVEWESNGQPENNYKTTPPVLDSDGSFF LYSKLTVDKSRWQQGNVFSCSVMHEALHNHYTQKSLSLSP | 41 |

EXAMPLES

The following are examples of methods and compositions of the invention. It is understood that various other embodiments may be practiced, given the general description provided above.

Example 1

Generation of Constructs and Tools

Recombinant DNA Techniques

Standard methods were used to manipulate DNA as described in Sambrook, J. et al, Molecular cloning: A laboratory manual; Cold Spring Harbor Laboratory press, Cold spring Harbor, N.Y., 1989. The molecular biological reagents were used according to the manufacturer's instructions.

General information regarding the nucleotide sequences of human immunoglobulin light and heavy chains is given in; Kabat, E. A., et al., Sequences of Proteins of Immunological Interest, 5th ed., Public Health Service, National Institutes of Health, Bethesda, Md. (1991).

Gene Synthesis

Desired gene segments, where required, were either generated by PCR using appropriate templates or were synthesized at Geneart A G (Regensburg, Germany) from synthetic oligonucleotides and PCR products by automated gene synthesis. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells.

DNA Sequencing

DNA sequences were determined by double strand sequencing

Cloning of Anti-STEAP1/Anti-CD3 T Cell Bispecific (TCB) Antibodies

The variable domains of vandortuzumab were used for the generation of various STEAP1-specific T cell bispecific (TCB) antibody variants. For the generation of the respective expression plasmids, the variable region sequences of vandortuzumab (SEQ ID NOs 10 and 14) or variants thereof were used and sub-cloned in frame with the respective constant regions which are pre-inserted in the respective recipient mammalian expression vector. A schematic illustration of the resulting molecules is shown in FIG. 2.

Preparation of Anti-STEAP1/Anti-CD3 T Cell Bispecific (TCB) Antibodies

Figure 2:
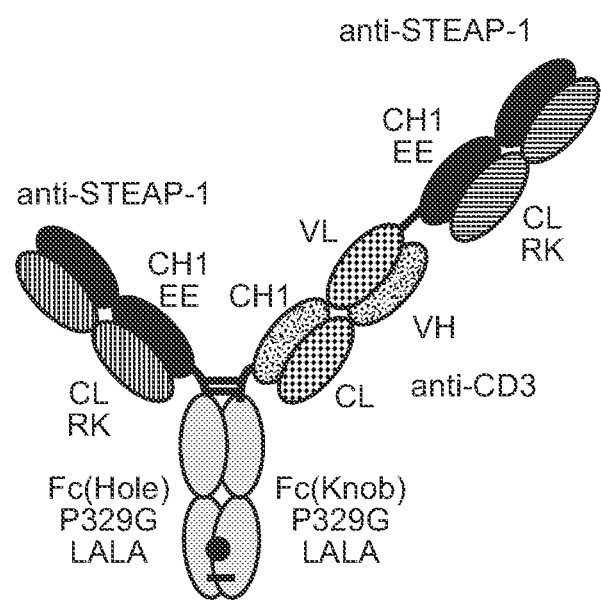
FIG. 2. Illustration of the T-cell bispecific (TCB) antibody molecules prepared in the Examples. All tested TCB antibody molecules were produced as "2+1 IgG CrossFab, inverted" with charge modifications (VH/VL exchange in CD3 binder, charge modifications in STEAP1 binders, EE=147E, 213E: RK=123R, 124K).

The following molecules were prepared, a schematic illustration thereof is provided in FIG. 2:

A. Molecule A: 2+1 IgG CrossFab "inverted" (CD3 binder C-terminal to STEAP1 binder), with charge modifications (VH/VL exchange in CD3 binder, charge modification in STEAP1 binder) (SEQ ID NOs 26, 27, 34 and 35)
B. Molecule B: 2+1 IgG CrossFab "inverted" (CD3 binder C-terminal to STEAP1 binder), with charge modifications (VH/VL exchange in CD3 binder, charge modification in STEAP1 binder; D100aE mutation in both STEAP1 binding moieties) (SEQ ID NOs 28, 29, 34 and 35)
C. Molecule C: 2+1 IgG CrossFab "inverted" (CD3 binder C-terminal to STEAP1 binder), with charge modifications (VH/VL exchange in CD3 binder, charge modification in STEAP1 binder; D100bE mutation in both STEAP1 binding moieties) (SEQ ID NOs 30, 31, 34 and 35)
D. Molecule D: 2+1 IgG CrossFab "inverted" (CD3 binder C-terminal to STEAP1 binder), with charge modifications (VH/VL exchange in CD3 binder, charge modification in STEAP1 binder; D100aE/D100bE mutations in both STEAP1 binding moieties) (SEQ ID NOs 32, 33, 34 and 35)

Expression of the above-mentioned molecules was either driven by a chimeric MPSV promoter or a CMV promoter. Polyadenylation was driven by a synthetic polyA signal sequence located at the 3' end of the CDS. In addition, each vector contained an EBV OriP sequence for autosomal replication.

For the production of all constructs, HEK293-EBNA cells growing in suspension were co-transfected with the respective expression vectors using polyethylenimine as a transfection reagent. As such, for the production of all "2+1 IgG CrossFab" constructs, the corresponding expression vectors were co-transfected in a 1:2:1:1 ratio ("vector heavy chain (VH—CH1-VL-CH1-CH2-CH3)": "vector light chain (VL-CL)": "vector heavy chain (VH—CH1-CH2-CH3)": "vector light chain (VH-CL)").

HEK293 EBNA cells were cultivated in suspension in serum free Excell culture medium containing 6 mM L-Glutamine and 250 mg/I G418. For the production in 600 ml tubespin flasks (max, working volume 400 mL) 600 million HEK293 EBNA cells were seeded 24 hours before transfection. Before transfection, cells were centrifuged for 5 min by 210×g and supernatant was replaced by pre-warmed 20 ml CD CHO medium. Expression vectors were mixed in 20 ml CD CHO medium to a final amount of 400 µg DNA. After addition of 1080 µl PEI solution (2.7 µg/ml), the medium was vortexed for 15 s and subsequently incubated for 10 min at room temperature. Afterwards, cells were mixed with the DNA/PEI solution, transferred to a 600 ml tubespin flask and incubated for 3 hours at 37° C. in an incubator with a humidified 5% $CO_2$ atmosphere. After this incubation step, 360 ml Excell medium containing 6 mM L-Glutamine, 5 g/L Pepsoy, and 1.0 mM VPA was added and cells were cultivated for 24 hours. One day after transfection, 7% Feed 7 is added. After 7 days of cultivation, supernatant was collected for purification by centrifugation for 20-30 min at 3600×g (Sigma 8K centrifuge), the solution was sterile filtered (0.22 µm filter) and sodium azide was added to a final concentration of 0.01% w/v, and kept at 4° C.

All molecules were purified from cell culture supernatants by Protein A affinity chromatography, followed by a size exclusion chromatographic step. For affinity chromatography, supernatant was loaded on a HiTrap ProteinA HP column (0 5 mL, GE Healthcare) equilibrated with 25 ml 20 mM sodium phosphate, 20 mM sodium citrate, pH 7.5. Unbound protein was removed by washing with at least 10 column volumes 20 mM sodium phosphate, 20 mM sodium citrate, pH 7.5. Target protein was eluted in 6 column volumes 20 mM sodium citrate, 100 mM sodium chloride, 100 mM glycine, pH 3.0. Protein solution was neutralized by adding 1/10 volume of 0.5 M sodium phosphate, pH 8.0. For in-process analytics after Protein A chromatography, the purity and molecular weight of the molecules in the single fractions were analyzed by SDS-PAGE in the absence of a reducing agent and stained with Coomassie (InstantBlue™ from Expedeon). The NuPAGE® Pre-Cast gel system (4-12% Bis-Tris, Invitrogen, USA) was used according to the manufacturer's instruction. Selected fractions of the target protein were concentrated and filtrated prior to loading on a HiLoad Superdex 200 column (GE Healthcare) equilibrated with 20 mM histidine, 140 mM sodium chloride, pH 6.0, 0.01% Tween20.

The protein concentration of the purified protein samples was determined by the optical density (OD) at 280 nm using the molar extinction coefficient which was calculated on the basis of the amino acid sequence. In addition, mass spectrometry analysis of all molecules was performed in order to confirm their identity.

Generation of a STEAP1 Expressing CHO-K1 Cell Line

A gene encoding full-length human STEAP1 was subcloned into mammalian expression vector. The plasmid was transfected into CHO-K1 (ATCC CRL-9618) cells using Lipofectamine LTX Reagent according to the manufacturer's protocol (Invitrogen, #15338100). Stably transfected STEAP1-positive CHO cells were maintained in DMEM/F-12 medium (Gibco, #11320033) supplemented with 10% fetal bovine serum (Gibco, #16140063) and 1% GlutaMAX Supplement (Gibco; #31331-028). Two days after transfection, puromycin (Invivogen; #ant-pr-1) was added to 6 μg/mL and the cells were cultured for several passages. After initial selection, the cells with the highest cell surface expression of STEAP1 were sorted by BD FACSAria II cell sorter (BD Biosciences) and cultured to establish stable cell clones. The expression level and stability was confirmed by FACS analysis using vandortuzumab and PerCP-conjugated Fc gamma-specific goat anti-human IgG (Jackson ImmunoResearch, #109-126-097) as secondary antibody over a period of 4 weeks.

Example 2

Generation and Characterization of Vandortuzumab-Based Sequence Variants

Sequence Analysis of Vandortuzumab

Modifications like asparagine deamidation, aspartate isomerization, succinimide formation, and tryptophan oxidation are typical degradations for recombinant antibodies and can affect both in vitro stability and in vivo biological functions. A computational analysis of the vandortuzumab CDR sequences (SEQ ID NOs 1, 2, 3, 7, 8 and 9, according to Kabat) was performed in order to screen for the presence of potential amino acid sequence patterns that are prone to aspartate isomerization, asparagine deamidation or succinimide formation. Furthermore, CDR regions were analyzed for the presence of tryptophans that have the potential to oxidize. As shown in FIG. 3A and FIG. 3B, the analysis of the vandortuzumab sequences revealed potential hotspots in the CDR regions of the variable domains of both heavy and light chains.

Generation of Variants of the Vandortuzumab Sequence (Molecules B-D)

In order to prepare an anti-STEAP1 antibody with minimal iso-aspartate and succinimide formation and optimal stability, several variants of the vandortuzumab sequence were generated with a modified HCDR3 sequence. In particular, the aspartate residues at position 100a and 100b (Kabat numbering) were replaced by glutamate either individually or in combination (SEQ ID NOs 4, 5 and 6) and the resulting plasmids (SEQ ID NOs 28, 29, 34 and 35 (mutation D100aE, Molecule B); SEQ ID NOs 30, 31, 34 and 35 (mutation D100bE, Molecule C); SEQ ID NOs 32-35 (mutations D100aE/D100bE, Molecule D)) were generated for the expression of the respective TCB antibody molecules.

Chemical Degradation Test

In order to confirm that the introduced mutations eliminate the predicted hotspot in HCDR3, increase the stability and prevent loss of binding potency of the anti-STEAP1 antibodies, all constructs (Molecules A-D) were split into two aliquots, re-buffered into 20 mM His/HisCl, 140 mM NaCl, pH 6.0 or into PBS, pH 7.4, respectively, and incubated at 40° C. (His/NaCl) or 37° C. (PBS). In addition, a control sample was stored at −80° C. Incubation at pH 7.4 reflects the exposure of the molecule to the situation in the blood plasma and allows drawing conclusions about the stability of the molecule in vivo. In contrast, buffer formulations with reduced pH (here pH 6) are more suitable for long term storage of antibody-based constructs and stress tests under these conditions are predictive for the shelf life of a molecule.

After an incubation period of 28 days, samples were analyzed and compared for the binding potency (relative active concentration) of the STEAP1-binding moieties. This analysis was performed indirectly by mass spectrometry and a cell-based ELISA.

Characterization of Stressed Molecule A-D by Mass Spectrometry

In order to identify stress-induced protein degradation at predicted positions within the CDRs of vandortuzumab and variants thereof, mass spectrometry of Molecules A-D was performed, 80 μg reference and stressed protein samples were denatured and reduced for 1 h in 124.5 μl 100 mM Tris, 5.6 M guanidinium hydrochloride, 10 mM TCEP (tris(2-carboxyethyl)phosphine (Pierce Protein Biology Products), pH 6.0 at 37° C. Buffer was exchanged to 20 mM histidine chloride, 0.5 mM TCEP, pH 6.0 in 0.5 mL Zeba Spin Desalting Columns (Pierce Protein Biology Products). Protein samples were digested overnight at 37° C. after addition of 0.05 μg trypsin (Promega) per μg protein in a final volume of 140 μL. Digestion was stopped by addition of 7 μL of 10% formic acid (FA) solution.

The digested samples were stored at −80° C. until use. Analysis was performed by UHPLC-MS/MS using a nano-Acquity UPLC (Waters) and an Orbitrap Fusion mass spectrometer (Thermo Fisher Scientific). About 2.4 μg digested fusion protein was injected in 5 μL. Chromatographic separation was performed by reversed-phase on a Acquity BEH300 C18 column, 1×150 mm, 1.7 μm, 300 Å (Waters) using a flow rate of 60 μL/min. The mobile phase A and B contained 0.1% (v/v) formic acid in UPLC grade water and acetonitrile, respectively. A column temperature of 50° C. was used and a gradient of 1% to 40% mobile phase B over 90 min was applied. The Orbitrap Fusion was used in the data-dependent mode. Essential MS settings were: ionization (spray voltage: 3.6 kV, ion transfer tube: 250° C., vaporizer: 100° C.), full MS (AGC: 2×105, resolution: 12×104, m/z range: 300-2000, maximum injection time: 100 ms); MS/MS (AGC: 1×104, maximum injection time: 100 ms, isolation width: 2 Da). Normalized collision energy was set to 35%.

Peptide mapping was applied to quantify deamidation, isomerization and oxidation levels of the predicted hotspots (N53 (HCDR2), N97 (HCDR3), D100a (HCDR3) and W50 (LCDR2) (Kabat numbering)) for Molecules A-D.

In the peptides harboring the HCDR3 region, no deamidation or succinimide formation at position N97 was detected in either of the Molecules A-D, at either condition (data not shown). However, stress exposure at pH 6 resulted in different levels of aspartate degradation in the same HCDR3 peptide that also harbors the predicted hotspot aspartate 100a. Different levels of succinimide and iso-aspartate formation were detected after 4 weeks in His/NaCl pH 6.0 at 40° C. in the respective tryptic peptides of the four tested molecules (Table 1). After stress exposure at pH 6.0, the highest total levels were detected in Molecule A. Introduction of mutation of D100a→E100a in Molecule B as well as D100b→E100b in Molecule C lead to significant decreases of the succinimide level. However, combination of both mutations (D100aE/D100bE) (Molecule D) strongly reduced the succinimide levels to 3%, a negligible amount for this long period of stress exposure. Furthermore, no iso-aspartate was detected in Molecule D. The results indicate that both aspartates (D100a and D100b) in Molecule A and either one of the aspartates (D100a or D100b) in Molecules C or B contribute to the total succinimide and iso-aspartate levels found after stress. In addition, no protein degradation at all was detected in HCDR3 of Molecule D after stress exposure at pH 7.4 confirming the integrity of this newly designed sequence variant.

TABLE 1

Relative quantification of protein degradation in HCDR3.

| Sample | Tryptic peptide with indicated mutations* | 4 weeks in His/NaCl pH 6.0 at 40° C. | | 4 weeks in PBS pH 7.4 at 37° C. | | His/NaCl pH 6.0 control | |
|---|---|---|---|---|---|---|---|
| | | iso-asp [%] | succinimide [%] | iso-asp [%] | succinimide [%] | iso-asp [%] | succinimide [%] |
| Molecule A | ERNYDYDDYYYAMDY WGQGTLVTVSSASTK | 1.4 | 12.7 | not detected | 5.3 | not detected | 4.2 |
| Molecule B | ERNYDYEDYYYAMDY WGQGTLVTVSSASTK | 5.3 | 5.0 | 2.7 | 0.9 | 2.8 | 1.1 |
| Molecule C | ERNYDYDEYYYAMDY WGQGTLVTVSSASTK | 1.2 | 6.2 | 0.8 | 1.3 | 0.04 | 1.5 |
| Molecule D | ERNYDYEEYYYAMDY WGQGTLVTVSSASTK | not detected | 3.0 | not detected | not detected | not detected | not detected |

*Mutated positions bold and underlined

Analysis of the peptide harboring position N53 in the heavy chain (HCDR2) of the STEAP binder revealed in all constructs a small increase of N53 deamidation after 4 weeks in PBS, pH 7.4 at 37° C., whereas no significant increase at pH 6 was detected (Table 2). Oxidation of W50 (LCDR2) was below 2% for all samples (Table 3). Consequently no molecule optimizations regarding these putative hotspots were performed.

TABLE 2

Relative quantification of the protein degradation at position N53 (HCDR2).

| Sample | Tryptic peptide* | Deamidation (%) | | |
|---|---|---|---|---|
| | | ph 7.4, 37° C. | ph 6, 40° C. | No stress |
| Molecule A | GLEWVGYISNSGSTSYNPSLK | 3.4 | 1.3 | 1.2 |
| Molecule B | GLEWVGYISNSGSTSYNPSLK | 3.7 | 1.6 | 1.2 |
| Molecule C | GLEWVGYISNSGSTSYNPSLK | 3.2 | 1.5 | 1.2 |
| Molecule D | GLEWVGYISNSGSTSYNPSLK | 3.3 | 1.5 | 1.4 |

*Position of predicted hotspot N53 bold and underlined

TABLE 3

Relative quantification of the protein degradation at position W50 (LCDR2).

| Sample | Tryptic peptide* | Oxidation products [%] |
|---|---|---|
| Molecule A | LLIYWASTR | 1.7 |
| Molecule B | LLIYWASTR | 1.2 |
| Molecule C | LLIYWASTR | 0.7 |
| Molecule D | LLIYWASTR | 1.0 |

*Position of predicted hotspot W50 bold and underlined.

Characterization of Binding Potency after Stress Using a Cell-Based ELISA

To quantify the reduction in binding potency caused by 1-4 weeks stress at either pH 7.4 or 6.0, a cell-based ELISA was employed using CHO-K1 cells stably expressing human STEAP1. For this III cell-based ELISA, 10,000 cells were seeded per well of a 96-well plate and incubated for 18 h at 37° C., 5% $CO_2$. Supernatant was removed using an automated washer (BIOTEK), and 100 µl of a dilution series (10 µM-30 nM) of antibody constructs in growth medium was added to each well. After 1 h of incubation at 4° C., wells were emptied and 100 µl of 0.05% glutaraldehyde in PBS added for 10 min at RT. After 4 washes with PBS/0.025% Tween20 (PBST), 100 µl of anti-human-IgG-HRP (Jackson) diluted 1:20000 in Blocking buffer (Roche) was added and plates incubated for 1 h at room temperature (RT). Wells were washed 6 times with PBST and signal was generated using 100 µl of TMB per well, the reaction stopped after 10 minutes with 50 µl 1 M HCl and absorbance measured at 450 nm. Data (Table 4) were expressed as "% binding", dividing the binding EC50 of the stressed sample by that of the untreated sample multiplied by 100.

Given that all tested TCB antibodies comprise two STEAP1-binding moieties per molecule and considering that the affinity of monovalent binding to STEAP1 is in the range of 40-60 nM, it is conceivable that only molecules with two functional STEAP1-binding moieties can be detected in this ELISA. In contrast, molecules with only one functional STEAP1 binding moiety are supposed to be washed away during the washing steps described in this protocol. Therefore, the cumulative percentage of binding loss for the molecules with elevated succinimide levels is higher than the detected protein degradation in HCDR3 (Molecules A-C).

TABLE 4

Quantification of the protein binding potency to STEAP1 after 28 days at 40° C., pH 6.

| probe | Relative binding potency (%) (after 28 days at 40° C., pH 6) |
|---|---|
| Molecule A | 66 |
| Molecule B | 79 |
| Molecule C | 69 |
| Molecule D | 100 |

Biochemical Characterization of the Vandortuzumab-Based TCB Antibody Variants (Molecules A-D)

In order to characterize and compare their biochemical and biophysical properties, all TCBs with new anti-STEAP-1 antibody sequence variants (Molecules B-D) were analyzed and compared with the TCB antibody harboring the vandortuzumab sequence (Molecule A). The results are summarized in Table 5:

Hydrophobic Interaction Chromatography (HIC)

Apparent hydrophobicity was determined by injecting 20 µg of sample onto a HIC-Ether-5PW (Tosoh) column equilibrated with 25 mM Na-phosphate, 1.5 M ammonium sulfate, pH 7.0. Elution was performed with a linear gradient from 0 to 100% buffer B (25 mM Na-phosphate, pH 7.0) within 60 minutes. Retention times were compared to protein standards with known hydrophobicity.

Thermal Stability

Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering on a DynaPro Plate Reader (Wyatt) while the samples are heated with a rate of 0.05° C./min from 25° C. to 80° C.

FcRn Affinity Chromatography

FcRn was expressed, purified and biotinylated as described (Schlothauer et al., MAbs (2013) 5(4), 576-86). For coupling, the prepared receptor was added to streptavidin-sepharose (GE Healthcare). The resulting FcRn-sepharose matrix was packed in a column housing. The column was equilibrated with 20 mM 2-(N-morpholine)-ethanesulfonic acid (MES), 140 mM NaCl, pH 5.5 (eluent A) at a 0.5 ml/min flow rate. 30 µg of antibody samples were diluted at a volume ratio of 1:1 with eluent A and applied to the FcRn column. The column was washed with 5 column volumes of eluent A followed by elution with a linear gradient from 20 to 100% 20 mM Tris/HCl, 140 mM NaCl, pH 8.8 (eluent B) in 35 column volumes. The analysis was performed with a column oven at 25° C. The elution profile was monitored by continuous measurement of the absorbance at 280 nm. Retention times were compared to protein standards with known affinities.

Heparin Affinity Chromatography

Heparin affinity was determined by injecting 30-50 µg of sample onto a TSKgel Heparin-5PW (Tosoh) column equilibrated with 50 mM Tris, pH 7.4. Elution was performed with a linear gradient from 0 to 100% buffer B (50 mM Tris, 1M NaCl, pH 7.4 mM) within 37 minutes. Retention times were compared to protein standards with known affinities.

No significant difference was found between any of the tested TCBs with new anti-STEAP-1 antibody sequence variants (Molecules B-D) and the molecule harboring the vandortuzumab sequence (Molecule A) with regard to all tested biophysical and biochemical properties (Table 5). All samples showed only marginal aggregation and fragmentation upon stress, supporting that observed activity losses after stress exposure at pH 6 (Molecules A-C) are due to chemical protein degradation at the identified positions in the HCDR3 region.

TABLE 5

Biophysical and biochemical properties of tested variants.

| Sample | Thermal stability (° C.) | Apparent hydophobicity | FcRn affinity | Heparin affinity |
|---|---|---|---|---|
| Molecule A | 58 | 0.10 | 0.61 | 0.85 |
| Molecule B | 58 | 0.16 | 0.69 | 0.85 |

TABLE 5-continued

Biophysical and biochemical properties of tested variants.

| Sample | Thermal stability (° C.) | Apparent hydophobicity | FcRn affinity | Heparin affinity |
|---|---|---|---|---|
| Molecule C | n.d. | n.d. | n.d. | n.d. |
| Molecule D | 58 | 0.11 | 0.65 | 0.85 | n.d.: not determined

Example 3

Functional Characterization of STEAP-1 TCB Antibody Variants

T-Cell Mediated Tumor Lysis, Induced by STEAP-1 TCB Antibody Variants

T-cell killing mediated by different STEAP-1 TCB antibody variants (Molecules A-D) was assessed on STEAP-1 expressing LnCAP cells. Human peripheral blood mononuclear cells (PBMCs) were used as effector cells and the killing was detected at 24 h and 48 h of incubation with the bispecific antibodies. Adherent target cells were harvested with Trypsin/EDTA, washed, and plated at a density of 30 000 cells/well using flat-bottom 96-well plates. Cells were left to adhere overnight. PBMCs were prepared by Histopaque density centrifugation of enriched lymphocyte preparations of heparinized blood obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom. K0302) at 37° C. 5% $CO_2$ in cell incubator until further use (no longer than 24 h).

Figure 4A:
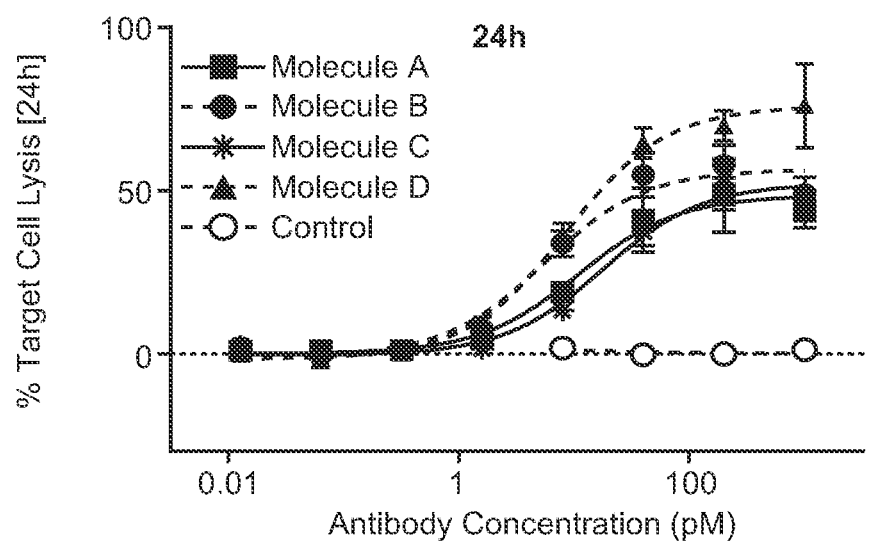
FIG. 4A-FIG. 4B. T-cell mediated lysis of STEAP-1 expressing LnCAP cells after 24 h (FIG. 4A) or 48 h (FIG. 4B), induced by different STEAP-1 TCB antibody molecules (E:T=10:1, human PBMC effector cells). Depicted are triplicates with SD.
Figure 4B:
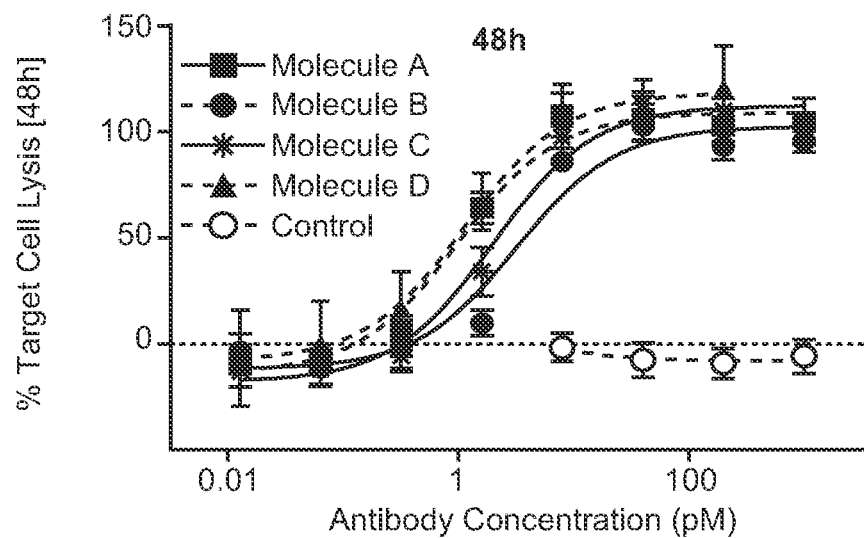

For the killing assay, the antibodies were added at the indicated concentrations (range of 0.01 µM-1 nM in triplicates. PBMCs were added to target cells to obtain a final E:T ratio of 10:1. Target cell killing was assessed after 24 h and 48 h of incubation at 37° C., 5% $CO_2$ by quantification of LDH released into cell supernatants by apoptotic/necrotic cells (LDH detection kit, Roche Applied Science. #11 644 793 001). Maximal lysis of the target cells (=100%) was achieved by incubation of target cells with 1% Triton X-100. Minimal lysis (=0%) refers to target cells co-incubated with effector cells without bispecific construct. The results after 24 h (FIG. 4A) and 48 h (FIG. 4B) show that T-cell mediated tumor lysis is induced similarly by the tested molecules and that the modification of the STEAP-1 binder in Molecules B-D does not negatively affect the killing potency of the molecules.

T-Cell Activation Induced by STEAP-1 TCB Antibody Variants (Jurkat-NFAT Activation Assay)

The capacity of the STEAP-1 TCB antibody variants to induce CD3-mediated activation of effector cells upon simultaneous binding to CD3 and human STEAP-1 on cells, was assessed using co-cultures of tumor antigen positive target cells (LnCAP, 22RV1) and Jurkat-NFAT reporter cells (a CD3-expressing human acute lymphatic leukemia reporter cell line with a NFAT promoter; GloResponse Jurkat NFAT-RE-luc2P, Promega #CS176501). Upon simultaneous binding of the TCB molecule to the STEAP-1 antigen (expressed on target cells) and CD3 antigen (expressed on Jurkat-NFAT reporter cells), the NFAT promoter is activated and leads to expression of active firefly luciferase. The intensity of luminescence signal (obtained upon addition of luciferase substrate) is proportional to the intensity of CD3 activation and signaling.

For the assay, human tumor cells were harvested and viability was determined using ViCell. 20 000 cells/well were plated in a flat-bottom, white-walled 96-well-plate (#655098, greiner bio-one) and diluted antibodies or medium (for controls) was added (range of 2.6 µM-200 nM).

Subsequently, Jurkat-NFAT reporter cells were harvested and viability assessed using ViCell. Cells were re-suspended in cell culture medium and added to tumor cells to obtain a final effector-to-target (E:T) ratio of 5:1 and a final volume of 100 µl per well. Cells were incubated for 6 h at 37° C. in a humidified incubator. At the end of the incubation time, 100 µl/well of ONE-Glo solution (Promega; 1:1 ONE-Glo and assay medium volume per well) were added to wells and incubated for 10 min at room temperature in the dark. Luminescence was detected using WALLAC Victor3 ELISA reader (PerkinElmer2030), 5 sec/well as detection time.

Figure 5A:
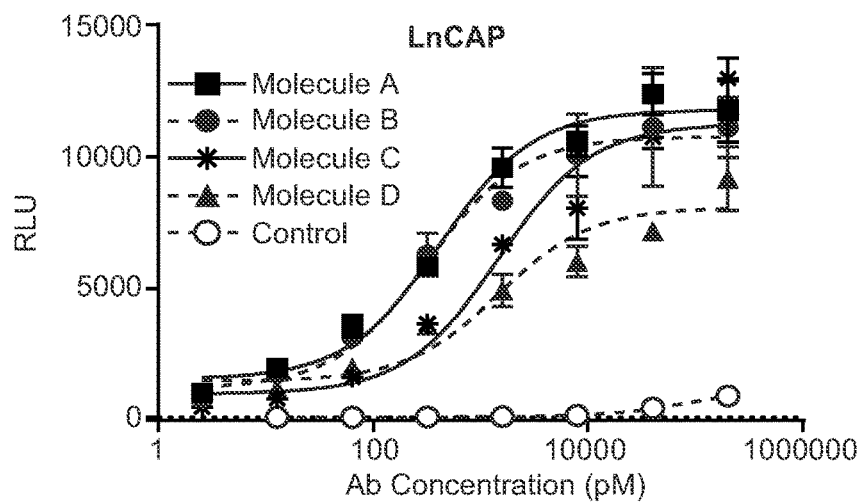
FIG. 5A-FIG. 5C. Jurkat activation, as determined by luminescence, upon simultaneous binding of different STEAP-1 TCB antibody molecules to human CD3 on Jurkat-NFAT reporter cells and human STEAP-1 on LnCAP (FIG. 5A) or 22Rv1 cells (FIG. 5B). The STEAP-1-negative CHO-K1 cell line served as control (FIG. 5C). Depicted are triplicates with SD.
Figure 5B:
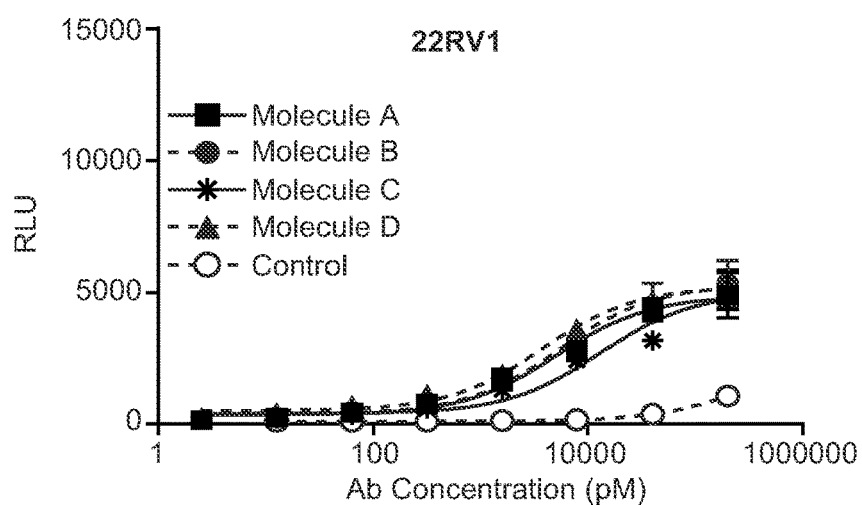
Figure 5C:
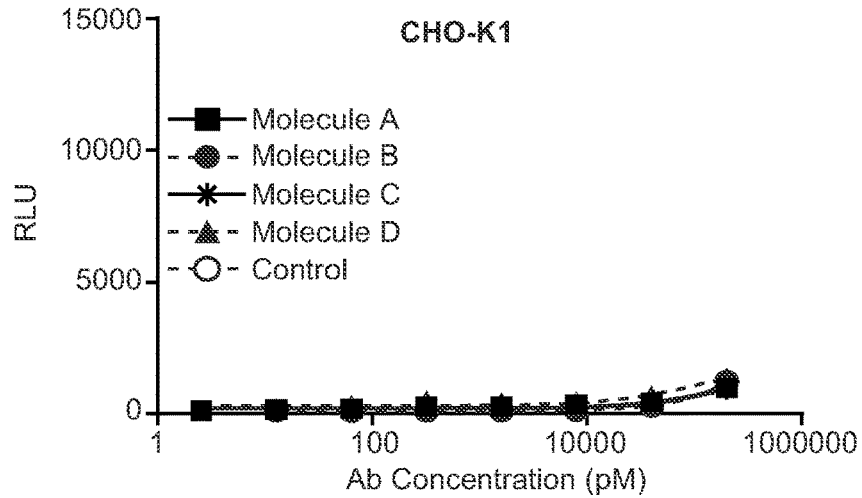

As shown in FIG. 5A-FIG. 5C, all evaluated STEAP-1 TCB antibody molecules induce T cell cross-linking via CD3 and subsequently T cell activation on STEAP1-expressing LnCAP (FIG. 5A) and 22Rv1 (FIG. 5B) cells. On STEAP1-negative CHO-K1 cells (FIG. 5C) no T cell activation can be observed.

Binding of STEAP-1 TCB Antibody Variants to STEAP-1- and CD3-Expressing Cells

The binding of STEAP-1 TCB antibody variants (Molecules A-D) was tested, using STEAP-1-expressing CHO-hSTEAP1 cells (an epithelial cell line derived from hamster ovary that was transfected to stably overexpress human STEAP-1) and CD3-expressing Jurkat-NFAT reporter cells (Promega #CS176501).

Briefly, adherent CHO-hSTEAP1 cells were harvested, using Cell Dissociation Buffer (Gibco, #13151014) counted, checked for viability and re-suspended at $2 \times 10^6$ cells/ml in FACS buffer (100 µl PBS 0.1% BSA). Jurkat suspension cells were also harvested, counted and checked for viability. 100 µl of cell suspension (containing $0.2 \times 10^6$ cells) were incubated in round-bottom 96-well plate for 30 mn at 4° C. with increasing concentrations of the STEAP-1 TCB antibodies (31 µM-1000 nM), washed twice with cold PBS containing 0.1% BSA (FACS buffer), re-incubated for further 30 min at 4° C. with the 1:50 pre-diluted Alexa Fluor 647-conjugated AffiniPure F(ab')$_2$ Fragment goat-human IgG Fcγ Fragment Specific secondary antibody (Jackson Immuno Research Lab, Alexa Fluor 647 #109-606-008, dilutions in FACS buffer) and washed twice with cold PBS 0.1% BSA.

The stained cells were re-suspended in 100 μL 2% paraformaldehyde-containing FACS Buffer and incubated for 30 min at 4° C. to fix the staining. Finally, cells were centrifuged for 4 min at 350×g and 4° C., the supernatants were discarded and the cell pellets re-suspended in 200 μl FACS Buffer. Staining was analyzed by FACS using a FACS Canto II (Software FACS Diva). Binding curves were obtained using GraphPadPrism6 (FIG. 6A, binding to CHO-hSTEAP1 cells; FIG. 6B, binding to Jurkat cells).

Figure 6A:
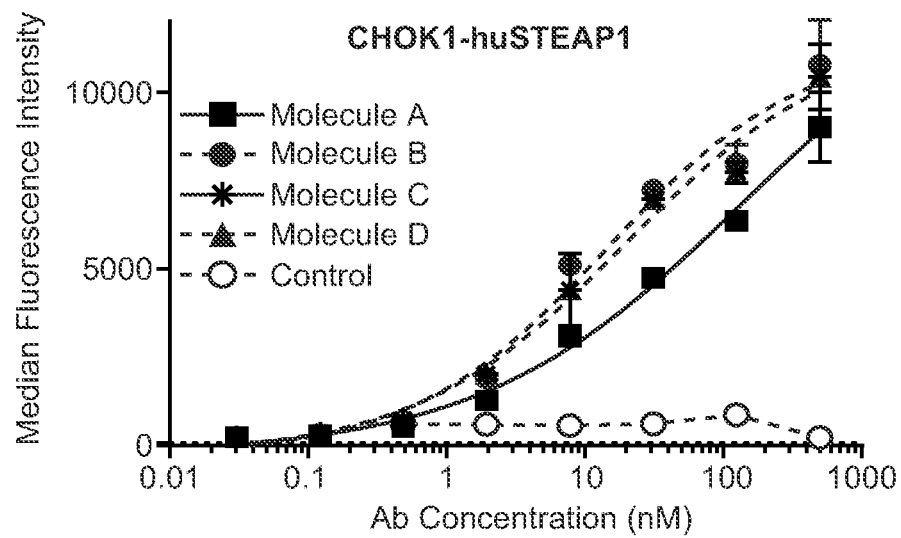
FIG. 6A-FIG. 6B. Binding of STEAP-1 TCB antibody molecules to human STEAP-1-expressing CHO-hSTEAP1 cells (FIG. 6A) and CD3-expressing Jurkat NFAT cells (FIG. 6B).
Figure 6B:
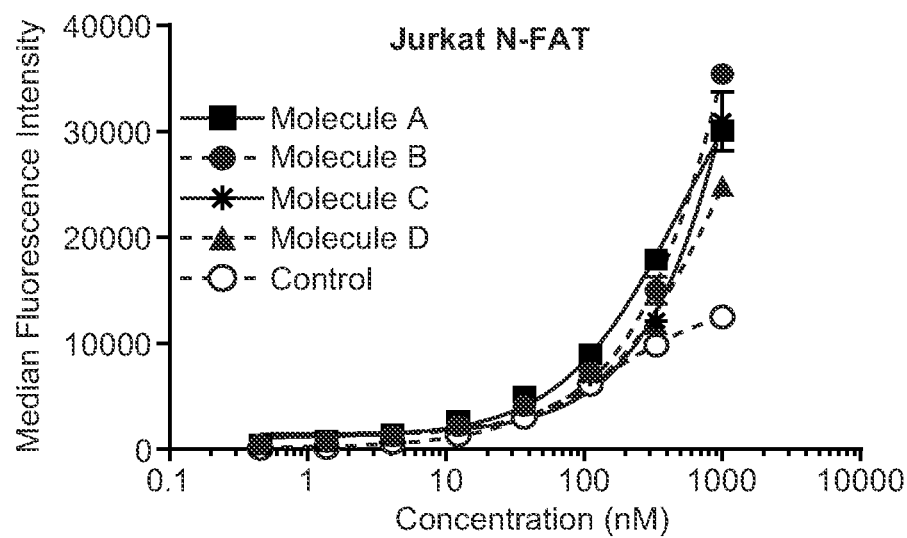

As shown in FIG. 6A-FIG. 6B, all evaluated STEAP-1 TCB antibody molecules show concentration-dependent binding to human CHO cells expressing human STEAP-1 (FIG. 6A) and to human CD3 expressed on Jurkat NFAT cells (FIG. 6B), indicating that the modification of the STEAP-1 binder in Molecules B-D does not negatively affect their binding to STEAP-1 on cells.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An antibody that binds to STEAP-1, wherein the antibody comprises a heavy chain variable region (VH) comprising a heavy chain complementarity determining region (HCDR) 1 of SEQ ID NO: 1, a HCDR 2 of SEQ ID NO: 2, and a HCDR 3 of SEQ ID NO: 4, and a light chain variable region (VL) comprising a light chain complementarity determining region (LCDR) 1 of SEQ ID NO: 7, a LCDR 2 of SEQ ID NO: 8 and a LCDR 3 of SEQ ID NO: 9.

* * * * *